(12) United States Patent
Vournakis et al.

(10) Patent No.: US 10,561,677 B2
(45) Date of Patent: *Feb. 18, 2020

(54) ANTI-BACTERIAL APPLICATIONS OF POLY-N-ACETYLGLUCOSAMINE NANOFIBERS

(71) Applicant: Marine Polymer Technologies, Inc., Burlington, MA (US)

(72) Inventors: John N. Vournakis, Charleston, SC (US); Sergio Finkielsztein, Newton, MA (US)

(73) Assignee: Marine Polymer Technologies, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,705

(22) Filed: Dec. 21, 2018

(65) Prior Publication Data

US 2019/0247410 A1 Aug. 15, 2019

Related U.S. Application Data

(63) Continuation of application No. 15/476,222, filed on Mar. 31, 2017, now Pat. No. 10,206,938, which is a continuation of application No. 14/927,372, filed on Oct. 29, 2015, now Pat. No. 9,642,871, which is a continuation of application No. 14/327,192, filed on Jul. 9, 2014, now Pat. No. 9,198,928, which is a continuation of application No. 13/641,015, filed as application No. PCT/US2011/032709 on Apr. 15, 2011, now Pat. No. 8,858,964.

(60) Provisional application No. 61/324,657, filed on Apr. 15, 2010.

(51) Int. Cl.
| | |
|---|---|
| A61K 31/7008 | (2006.01) |
| A61K 9/00 | (2006.01) |
| A61K 45/06 | (2006.01) |
| A61K 31/715 | (2006.01) |
| A61K 9/14 | (2006.01) |

(52) U.S. Cl.
CPC .......... *A61K 31/7008* (2013.01); *A61K 9/00* (2013.01); *A61K 9/0014* (2013.01); *A61K 9/0031* (2013.01); *A61K 9/14* (2013.01); *A61K 31/715* (2013.01); *A61K 45/06* (2013.01); *Y02A 50/401* (2018.01); *Y02A 50/402* (2018.01); *Y02A 50/469* (2018.01); *Y02A 50/47* (2018.01); *Y02A 50/473* (2018.01); *Y02A 50/475* (2018.01); *Y02A 50/478* (2018.01); *Y02A 50/479* (2018.01); *Y02A 50/481* (2018.01); *Y02A 50/483* (2018.01)

(58) Field of Classification Search
None
See application file for complete search history.

(56) References Cited

U.S. PATENT DOCUMENTS

| | | |
|---|---|---|
| 3,988,411 A | 10/1976 | Capozza |
| 3,989,535 A | 11/1976 | Capozza |
| 4,068,757 A | 1/1978 | Casey |
| 4,195,175 A | 3/1980 | Peniston et al. |
| 4,378,017 A | 3/1983 | Kosugi et al. |
| 4,394,373 A | 7/1983 | Malette et al. |
| 4,532,134 A | 7/1985 | Malette et al. |
| 4,575,519 A | 3/1986 | Kifune et al. |
| 4,605,623 A | 8/1986 | Malette et al. |
| 4,699,135 A | 10/1987 | Motosugi et al. |
| 4,749,620 A | 6/1988 | Rha et al. |
| 4,803,168 A | 2/1989 | Jarvis, Jr. |
| 4,895,724 A | 1/1990 | Cardinal et al. |
| 4,942,129 A | 7/1990 | Goosen et al. |
| 5,008,116 A | 4/1991 | Cahn |
| 5,057,540 A | 10/1991 | Kensil et al. |
| 5,071,977 A | 12/1991 | Cassels et al. |
| 5,093,319 A | 3/1992 | Higham et al. |
| 5,116,747 A | 5/1992 | Moo-Young et al. |
| 5,219,749 A | 6/1993 | Bouriotis et al. |
| 5,229,123 A | 7/1993 | Masubuchi et al. |
| 5,252,468 A | 10/1993 | Fujishima et al. |
| 5,447,505 A | 9/1995 | Valentine et al. |
| 5,457,141 A | 10/1995 | Matsuda et al. |
| 5,510,102 A | 4/1996 | Cochrum |
| 5,529,914 A | 6/1996 | Hubbell et al. |
| 5,541,186 A | 7/1996 | Breu et al. |
| 5,550,110 A | 8/1996 | Cody et al. |
| 5,571,821 A | 11/1996 | Chan et al. |
| 5,573,934 A | 11/1996 | Hubbell et al. |
| 5,622,834 A | 4/1997 | Vournakis et al. |
| 5,623,064 A | 4/1997 | Vournakis et al. |
| 5,624,679 A | 4/1997 | Vournakis et al. |
| 5,635,493 A | 6/1997 | Vournakis et al. |
| 5,641,752 A | 6/1997 | Cody et al. |
| 5,658,943 A | 8/1997 | Berryman et al. |
| 5,686,115 A | 11/1997 | Vournakis et al. |
| 5,731,298 A | 3/1998 | Reinmuller et al. |
| 5,804,594 A | 9/1998 | Murad et al. |
| 5,811,416 A | 9/1998 | Chwalisz et al. |
| 5,846,952 A | 12/1998 | Vournakis et al. |
| 5,858,350 A | 1/1999 | Vournakis et al. |
| 5,871,985 A | 2/1999 | Aebischer et al. |
| 5,916,907 A | 6/1999 | Bird |

(Continued)

FOREIGN PATENT DOCUMENTS

| | | |
|---|---|---|
| CA | 2072395 | 1/1993 |
| DE | 19821598 | 11/1999 |

(Continued)

OTHER PUBLICATIONS

U.S. Appl. No. 09/875,846, filed Jun. 6, 2001, Vournakis et al.

(Continued)

*Primary Examiner* — Robert A Wax
*Assistant Examiner* — Randeep Singh
(74) *Attorney, Agent, or Firm* — Jones Day

(57) ABSTRACT

Described herein are compositions comprising shortened fibers of poly-N-acetylglucosamine and/or a derivative thereof ("sNAG nanofibers") and anti-bacterial applications of such compositions. The sNAG nanofibers may be formulated into compositions for the prevention and/or treatment of bacterial infections and diseases associated with such infections. Regimens employing such compositions are also described.

31 Claims, 27 Drawing Sheets

Figure 1A:
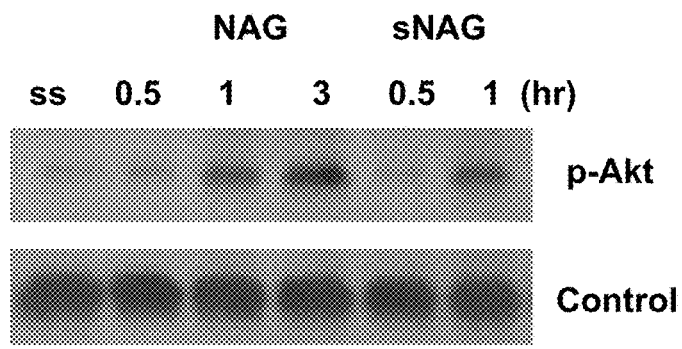

Specification includes a Sequence Listing.

(56) References Cited

U.S. PATENT DOCUMENTS

| | | | |
|---|---|---|---|
| 6,046,179 A | 4/2000 | Murch et al. |
| 6,063,911 A | 5/2000 | Vournakis et al. |
| 6,080,866 A | 6/2000 | Spurr |
| 6,162,241 A | 12/2000 | Coury et al. |
| 6,599,720 B2 | 7/2003 | Vournakis et al. |
| 6,610,668 B2 | 8/2003 | Vournakis et al. |
| 6,630,459 B2 | 10/2003 | Vournakis et al. |
| 6,649,599 B2 | 11/2003 | Vournakis et al. |
| 6,686,342 B2 | 2/2004 | Vournakis et al. |
| 6,743,783 B1 | 6/2004 | Vournakis et al. |
| 6,864,245 B2 | 3/2005 | Vournakis et al. |
| 7,037,983 B2 | 5/2006 | Huang et al. |
| 7,041,657 B2 | 5/2006 | Vournakis et al. |
| 7,115,588 B2 | 10/2006 | Vournakis et al. |
| 7,140,882 B2 | 11/2006 | Ito |
| 7,157,079 B2 | 1/2007 | Nielsen et al. |
| 7,285,266 B2 | 10/2007 | Vournakis et al. |
| 7,307,157 B2 | 12/2007 | Yoshii et al. |
| 7,371,403 B2 | 5/2008 | McCarthy et al. |
| 7,691,832 B2 | 4/2010 | Haty |
| 7,704,522 B2 | 4/2010 | Morgan |
| 7,931,637 B2 | 4/2011 | Vournakis et al. |
| 8,152,750 B2 | 4/2012 | Vournakis et al. |
| 8,481,512 B2 | 7/2013 | Vournakis et al. |
| 8,802,083 B2 | 8/2014 | Vournakis et al. |
| 8,835,408 B2 | 9/2014 | Vournakis et al. |
| 8,858,964 B2 | 10/2014 | Vournakis et al. |
| 8,859,528 B2 | 10/2014 | Vournakis et al. |
| 8,871,247 B2 | 10/2014 | Finkielsztein et al. |
| 8,992,453 B2 | 3/2015 | Vournakis et al. |
| 9,139,663 B2 | 9/2015 | Finkielsztein et al. |
| 9,139,664 B2 | 9/2015 | Finkielsztein et al. |
| 9,198,928 B2 | 12/2015 | Vournakis et al. |
| 9,320,653 B2 | 4/2016 | Vournakis et al. |
| 9,642,871 B2 | 5/2017 | Vournakis et al. |
| 10,206,938 B2 | 2/2019 | Vournakis et al. |
| 2003/0104020 A1 | 6/2003 | Davison et al. |
| 2003/0144347 A1 | 7/2003 | Ryback et al. |
| 2004/0087015 A1 | 5/2004 | Vournakis et al. |
| 2004/0091493 A1 | 5/2004 | Perrier et al. |
| 2004/0243043 A1 | 12/2004 | McCarthy et al. |
| 2004/0254244 A1 | 12/2004 | Kono et al. |
| 2005/0004072 A1 | 1/2005 | Vournakis et al. |
| 2005/0113773 A1 | 5/2005 | Yoshii et al. |
| 2006/0051432 A1 | 3/2006 | Morgan |
| 2006/0105049 A1 | 5/2006 | Fernandes et al. |
| 2006/0172000 A1 | 8/2006 | Cullen et al. |
| 2007/0021703 A1 | 1/2007 | McCarthy |
| 2007/0036846 A1 | 2/2007 | Tsang |
| 2007/0072826 A1 | 3/2007 | Vournakis et al. |
| 2007/0085059 A1 | 4/2007 | Mora-Gutierrez et al. |
| 2007/0093416 A1 | 4/2007 | Igarashi et al. |
| 2007/0105815 A1 | 5/2007 | Vournakis et al. |
| 2007/0237812 A1 | 10/2007 | Patel et al. |
| 2008/0026064 A1 | 1/2008 | Vournakis et al. |
| 2008/0207561 A1 | 8/2008 | Utecht et al. |
| 2008/0299147 A1 | 12/2008 | Dillon et al. |
| 2009/0117175 A1 | 5/2009 | Finkielsztein et al. |
| 2009/0130186 A1 | 5/2009 | McCarthy et al. |
| 2009/0247737 A1 | 10/2009 | Wiley et al. |
| 2009/0247738 A1 | 10/2009 | Vournakis et al. |
| 2009/0318383 A1 | 12/2009 | Vournakis et al. |
| 2010/0016232 A1 | 1/2010 | Kjaer |
| 2010/0021514 A1 | 1/2010 | Fugmann |
| 2010/0040694 A1 | 2/2010 | Na et al. |
| 2010/0086613 A1 | 4/2010 | Wu et al. |
| 2010/0105139 A1 | 4/2010 | Spanjaard et al. |
| 2010/0150960 A1 | 6/2010 | Schlom et al. |
| 2010/0323986 A1 | 12/2010 | Vournakis et al. |
| 2013/0287853 A1 | 10/2013 | Vournakis et al. |
| 2013/0337037 A1 | 12/2013 | Finkielsztein et al. |
| 2014/0051849 A1 | 2/2014 | Finkielsztein et al. |
| 2014/0127310 A1 | 5/2014 | Vournakis et al. |
| 2014/0350449 A1 | 11/2014 | Vournakis et al. |
| 2014/0363673 A1 | 12/2014 | Minami et al. |
| 2015/0024014 A1 | 1/2015 | Finkielsztein et al. |
| 2015/0118281 A1 | 4/2015 | Vournakis et al. |
| 2015/0140045 A1 | 5/2015 | Vournakis et al. |
| 2016/0030465 A1 | 2/2016 | Finkielsztein et al. |
| 2016/0193379 A1 | 7/2016 | Finkielsztein et al. |
| 2017/0128382 A1 | 5/2017 | Vournakis et al. |
| 2017/0304354 A1 | 10/2017 | Vournakis et al. |
| 2018/0099003 A1 | 4/2018 | Vournakis et al. |
| 2018/0360868 A1 | 12/2018 | Finkielsztein et al. |
| 2019/0060348 A1 | 2/2019 | Finkielsztein et al. |

FOREIGN PATENT DOCUMENTS

| | | |
|---|---|---|
| EP | 0392396 | 10/1990 |
| EP | 0426368 | 5/1991 |
| EP | 0543572 | 5/1993 |
| EP | 0544000 | 6/1993 |
| EP | 0731812 | 9/1996 |
| EP | 1139752 | 10/2001 |
| EP | 1306390 | 5/2003 |
| FR | 2 736 835 | 1/1997 |
| GB | 2220211 | 1/1990 |
| GB | 1038367 | 8/1996 |
| JP | 55-152705 | 11/1980 |
| JP | 56-131639 | 10/1981 |
| JP | 56-133344 | 10/1981 |
| JP | 58-088424 | 5/1983 |
| JP | 58-220899 | 12/1983 |
| JP | 60-025003 | 2/1985 |
| JP | 60-208302 | 10/1985 |
| JP | 60-215003 | 10/1985 |
| JP | 61-253065 | 11/1986 |
| JP | 62-288602 | 12/1987 |
| JP | 63-503466 | 12/1988 |
| JP | 01-167301 | 7/1989 |
| JP | 02-006501 | 1/1990 |
| JP | 02-225539 | 9/1990 |
| JP | 02-235905 | 9/1990 |
| JP | 02-240101 | 9/1990 |
| JP | 03-167201 | 7/1991 |
| JP | 03-204812 | 9/1991 |
| JP | 04-041422 | 2/1992 |
| JP | 04-126701 | 4/1992 |
| JP | 04-371161 | 12/1992 |
| JP | 05-025289 | 2/1993 |
| JP | 05-032702 | 2/1993 |
| JP | 05-051465 | 3/1993 |
| JP | 05-502267 | 4/1993 |
| JP | 05-235905 | 9/1993 |
| JP | 05-271094 | 10/1993 |
| JP | 07-102458 | 4/1995 |
| JP | 9506126 | 6/1997 |
| JP | 2002-512195 | 4/2002 |
| JP | 2003-128704 | 5/2003 |
| JP | 2003-160602 | 6/2003 |
| JP | 2004-211101 | 7/2004 |
| JP | 2005-509059 | 4/2005 |
| JP | 2005-281239 | 10/2005 |
| JP | 2006-518764 | 8/2006 |
| JP | 2008-019264 | 1/2008 |
| NZ | 277662 | 4/1998 |
| WO | WO 1987/07618 | 12/1987 |
| WO | WO 92/03480 | 3/1992 |
| WO | WO 1992/04408 | 3/1992 |
| WO | WO 93/08799 | 5/1993 |
| WO | WO 93/09176 | 5/1993 |
| WO | WO 93/12875 | 7/1993 |
| WO | WO 94/03483 | 2/1994 |
| WO | WO 95/15343 | 6/1995 |
| WO | WO 96/11927 | 4/1996 |
| WO | WO 96/19459 | 6/1996 |
| WO | WO 96/39122 | 12/1996 |
| WO | WO 97/08169 | 3/1997 |
| WO | WO 97/37987 | 10/1997 |
| WO | WO 00/36918 | 6/2000 |
| WO | WO 02/063961 | 8/2002 |
| WO | WO 03/042251 | 5/2003 |
| WO | WO 04/024196 | 3/2004 |

(56) References Cited

FOREIGN PATENT DOCUMENTS

| WO | WO 2004/026200 | 4/2004 |
|---|---|---|
| WO | WO 04/060172 | 7/2004 |
| WO | WO 04/076637 | 9/2004 |
| WO | WO 05/027993 | 3/2005 |
| WO | WO 2005/027893 | 3/2005 |
| WO | WO 05/063311 | 7/2005 |
| WO | WO 2006/066752 | 6/2006 |
| WO | WO 2007/059605 | 5/2007 |
| WO | WO 2007/109812 | 9/2007 |
| WO | WO 2007/109813 | 9/2007 |
| WO | WO 2008/048076 | 4/2008 |
| WO | WO 2008/103345 | 8/2008 |
| WO | WO 2009/095456 | 8/2009 |
| WO | WO 2011/130646 | 10/2011 |
| WO | WO 2011/140638 | 11/2011 |
| WO | WO 2012/061803 | 5/2012 |
| WO | WO 2012/142581 | 10/2012 |
| WO | WO 2014/165302 | 10/2014 |

OTHER PUBLICATIONS

Aebischer, P. et al., 1993, "Cell Encapsulation for the Nervous System," in *Fundamentals of Animal Cell Encapsulation and Immobilization*, CRC Press, pp. 197-224.
Andrews et al. 1999, "The role of zinc in wound healing." Adv Wound Care. 12(3):137-8.
ASTM Committee F04 on Medical and Surgical Materials and Devices, 2001, "Designation F2103-01: Standard Guide for Characterization and Testing of Chitosan Salts as Starting Materials Intended for Use in Biomedical and Tissue-Engineered Medical Product Applications," ASTM International, pp. 1-8.
Austin, P.R. and Sennett, S., 1986, "Dry Chitosan Salts and Complexes of Aliphatic Carboxylic Acids," in *Chitin in Nature and Technology*, Muzzarelli et al., eds., Plenum Press, New York, pp. 279-286.
Azuma, 2012, "alpha-Chitin Nanofibrils Improve Inflammatory and Fibrosis Responses in Inflmmatory Bowel Disease Mice Model," Carbohydrate Polymers 90:197-200.
Azuma, 2012, "Beneficial and Preventive Effect of Chitin Nanofibrils in a Dextran Sulfate Sodium-induced Acute Ulcerative Colitis Model," Carbohydrate Polymers 87:1399-1403.
Barbosa et al., 2010, "Evaluation of the effect of the degree of acetylation on the inflammatory response to 3D porous chitosan scaffolds," J Biomed Mater Res A. 93(1):20-28.
Battistini, B. et al., 1993, "Growth Regulatory Properties of Endothelins," Peptides, 14:385-399.
Beauman, J.G. et al., 2005, "Genital herpes: a review," Am Fam Physician, 72(8):1527-34.
Bell, K.M. et al., 1995, "Effect of Endothelin-1 and Sarafotoxin S6c on Blood Flow in a Rat Tumor," J. Cardiovasc. Pharmacol., 26(Suppl. 3):S222-S225.
Berkeley, R.C.W. et al., 1979, "Chitin, Chitosan and their Degradative Enzymes," in Microbial Polysaccharides and Polysaccharases, Berkeley et al., eds., Academic Press, pp. 205-216.
Bissett, 2006, "Glucosamine: an Ingredient with Skin and Other Benefits," J. Cosm. Dermatol. 5:309-315.
Blackwell, J. et al., 1967, "Chitin Fibers of the Diatoms Thalassiosira fluviatilis and Cyclotella cryptica," J. Mol. Biol., 28:383-385.
Blackwell, J., 1988, "Physical Methods for the Determination of Chitin Structure and Conformation," Meth. Enz., 161:435-442.
Bodmeier, R. et al., 1989, "A Novel Approach to the Oral Delivery of Micro- or Nanoparticles," Pharm. Res., 6(5):413-417.
Carreno-Gomez, B. & Duncan, R., 1997, "Evaluation of the Biological Properties of Soluble Chitosan and Chitosan Microspheres," Int. J. Pharma., 148:231-240.
Chhabra, 2004, "Antimicrobial and antioxidant properties of chitosan," Thesis Submitted to the Graduate Faculty of the University of Georgia for Master of Science Degree, Athens, Georgia.

Choi, W.S. et al., 2002, "Preparation of Chitosan Oligomers by Irradiation," Polym. Degrad. Stab., 78:533-538.
Clozel, M. et al., 1994, "Pharmacological Characterization of Bosentan, a New Potent Orally Active Nonpeptide Endothelin Receptor Antagonist," J. Pharmacol. Exp. Ther., 270(1): 228-235.
Dai et al., 2009, "Chitosan acetate bandage as a topical antimicrobial dressing for infected burns," Antimicrobial Agents and Chemotherapy, 53(2):393-400.
Davis, M. and Preston, J.F., 1981, "A Simple Modified Carbodiimide Method for Conjugation of Small Molecular Weight Compounds to Immunoglobulin G with Minimal Protein Crosslinking," Anal. Biochem. 116:402-407.
Diaz-Visurraga et al., 2010, "Lethal effect of chitosan-Ag (I) films on *Staphylococcus aureus* as evaluated by electron microscopy," J Applied Microbiol. 108:633-646.
Ding et al., 2014, "Emerging Chitin and Chitosan Nanofibrous Materials for Biomedical Applications," Nanoscale 6:9477-9493.
Domard, A., 1986, "Circular Dichroism Study on N-acetylglucosamine Oligomers," Int. J. Macromol. 8:243-246.
Dong, C. and Rogers, J.A., 1991, "Polymer-coated Liposomes: Stability and Release of ASA from Carboxymethyl Chitin Coated Liposomes," Journal of Controlled Release 17:217-224.
European Search Report for EP Application No. EP 12153634.6, dated Jun. 15, 2012.
Falk, M. et. al., 1966, "Studies on Chitin ($\beta$-(1-4)-linked 2-acetamido-2-deoxy-D-glucan) Fibers of the Diatom Thalassiosira fluviatilis hustedt," Can. J. Chem. 44: 2269-2281.
Fine et al., 1991, "Revised Clinical and Laboratory Criteria for Subtypes of Inherited Epidermolysis Bullosa: A Consensus Report by the Subcommittee on Diagnosis and Classification of the National Epidermolysis Bullosa Registry," Journal of the American Academy of Dermatology, 24(1):119-35.
Fischer et al., 2004, "Comparison of Structural and Hemostatic Properties of the Poly-N-Acetyl Glucosamine Syvek Patch with Products Containing Chitosan," Microsc. Res. Tech. 63:168-174.
Fischer et al., 2005, "Synergistic Platelet Integrin Signaling and Factor XII activation in poly-N-acetyl Glucosamine Fiber-mediated hemostasis," Biomaterials 26:5433-5443.
Fischer et al., 2007, "Hemostatic Properties of Glucosamine-based Materials," Journal of Biomedical Materials Research 80A: 167-174.
Fujimoto et al., 2006, "Antibacterial effects of Chitosan solution® against Legionella neumophila, *Escherichia coli*, and *Staphylococcus aureus*," Intl J Food Microbiol. 112:96-101.
Gomez-Garre, D. et al., 1996, "An Orally Active $ET_A/ET_B$ Receptor Antagonist Ameliorates Proteinuria and Glomerular Lesions in Rats with Proliferative Nephritis," Kidney Intl. 50:962-972.
Goodwin, A.T. et al., 1998, "Role of Endogenous Endothelin in the Regulation of Basal Coronary Tone in the Rat," J. Physiol. 511(2):549-557.
Groboillot, A.F. et al., 1993, "Membrane Formation by Interfacial Cross-linking of Chitosan for Microencapsulation of *Lactococcus lactis*," Biotech. and Bioeng. 42(10):1157-1163.
Halaban, R., 1996, "Growth Factors and Melanomas," Seminars in Oncology 23:673-681.
Hama et al., 2006, "Quantitative comparison of intracellular trafficking and nuclear transcription between adenoviral and lipoplex systems," Mol Ther. 13(4):786-94.
Harrington et al., 2002, "Cells as vehicles for cancer gene therapy: the missing link between targeted vectors and systemic delivery?" Hum Gene Ther. 13(11):1263-80.
Harrington et al., 2002, "Recombinant vaccinia virus-induced T-cell immunity: quantitation of the response to the virus vector and the foreign epitope," J Virol. 76(7):3329-37.
Hazrati et al., 2006, "Human A- and B-Defensins Block Multiple Sifts in Herpes Simplex Virus Infection," J Immunol, 177:8658-8666.
Hirano, S. et al., 1976, "Selective N-acylation of Chitosan," Carbohydrate Research 47:315-320.
Hirano, S. et al., 1981, "SEM Ultrastructure Studies of N-acyl- and N-benzylidene-chitosan and Chitosan Membranes," J. Biomed. Mat. Res. 15:903-911.

(56) References Cited

OTHER PUBLICATIONS

Hirano, S. et al., 1990, "The Regulation of Serum Cholesterol Level by Oral Administration of Chitosan in Rabbits," Proceedings of The International Symposium of Chitin Derivatives in Life Sciences, Oct. 5-7, pp. 115-120.
Hirano, S., 1989, "Production and Application of Chitin and Chitosan in Japan," in Chitin and Chitosan, Skjak-Braek, Anthosen, and Sanford, eds. Elsevier Science Publishing Co., pp. 37-43.
Hirsch et al., 2009, "Human beta-defensin-3 promotes wound healing in infected diabetic wounds," J Gene Med. 11(3):220-228.
Hocher, B. et al., 1997, "The Paracrine Endothelial System: Pathophysiology and Implications in Clinical Medicine," Eur. J. Chem. Clin. Biochem. 35:175-189.
Howell, et al., 2007, "Antiviral Activity of Human Beta-defensin 3 against vaccinia virus," J. Allergy and Clini. Immuno. 119(4):1022-25.
Huang, Y.C. et al., 2005, "Pulmonary Inflammation Caused by Chitosan Microparticles," J. Biomed. Mater. Res. Part A 75(2):283-287.
Hwang, C. et al., 1985, "Encapsulation with Chitosan: Transmembrane Diffusion of Proteins in Capsules," in Chitin in Nature and Technology, Muzzareli, R. et al., eds., Plenum Press, pp. 389-396.
IBA Industrial, 2007, "IBA Solutions In Cancer Diagnosis, Therapy. Sterilization and Ionization Solutions for Hygiene and Safety. Material Applications," retrieved Feb. 7, 2007 from: http://www.iba-worldwide.com/industrial/applications/material/index.php.
International Preliminary Report of Patentability of International Application No. PCT/US2011/032709 (published as WO 2011/130646), dated Oct. 26, 2012.
International Search Report for International App. No. PCT/US2008/002172 (published as WO 2008/103345), dated Aug. 7, 2009.
International Search Report for International App. No. PCT/US2011/032709 (published as WO 2011/130646), dated Aug. 15, 2011.
International Search Report for International App. No. PCT/US2012/033782 (published as WO 2012/142581), dated Aug. 20, 2012.
International Search Report for International App. No. PCT/US2014/025623 (published as WO 2014/165302), dated Jul. 10, 2014.
Ishihara, M. et al., 2002, "Photocrosslinkable Chitosan as a Dressing for Wound Occlusion and Accelerator in Healing Process," Biomaterials 23:833-840.
Jiang, Y. et al., 2009, "Expression of mouse beta-defensin-3 in MDCK cells and its anti-influenza-virus activity," Arch Virol. 154(4):639-47.
Johnson, R.S. et al, 1992, "In Vivo Tissue Response to Implanted Chitosan Glutamate," in Advances in Chitin and Chitosan, Brine, C.J. et al., eds., Elsevier Publishers, Ltd., pp. 3-8.
Kazakos et al., 2007, European Society of Clinical Microbiology and Infectious Diseases 'Activity of human beta-defensin 3 against metallo-beta-lactamase-producing Pseudomonas aeruginosa strains' [online] [retrieved on Sep. 12, 2013]. Retrieved from the Internet <URL: http://www.blackwellpublishing.com/eccmid17/abstractasp?id=56248>.
Kenny, B. et al., 1997, "Pharmacological Options in the Treatment of Benign Prostatic Hyperplasia," J. Medicinal Chem. 40:1293-1315.
Kikuchi, K. et al., 1996, "Decreased $ET_B$ Receptor Expression in Human Metastatic Melanoma Cells," Biochem. Biophys. Res. Comm. 219:734-739.
Kim et al., 2000, "Modulation of Antigen-Specific Humoral Responses in Rhesus Macaques by Using Cytokine cDNAs as DNA Vaccine Adjuvants," J Virol, 74(7):3427-9.
Klokkevold et al., 1999, "The Effect of Chitosan (poly-N-Acetyl Glucosamine) on Lingual Hemostasis in Heparanized Rabbits," J Oral Maxillofac Surg 57:49-52.
Komai, T. et al., 1986, "Biomedical Evaluation of Acylated Chitins as Coating Materials," in Chitin in Nature and Technology, Muzzarelli et al., eds., Plenum Press, New York, pp. 497-506.

Kurita, K. and Inoue, S., 1989, "Preparation of Indo-chitins and Graft Copolymerization onto the Derivatives," in Chitin and Chitosan, Skjak-Braek et al, Elsevier Science Publishing Co., Inc., pp. 365-372.
Kurita, K. et al., 1990, "Preparations of Soluble Chitin Derivatives and the Modifications to Branched Chitins," Polym. Prep. (Am. Chem. Soc., Div. Polym. Chem.) 31:624-625.
Lindner et al., 2011, "Anti-bacterial effects of poly-N-acetyl-glucosamine nanofibers in cutaneous wound healing: requirement for Akt1," PLoS ONE 6(4):E18996. DOI: 10.1371/JOURNAL.PONE.0018996.
Lindner et al., 2015, "pG1cNAc Nanofiber Treatment of Cutaneous Wounds Stimulate Increased Tensile Strength and Reduced Scarring via Activation of Akt1," PLoS One 10(5): e0127876. DOI: 10.1371/journal.pone.0127876.
Liu et al., 2001, "Antibacterial action of chitosan and carboxymethylated chitosan," Journal of Applied Polymer Science 79:1324-1335.
Liu et al., 2004, "Chitosan kills bacteria through cell membrane damage," Intl J Food Microbiol. 95:147-155.
Lundblad, R. et al., 1996, "Granulocyte Colony-Stimulating Factor Improves Survival Rate and Reduces Concentrations of Bacteria, Endotoxin, Tumor Necrosis Factor, and Endothelin-1 in Fulminant Intra-Abdominal Sepsis in Rats," Crit. Care Med. 24:820-826.
Lüscher, T.F. and Wenzel, R.R., 1995, "Endothelin and Endothelin Antagonists: Pharmacology and Clinical Implications," in Mediators in the Cardiovascular System: Regional Ischemia, Birkhäuser Verlag, Basel, Switzerland, pp. 237-253.
Mann, M. et al., 2006, "Unsaturated N-Acetyl-D-Glucosaminuronic Acid Glycosides As Inhibitors Of Influenza Virus Sialidase," Glycoconj J. 23(1-2):127-33.
Mao et al., 2001, "Chitosan-DNA nanoparticles as gene carriers: synthesis, characterization and transfection efficiency," J Control Release 70(3):399-421.
Maresch, G. et al., 1989, "Hydroxypropylation of Chitosan," in Chitin and Chitosan, Skjak-Braek, Anthosen, and Sanford, eds., Elsevier Science Publishing Co., pp. 389-395.
Markewitz, B.A. et al., 1995, "Endothelin-1 Synthesis, Receptors, and Signal Transduction in Alveolar Epithelium: Evidence for an Autocrine Role," Am. J. Physiol. 268:L192-L200.
Mateo, A.O. and De Artiñano, M.A., 1997, "Highlights on Endothelins: A Review," Pharmacol. Res. 36(5):339-351.
Matsuhashi, S. and Kume, T., 1997, "Enhancement of Antimicrobial Activity of Chitosan By Irradiation," J. Sci. Food Agric. 73:237-241.
Matthew, H.W. et al., 1993, "Complex Coacervate Microcapsules for Mammalian Cell Culture and Artificial Organ Development," BioTechnol. Prog. 9(5):510-519.
McCurdy, J.D., 1992, "FDA and the Use of Chitin and Chitosan Derivatives," in Advances in Chitin and Chitosan, Brine, C.J. et al., eds., Elsevier Publishers, Ltd., pp. 659-662.
McLachlan and Craigne, 1966, "Chitin Fibers in Cyclotella clyptica and Growth of C. cryptica and Thalassiosira fluviatilis," Some Contemp. Stud. Mar. Sci., pp. 511-517.
McLachlan, A.G. et al., 1965, "Studies on the Chitin (chitin: poly-N-acetylglucosamine) Fibers of the Diatom Thalassiosira fluviatilis hustedt," Can. J. Botany 43:707-713.
Mezzana, 2008, "Clinical Efficacy of a New Chitin Nanofibrils-based Gel in Wound Healing," Acta Chirurgiae Plasticae 50(3):81-84.
Middleton, J.C. and Tipton, A.J., 1998, "Materials: Synthetic Biodegradable Polymers as Medical Devices," retrieved Feb. 7, 2007 from: http://www.devicelink.com/mpb/archive/98/03/002.html.
Min, B.M. et al., 2004, "Chitin and Chitosan Nanofibers: Electrospinning of Chitin and Deacetylation of Chitin Nanofibers," Polymer 45:7137-7142.
Minami, S. et al., 1996, "Chitosan-Inducing Hemorrhagic Pneumonia in Dogs," Carb. Polymers. 29:241-246.
Mireles, C. et al., 1992, "Complex Formation of Chitosan and Naturally Occurring Polyanion," in Advances in Chitin and Chitosan, Brine, C.J. et al., eds., Elsevier Publishers, Ltd., pp. 506-515.
Moraitis, S. et al., 1997, "Endothelin Expression and Responsiveness in Human Ovarian Carcinoma Cell Lines," Eur. J. Cancer 33:661-668.

(56) References Cited

OTHER PUBLICATIONS

Morbidelli, L. et al., 1995, "Proliferation and Migration of Endothelial Cells is Promoted by Endothelins via Activation of $ET_B$ Receptors," Am. J. Physiol. 269:H686-H695.
Morganti & Morganti, 2008, "Chitin Nanofibrils for Advanced Cosmeceuticals," Clinics in Dermatology 26:334-340.
Morganti et al., 2011, "Transforming Nanostructured Chitin from Crustacean Waste into Beneficial Health Products: a Must for our Society," Nanotechnology, Science and Applications 4:123-129.
Nelson, J.B. et al., 1996, "Endothelin-1 Production and Decreased Endothelin B Receptor Expression in Advanced Prostate Cancer," Cancer Res. 56:663-668.
Nishi, N. et al., 1986, "Preparation and Characterization of Phosphorylated Chitin and Chitosan," in *Chitin in Nature and Technology*, Muzzarelli et al., Plenum Press, New York, pp. 297-299.
No et al., 2002, "Antibacterial Activity of Chitosans and Chitosan Oligomers with Different Molecular Weights," Intl J Food Microbiol. 74:65-72.
Noguchi, J. et al., 1969, "Chitosan Epichlorohydrin Anion Exchange Resin with Primary Amines as Absorption Site," Kogyo Kagaku Zasshi 72:796-799.
Notice of Allowance issued in U.S. Appl. No. 13/956,012 dated May 18, 2015.
Notice of Allowance issued in U.S. Appl. No. 13/956,035 dated May 18, 2015.
Notice of Allowance dated Dec. 29, 2015 issued in U.S. Appl. No. 14/459,044.
Obara, K. et al., 2005, "Acceleration of Wound Healing in Healing-Impaired db/db Mice with a Photocrosslinkable Chitosan Hydrogel Containing Fibroblast Growth Factor-2," Wound Repair Regen. 13(4):390-397.
Office Action dated Apr. 2, 2013 issued in U.S. Appl. No. 13/641,015 (now U.S. Pat. No. 8,858,964).
Office Action dated Aug. 30, 2011 issued in U.S. Appl. No. 12/033,670 (now U.S. Pat. No. 8,871,247).
Office Action dated Dec. 6, 2010 issued in U.S. Appl. No. 12/033,670 (now U.S. Pat. No. 8,871,247).
Office Action dated Feb. 25, 2015 issued in U.S. Appl. No. 14/327,192 (now U.S. Pat. No. 9,198,928).
Office Action dated Sep. 17, 2014 issued in U.S. Appl. No. 13/956,012 (now U.S. Pat. No. 9,139,663).
Office Action dated Sep. 18, 2014 issued in U.S. Appl. No. 13/956,035 (now U.S. Pat. No. 9,139,664).
Ohlstein, E.H. et al., 1996, "Endothelin Receptors: Receptor Classification, Novel Receptor Antagonists, and Potential Therapeutic Targets," Medicinal Res. Rev. 16:365-390.
Oikawa, T. et al., 1994, "Production of Endothelin-1 and Thrombomodulin by Human Pancreatic Cancer Cells," Br. J. Cancer 69:1059-1064.
Parris, R.J. and Webb, D.L., 1997, "The Endothelin System in Cardiovascular Physiology and Pathophysiology," Vascular Med. 2:31-43.
Patel, K.V. and Schrey, M.P., 1995, "Human Breast Cancer Cells Contain a Phosphoramidon-Sensitive Metalloproteinase which Can Process Exogenous Big Endothelin-1 to Endothelin-1: A Proposed Mitogen for Human Breast Fibroblasts," Brit. J. Cancer 71:442-447.
Paul, W. and Sharma, C.P., 2004, "Chitosan and Aiginate Wound Dressings: A Short Review," Trends Biomater. Artif. Organs 18(1):18-23.
Perkins et al., 2010, "Poly-N-acetylglucosamine nanofibers from a marine diatom promote wound healing and defensin expression in an AKT1-dependent manner," Abstracts of Papers American Chemical Society 239:527.
Pietramaggiori et al., 2008, "Effects of poly-N-acetyl glucosamine (pGlcNAc) patch on wound healing in db/db mouse," The Journal of Trauma Injury, Infection, and Critical Care 64(3):803-808.
Polk, A. et al., 1994, "Controlled Release of Albumin from Chitosan-alginate Microcapsules," J. Pharma. Sci. 83(2):178-185.

Rabea et al., 2003, "Chitosan as antimicrobial agent: applications and mode of action," BioMacromolecules, American Chemical Society 4(6):1457-1465.
Reid, K. et al., 1996, "Multiple Roles for Endothelin in Melanocyte Development: Regulation of Progenitor Number and Stimulation of Differentiation," Development 122:3911-3919.
Rosiak, J. et al., 1992, "Radiation Sterilization of Chitosan Sealant for Vascular Prostheses," J. Radioan. and Nucl. Chem. 159(1):87-96.
Roux, S. et al., 1997, "Ro 61-1790, a New Hydrosoluble Endothelin Antagonist: General Pharmacology and Effects on Experimental Cerebral Vasospasm," J. Pharm. Exp. Ther. 283(3):1110-1118.
Sangui Biotech Witten, 2004, "New Wounds Pads Based on Chitosan and Chitosan-Glucan-Complex," SanguiBioTech GmbH, pp. 1-5.
Scherer et al., 2009, "Poly-N-Acetyl glucosamine nanofibers," Annals of Surgery 250(2):322-330.
Schorigin, P. and Hait, E., 1934, "Über die Nitrierung von Chitin," Chem. Ber. 67:1712-1714.
Schweiger, R.G., 1972, "Polysaccharide Sulfates I. Cellulose Sulfate with a High Degree of Substitution," Carbohydrate Res. 21:219-228.
Shichiri, M. et al., 1991, "Endothelin-1 is an Autocrine/Paracrine Growth Factor for Human Cancer Cell Lines," J. Clin. Invest. 87:1867-1871.
Shirley et al., 2001, "Ehlers-Danlos Syndrome in Orthopaedics," Sports Health, 4(5):394-403.
Staros, J.V. et al., 1986, "Enhancement by N-hydroxysulfosuccinate of Water Soluble Carbodiimide Mediated Coupling Reactions," Anal. Biochem. 156:220-222.
Steen et al., 2001, "Improvement in Skin Thickening in Systemic Sclerosis Associated with Improved Survival," Arthritis & Rheumatism, 44(12):2828-35.
Supplementary European Search Report for European Application No. 11769676.5-1453, dated Sep. 25, 2013.
Supplementary European Search Report for European Application No. 12771138, dated Oct. 1, 2014.
Suzuki, N. et al., 1989, "Production of Endothelin-1 and Big-Endothelin-1 by Tumor Cells with Epithelial-Like Morphology," J. Biochem. 106:736-741.
Tanaka, Y. et al., 1997, "Effects of Chitin and Chitosan Particles on BALB/c Mice by Oral and Parenteral Administration," Biomaterials 18(8):591-595.
Technical Insights, Inc., 1989, "Barriers to Commercialization," Ch. 4 in *Chitin and Chitosan: Specialty Biopolymers for Foods, Medicine, and Industry*, Technical Insights, Inc., Ft. Lee, NJ.
Thanoo, B.C. et al., 1992, "Cross-linked Chitosan Microspheres: Preparation and Evaluation as a Matrix for the Controlled Release of Pharmaceuticals," J. Pharm. Pharmacol. 44:283-286.
Tokura, S., et al., 1983, "Studies on Chitin VIII. Some properties of Water Soluble Chitin Derivatives," Polym. J. 15:485-489.
TSI Mason Laboratories, 1995, "Efficacy Study of a Test Article in Preventing Peritoneal Adhesion in Sprague-Dawley Rats," Final Report Amendment Supplement to the Final Report, Study No. 2-T35.
US Pharmacopeia XXII, 1990, pp. 1415-1497.
US Pharmacopeia XXII, 1990, pp. 1497-1500.
US Pharmacopeia XXII, 1991, Suppl. 5, pp. 2702-2703.
US Pharmacopeia XXVIII, 2004, "The Biocompatibility of Materials Used in Drug Containers," General Information, pp. 2529-2536.
Vahouny, G.V., 1983, "Comparative Effects of Chitosan and Cholestyramine on Lymphatic Absorption of Lipids in the Rat," Am. J. Clin. Nutr. 38(2):278-284.
Vandevord, P.J. et al., 2003, "The Long-term Immune Response to Chitosan Scaffolds," Society for Biomaterials 29th Annual Meeting Transactions, p. 165.
Vasconcelos et al., 2013, "Macrophage polarization following chitosan implantation. Biomaterials," 34(38):9952-9959.
Veleirinho et al., 2014, "Foreign body reaction associated with PET and PET/chitosan electrospun nanofibrous abdominal meshes," PLoS One. 9(4):e95293.

(56) References Cited

OTHER PUBLICATIONS

Vournakis, J.N. et al., 1994, "Isolation & Characterization of Pure Poly-N-acetylglucosamine: Controlled Enzymatic Deacetylation and Formulation for Tissue Engineering Applications," J Cell Biochem. Suppl. O(18C): 283 (Abstract PZ 313), Keystone Symposium on Tissue Engineering.

Vournakis, J.N. et al., 2008, "Poly-N-acetyl glucosamine nanofibers regulate endothelial cell movement and angiogenesis: dependency on integrin activation of Etsl," J Vasc Res. 45(3):222-32.

Waknine, Y., 2005, "International Approvals: Taxus Express(2), Nexstent, Chitoskin," retrieved on Feb. 12, 2007 from: http://www.medscape.com/viewarticle/503573.

Webb, M.L. and Meek, T.D., 1997, "Inhibitors of Endothelin," Medicinal Res. Rev. 17:17-67.

Weiner, M.L., 1992, "An Overview of the Regulatory Status and of the Safety of Chitin and Chitosan as Food and Pharmarceutical Ingredients," in *Advances in Chitin and Chitosan*, Brine, C.J. et al., eds., Elsevier Publishers, Ltd., pp. 663-670.

Wollina, U. et al., 2003, "Functional Textiles In Prevention of Chronic Wounds, Wound Healing and Tissue Engineering," *Textiles and the Skin. Curr. Probl. Dermatol.*, Elsner et al., eds., Basel, Karger, 31:82-97.

Written Opinion for International App. No. PCT/US2011/032709 (published as WO 2011/130646), dated Aug. 15, 2011.

Written Opinion for International App. No. PCT/US2012/033782 (published as WO 2012/142581), dated Aug. 20, 2012.

Written Opinion for International App. No. PCT/US2014/025623 (published as WO 2014/165302), dated Jul. 10, 2014.

Written Opinion of the International Searching Authority for International App. No. PCT/US2008/002172 (published as WO 2008/103345), dated Aug. 7, 2009.

Wu et al., 2005, "High efficient fabrication micropowder by combination of gamma radiation and jet pulverization," Carbohydrate Polymers, 60:61-5.

Yamamoto, A. et al., 2003, "Microfabrication of a Biodegradable Polymer By Ion Beam Irradiation For a New Co-Culture System of Cells," Eur. Cells Mater. 6(Suppl. 1): 77.

Yamashita, J. et al., 1991, "A Large Amount of Endothelin-1 is Present in Human Breast Cancer Tissues," Res. Comm. Chem. Pathol. Pharmacol. 74:363-369.

Yanagisawa, M. et al., 1988, "A Novel Potent Vasoconstrictor Peptide Produced by Vascular Endothelial Cells," Nature 332:411-415.

Yang, F. et al., 2002, "Performance Modification of Chitosan Membranes Induced By Gamma Irradiation," J. Biomater. Appl. 16:215-226.

Yasin, B. et al., 2004, "Theta defensins protect cells from infection by herpes simplex virus by inhibiting viral adhesion and entry," J Virol. 78(10):5147-56.

Yeo, Y. et al., 2006, "Peritoneal Application of Chitosan and UV-cross-linkable Chitosan," J. Biomed. Mater. Res. 78A:668-675.

Yohn, J.J. et al. 1994, "Human Melanoma Cells Express Functional Endothelin-1 Receptors," Biochem. Biophys. Res. Comm. 201:449-457.

Yoksan, R. et al., 2004, "γ-Ray Irradiation Practical Conditions for Low Molecular Weight Chitosan Material Production," Mat. Res. Soc. Symp. Proc. 792:R5.10.1-R5.10.6.

Yoshioka, T. et al., 1990, "Encapsulation of Mammalian Cell with Chitosan-CMC Capsule," Biotechnol. Bioeng. 35:66-72.

Zheng et al., 2003, "Study on antimicrobial activity of chitosan with different molecular weights," Carbohydrate Polymers 54:527-530.

Ziche, M. et al., 1995, "$ET_B$ Receptors Promote Proliferation and Migration of Endothelial Cells," J. Cardiovasc. Pharmacol. 26 (Suppl. 3):S284-S286.

Zielinski, B.A. and Aebischer, P., 1994, "Chitosan as a Matrix for Mammalian Cell Encapsulation," Biomaterials 15(13):1049-1056.

Office Action dated May 31, 2016 issued in Chinese Application No. 201280029555.8 (English translation provided by Chinese counsel).

Pan et al., 2006, Medical Immunology, Zhejiang University Press p. 163 (cited in Office Action dated May 31, 2016 issued in Chinese Application No. 201280029555.8 which is cited herein as Reference C165).

Harmenberg et al., 2010, "Prevention of Ulcerative Lesions by Episodic Treatment of Recurrent Herpes Labialis: A Literature Review," Acta. Derm. Venereol 90:122-130.

Nagatani et al., 2008, "739 Oral Chitin Administration Ameliorates Chronic Colitis in TCRα Knockout Mice By Upregulating IFN-Production and Downregulating Chitinase 3-Like-1 Expression in Mucosal Tissues," Gastroenterology 134: A-106.

Spruance et al., 1992, "The Natural History of Recurrent Oral-Facial Herpes Simplex Virus Infection," Seminars in Dermatology 11(3):200-206.

Azuma, 2014, "Preparation and Biomedical Applications of Chitin and Chitosan Nanofibers," J. Biomed. Nanotechnol., 10(10): 2891.

Azuma, 2015, "Anti-inflammatory effects of orally administered glucosamine oligomer in an experimental model of inflammatory bowel disease," Carbohydrate Polymers, 115:448-456.

Azuma, 2015, "Anticancer and Anti-Inflammatory Properties of Chitin and Chitosan Oligosaccharides," J. Funct. Biomater., 6:33-49.

Barouch et al., 2003, "Viral escape from dominant Simian Immunodeficiency Virus epitope-specific cytotoxic T lymphocytes in DNA-vaccinated rhesus monkeys," J Virol. 77(13):7367-75.

Chen et al., 2004, "Transfection of mEpo gene to intestinal epithelium in vivo mediated by oral delivery of chitosan-DNA nanoparticles", World J. Gastroenterol. 10(1):112-116.

Cho et al., Biomaterials, 1999, "Water-soluble chitin as a wound healing accelerator", Biomaterials, 20(22):2139-2145.

Cole et al., 1997, "Characterization of a sustained-release delivery system for combined cytokine/peptide vaccination using a poly-N-acetyl glucosamine-based polymer mix", Clin. Cancer Res., 3(6):867-873.

Fischer et al., 2008, "Non-classical processes in surface hemostasis: mechanisms for the poly-N-acetyl glucosamine-induced alteration of red blood cell morphology and surface prothrombogenicity", Biomed Mater., 3(1):015009.

Forrest and Pack, 2002, "On the kinetics of polyplex endocytic trafficking: implications for gene delivery vector design," Mol Ther. 6(1):57-66.

Fulco et al., 2015, "Poly-N-glucosamine nanofibers for negative-pressure wound therapies", Wound Repair Regen., 23(2): 197-202.

Gorapalli et al., 2012, "Evaluation of a novel poly N-acetyl glucosamine (pG1cNAc) hydrogel for treatment of the degenerating intervertebral disc", Life Sci., 91(25-26):1328-1335.

Jayakumar et al., 2011, "Biomaterials based on chitin and chitosan in wound dressing applications", Biotechnol. Adv., 29:322-337.

Jean et al., 2009, "Chitosan-plasmid nanoparticle formulations for IM and SC delivery of recombinant GFG-2 and PDGF-BB or generation of antibodies," Gene Therapy, 16: 1097-1110.

Kang et al., 2005, "Arterial embolization using poly-N-acetyl glucosamine gel in a rat kidney model", Anat Rec A, 284A:454-459.

Leff 1998, "DNA motif gooses immune antigenicity response in mice CpG outstrips classic vaccine adjuvant 5-Fold; clinical trial to begin shortly," Bioworld Today 9(214).

Mansouri et al., 2004, "Chitosan-DNA nanoparticles as non-viral vectors in gene therapy: strategies to improve transfection efficacy," Eur J Pharm Biopharm. 57(1):1-8.

Muise-Helmericks et al., 2011, "Poly-N-acetyl glucosamine fibers activate bone regeneration in a rabbit femur injury model", J Trauma, 71(2 Suppl 1):S194-6.

Muzyczka, 1992, "Use of adeno-associated virus as a general transduction vector for mammalian cells," Curr. Top. Microbiol. Immunol. 158:97-129.

Muzzarelli et al., 1999, "Biochemistry, histology and clinical uses of chitins and chitosans in wound healing", Chitin and Chitinases:251-264.

Nakamura et al., J. Oral Biosci, 2007, "Nicotine increases expression of beta defensin", vol. 49, Suppl., p. 135, P-105 (English translation provided).

(56) References Cited

OTHER PUBLICATIONS

Neurath, 2017, "Current and emerging therapeutic targets for IBD", Nature Reviews, vol. 14: 269-278.
Nuss et al., 2017, "Poly-N-Acetyl Glucosamine (sNAG) Enhances Early Rotator Cuff Tendon Healing in a Rat Model", Ann Biom Eng., 45(12):2826-2836.
Premenko-Lanier et al., 2003, "DNA vaccination of infants in the presence of maternal antibody: a measles model in the primate," Virology 307(1):67-75.
Ramírez et al., 2000, "Attenuated modified vaccinia virus Ankara can be used as an immunizing agent under conditions of preexisting immunity to the vector," J Virol. 74(16):7651-5.
Ramírez et al., 2000, "Biology of attenuated modified vaccinia virus Ankara recombinant vector in mice: virus fate and activation of B- and T-cell immune responses in comparison with the Western Reserve strain and advantages as a vaccine," J Virol. 74(2):923-33.
Salem et al., 2004, "Paracrine release of IL-12 stimulates IFN-gamma production and dramatically enhances the antigen-specific T cell response after vaccination with a novel peptide-based cancer vaccine," J Immunol. 172(9):5159-67.
Salem et al., 2006, "Novel nonviral delivery approaches for interleukin-12 protein and gene systems: curbing toxicity and enhancing adjuvant activity," J Interferon Cytokine Res. 26(9):593-608.
Salem et al., 2008, "TH1/TH2 Cytokine Fingerprinting for Probing Diseases: From the Bench to the Clinic," J. Med. Sci. 1(2):61-67.
Salem et al., 2010, "Using poly-N-acetyl glucosamine gel matrix to deliver IL-12 with anti-schistosomasis vaccination", J. Infect Dev Countries, 4(5):318-328.
Salem et al., 2010, "Poly-N-acetyl glucosamine gel matrix as a non-viral delivery vector for DNA-based vaccination," Anticancer Res. 30(10):3889-3894.
Salem et al., 2014, "Immunomodulatory effects of IL-12 released from poly-N-acetyl glucosamine gel matrix during schistosomiasis infection", Cytotechnology, 66(4):667-675.
Schlee et al., 2008, "Probiotic Lactobacilli and VSL#3 induce enterocyte beta-defensin 2", Clinical and Experimental Immunology, 151(3): 528-535.
Stoute et al., 1997, "A preliminary evaluation of a recombinant circumsporozoite protein vaccine against Plasmodium falciparum malaria RTS.S Malaria Vaccine Evaluation Group." N Engl J Med. 336(2):86-91.
Tewary et al., 2005, "A heterologous prime-boost vaccination regimen using ORFF DNA and recombinant ORFF protein confers protective immunity against experimental visceral leishmaniasis," J Infect Dis. 191(12):2130-7.
Thatte et al., 2004, "Poly-N-Acetyl Glucosamine-Mediated Red Blood Cell Interactions," J. Trauma 57:S7-S12.
Varmus, 1988, "Retroviruses," Science 240(4858):1427-35.
Vournakis et al., 2004, "Isolation, purification, and characterization of poly-N-acetyl glucosamine use as a hemostatic agent," J Trauma 57(1 Suppl):52-6.
Wang, 2007, "Transport and Delivery System for Medicament", China Medical Science Press, p. 95.
Wasungu and Hoekstra, 2006, "Cationic lipids, lipoplexes and intracellular delivery of genes," J Control Release 116(2):255-64.
Wasungu et al., 2006, "Lipoplexes formed from sugar-based gemini surfactants undergo a lamellar-to-micellar phase transition at acidic pH. Evidence for a non-inverted membrane-destabilizing hexagonal phase of lipoplexes," Biochim Biophys Acta. 1758(10):1677-84.
Yousef et al., 2012, "Chitosan oligosaccharide as potential therapy of inflammatory bowel disease: Therapeutic efficacy and possible mechanisms of action," Pharmacological Res., 66:66-79.
Barsotti et al., 2016, "One year in review 2016: systemic sclerosis", Clinical and Experimental Rheumatology, 34 (Suppl. 100):S3-S13.
Blatt et al., 2005, "Stimulation of skin's energy metabolism provides multiple benefits for mature human skin", Biofactors, 25(1-4): 179-185
Genetics Home Reference, 2019, "Ehlers-Danlos syndrome", Retrieved from the Internet, https://ghr.nlm.nih.gov/condition/ehlers-danlos-syndrome, (12 pages).
Jansen et al., 2009, "Beta-defensin-2 protein is a serum biomarker for disease activity in psoriasis and reaches biologically relevant concentrations in lesional skin", PLoS One, 4(3):e4725.
Kiritsi and Nystrom, 2018, "Recent advances in understanding and managing epidermolysis bullosa", F1000Research, 7(F1000 Faculty Rev), 1097: 7 pages.
Valanciene et al., 2010, "Pathogenesis and treatment modalities of localized scleroderma", Medicina (Kaunas), 46(10):649-656.

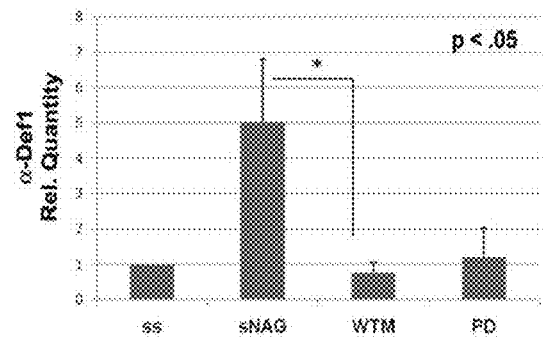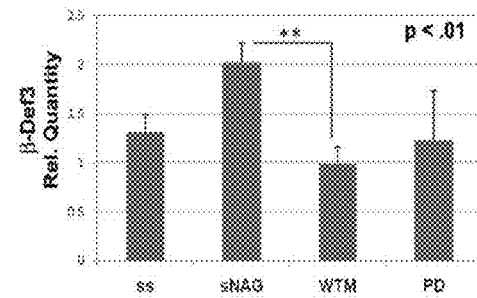
FIG. 8A  FIG. 8B
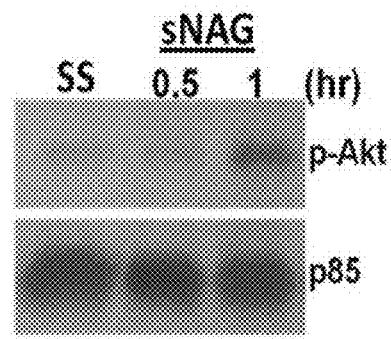
FIG. 8C
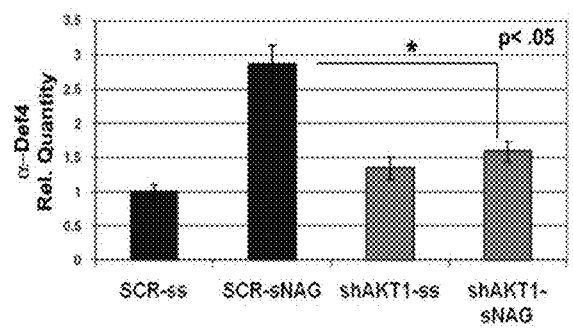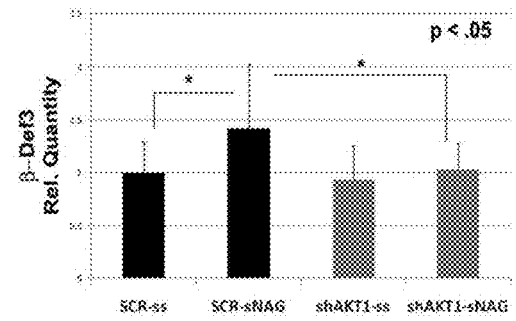
FIG. 8D  FIG. 8E

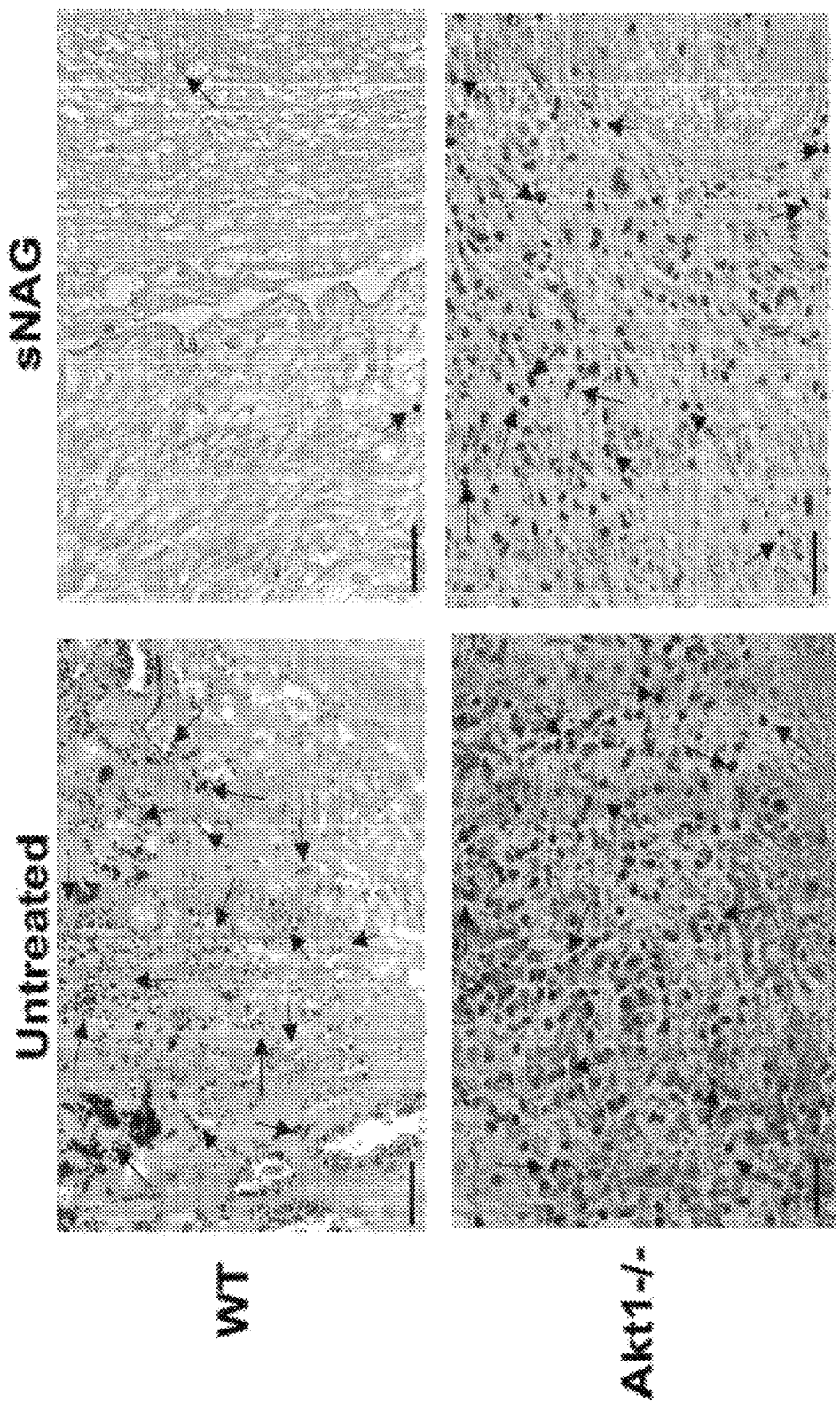

ANTI-BACTERIAL APPLICATIONS OF POLY-N-ACETYLGLUCOSAMINE NANOFIBERS

This application is a continuation of U.S. application Ser. No. 15/476,222 filed Mar. 31, 2017 (now U.S. Pat. No. 10,206,938), which is a continuation of U.S. application Ser. No. 14/927,372 filed Oct. 29, 2015 (now U.S. Pat. No. 9,642,871), which is a continuation of U.S. application Ser. No. 14/327,192 filed Jul. 9, 2014 (now U.S. Pat. No. 9,198,928), which is a continuation of U.S. application Ser. No. 13/641,015 that entered the U.S. national stage on Oct. 12, 2012 and was accorded a 371 filing date of Dec. 19, 2012 (now U.S. Pat. No. 8,858,964), which is a U.S. national stage entry of International Application No. PCT/US2011/032709 filed Apr. 15, 2011, which claims the benefit of U.S. Provisional Application No. 61/324,657, filed Apr. 15, 2010; each of the foregoing applications is incorporated by reference herein in its entirety.

1. FIELD

Described herein are compositions comprising shortened fibers of poly-N-acetylglucosamine and/or a derivative thereof ("sNAG nanofibers") and anti-bacterial applications of such compositions. The sNAG nanofibers may be formulated into compositions for the prevention and/or treatment of bacterial infections and diseases associated with such infections. Regimens employing such compositions are also described.

2. BACKGROUND

Currently, antibiotics are a standard therapy for bacterial infections. However, some individuals have an allergic reaction to certain antibiotics, others suffer from side effects associated with antibiotics, and the continued use of antibiotics often leads to a reduction in their efficacy. In addition, antibiotic therapy often leads to the emergence of antibiotic-resistant strains of bacteria. Accordingly, there is a continuing need for new anti-bacterial agents that are effective in fighting infection without generating resistance or reducing the efficacy overtime. There is a need for non-antibiotic anti-bacterial agents that can be used in clinical settings, e.g., in the treatment of infectious diseases of the skin, digestive and respiratory tract, and in wound treatment.

Wound infection is one type of bacterial infection. Wound infection is a major complication, especially in patients with chronic disease such as diabetes or during immunosuppression. Such patients have disruptions in appropriate inflammatory responses, including the migration and recruitment of neutrophils and macrophages, which predisposes them to increased infection (Singer, A. J. and R. A. Clark, 1999, N Engl J Med 341(10): 738-46). In addition, bacterial infection can lead to impairment of wound healing and sepsis. Given the ineffectiveness of many current antibiotic treatments and the increased prevalence of antibiotic resistant bacteria such as MRSA (Methycillin-resistant *S. aureus*), new clinical treatments are in high demand.

3. SUMMARY

In one aspect, described herein are methods for treating and/or preventing a bacterial infection(s) and/or diseases associated with or caused by a bacterial infection in a subject.

In certain embodiments, described herein are methods for treating a bacterial infection in a subject comprising topically administering a composition comprising sNAG nanofibers to a subject. In some embodiments, the subject is diagnosed with the bacterial infection or displaying one or more symptoms of the bacterial infection. The methods of diagnosis of bacterial infection and symptoms of bacterial infection are those known in the art or described herein. The bacterial infection may be a skin infection, a gastrointestinal infection, a respiratory infection, a urinary tract infection, a reproductive tract infection, or infection of any other organ or tissue in the body of the subject as described herein. In one embodiment, the infection is a nosocomial infection, an MRSA infection, a *Pseudomonas* infection, or a *C. difficile* infection.

In certain embodiments, described herein are methods for treating and/or preventing a disease associated with a bacterial infection or a bacterial imbalance in a subject comprising topically administering a composition comprising sNAG nanofibers to the subject. In one such embodiment, the method involves treating and/or preventing a disease associated with a bacterial infection. In another embodiment, the method involves treating and/or preventing a disease associated with a bacterial imbalance, for example, an imbalance in bacterial microbiota as described herein. In certain embodiments, the methods involve treating an existing bacterial infection. In some of these embodiments, the subject to be treated is diagnosed with a disease associated with a bacterial infection or displays one or more symptoms of such disease. In other embodiments, the subject to be treated is diagnosed with a disease associated with a bacterial imbalance or displays one or more symptoms of such imbalance. The disease may be a skin disease, a gastrointestinal disease, a respiratory disease, a urinary tract disease, a reproductive tract disease, or disease of any other organ or tissue in the body of the subject as described herein. In some embodiments, the disease is a skin disease or a gastrointestinal disease. In one embodiment, the disease is associated with a nosocomial infection, an MRSA infection, a *Pseudomonas* infection, or a *C. difficile* infection.

In some embodiments, described herein are methods for preventing a bacterial infection and/or a disease associated with a bacterial infection comprising topically administering a composition comprising sNAG nanofibers to a subject. In some embodiments, a composition comprising sNAG nanofibers is administered to a subject at high risk of a bacterial infection to prevent a disease associated with a bacterial infection. In specific embodiments, a composition comprising sNAG nanofibers is administered to a subject with a wound or a subject who has undergone a surgery. In one embodiment, the composition is administered to an immunocompromised subject. In some embodiments, a composition comprising sNAG nanofibers is administered to a wound, where the wound is at high risk of bacterial infection. In certain embodiments, the wound is an open wound. The open wound may be a gunshot wound, a puncture wound, a laceration wound, an abrasion, a cut, a penetration wound, a surgical wound, or any other wound. In certain embodiments, the wound may be a puncture wound, for example, a puncture wound that is caused by a hemodialysis procedure or a catheterization procedure. In such embodiments, the subject to be treated may have been diagnosed with a hemodialysis-related or catheterization-related infection. In one embodiment, the bacterial infection and/or the disease associated with a bacterial infection to be prevented by a sNAG composition is not in a wound (e.g., an open wound) or is not associated with a wound. In one such embodiment, the bacterial infection and/or the disease associated with a bacterial infection is not at the site of a wound (e.g., not at the site of an open wound).

In some embodiments, described herein are methods for treating a bacterially infected wound in a subject, comprising topically administering a composition comprising sNAG nanofibers to the wound site in a subject. In some embodiments, the subject to be treated is diagnosed with a bacterial infection or displays one or more symptoms of the bacterial infection. In certain embodiments, the wound is an open wound. The open wound may be a gunshot wound, a puncture wound, a laceration wound, an abrasion, a cut, a penetration wound, a surgical wound, or any other wound. In certain embodiments, the wound may be a puncture wound, for example, a puncture wound that is caused by a hemodialysis procedure or a catheterization procedure. In such embodiments, the subject to be treated may have been diagnosed with a hemodialysis-related or catheterization-related infection.

Bacterial infections to be treated or prevented using the methods described herein include infections with bacteria of one or more of the following genuses: *Bordetella, Borrelia, Brucella, Campylobacter, Chlamydia* and *Clamidophylia, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibria*, and *Yersinia*. In some embodiments, a sNAG composition may be used to treat and/or prevent a disease associated with an infection by bacteria from one or more of the listed genuses of bacteria, or one or more symptoms thereof.

Bacterial infections to be treated or prevented using the methods described herein also include infections with bacteria of one or more of the following species: *Bacillus anthracis, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Clamidophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Proteus mirabilis, Rickettsia rickettsii, Salmonella typhi, Salmonella typhimurium, Shigella sonnei, Staphylococcus aureus, Staphylococcus epidermidis, Staphylococcus saprophyticus; Streptococcus agalactiae, Streptococcus pneumonia, Streptococcus pyogenes, Treponema pallidum, Vibria cholerae*, and *Yersinia pestis*. In some embodiments, a sNAG composition may be used to treat and/or prevent a disease associated with an infection by bacteria from one or more of the listed species of bacteria, or one or more symptoms thereof.

In certain embodiments, the bacterial infection to be treated or prevented using the methods described herein is an MRSA infection, a *Pseudomonas* infection, or a *C. difficile* infection. In some embodiments, a sNAG composition may be used to treat and/or prevent a disease associated MRSA infection, a *Pseudomonas* infection, or a *C. difficile* infection, or one or more symptoms thereof symptom thereof.

In certain embodiments, the bacterial infection to be treated or prevented using the methods described herein is caused by bacteria that are known to one of ordinary skill in the art to be resistant to a standard anti-bacterial therapy, for example, resistant to one or more antibiotics. In one embodiment, the bacterial infection to be treated or prevented using the methods described herein is MRSA, e.g., a nosocomial MRSA. In some embodiments, a sNAG composition may be used to treat and/or prevent a disease associated with an infection by bacteria resistant to one or more antibiotics. In one embodiment, a sNAG composition may be used to treat and/or prevent a disease associated with MRSA, e.g., associated with a nosocomial MRSA.

The subject to be treated using the methods described herein may be a mammal, preferably a human. The subject can also be a livestock animal (e.g., a chicken, a cow, a pig, a goat) or a pet (e.g., a dog or a cat), or any other animal.

The sNAG nanofibers contemplated in the methods described herein may be of varying lengths, widths and molecular weights as described in Section 5.1, infra. In certain embodiments, the majority (and in certain embodiments, at least or more than 60%, 70%, 80%, 90%, 95% or 99%) of the sNAG nanofibers, or 100% of the sNAG nanofibers, are between about 1 to 15 μm in length. In some embodiments, the majority (and in certain embodiments, at least or more than 60%, 70%, 80%, 90%, 95% or 99%) of the sNAG nanofibers, or 100% of the sNAG nanofibers, are between about 2 to 10 μm, or 4 to 7 μm in length. The sNAG nanofibers of the described length can be obtained, for example, as described below in Section 5.2, infra.

In certain embodiments, the sNAG nanofibers were produced by irradiation, e.g., gamma irradiation, of poly-N-acetylglucosamine or a derivative thereof. In some embodiments, the sNAG nanofibers are produced by irradiation of the poly-β-1→4-N-acetylglucosamine in the form of dried fibers (e.g., at 500-2,000 kgy), or irradiation of the poly-β-1→4-N-acetylglucosamine in the form of wet fibers (e.g., at 100-500 kgy).

In certain embodiments, the sNAG nanofibers are derived from microalgae. In another embodiment, the sNAG nanofibers are not derived from crustaceans. In yet another embodiment, the sNAG nanofibers may be derived from microalgae, crustaceans (e.g., shrimp), fungus or any other source.

In one embodiment, the sNAG nanofibers comprise N-acetylglucosamine monosaccharides and/or glucosamine monosaccharides, wherein more than 60%, 70%, 80%, 90%, 95%, or 99% of the monosaccharides of the sNAG nanofibers are N-acetylglucosamine monosachharides. In another embodiment, the sNAG nanofibers comprise N-acetylglucosamine monosaccharides and/or glucosamine monosaccharides, wherein more than 70% of the monosaccharides of the sNAG nanofibers are N-acetylglucosamine monosachharides.

In certain embodiments, the sNAG nanofibers used in the methods described herein do not have an effect on bacterial growth or survival of *Staphylococcus aureus* bacterial cultures in vitro, or substantially have no effect on bacterial growth or survival of *Staphylococcus aureus* bacterial cultures in vitro. In some embodiments, the sNAG nanofibers reduce bacterial growth or survival of bacterial cultures in vitro by less than 1 log, 0.75 log, 0.5 log, 0.25 log, 0.2 log or 0.1 log, e.g., when *Staphylococcus aureus* bacterial cultures are treated/incubated with the sNAG nanofibers in vitro. The tests for the effect of sNAG nanofibers on bacterial growth or survival and the evaluation of the test results are described, for example, in Section 5.1, Example 2 (e.g., Section 6.2.2.5) and FIG. 11E, infra.

In certain embodiments, the sNAG nanofibers used in the methods described herein are non-reactive in a biocompatibility test or tests. For example, the sNAG nanofibers used in the methods described herein may be non-reactive when tested in an elution test, an intramuscular implantation test, an intracutaneous test, or a systemic test. In some embodiments, the compositions described herein are non-reactive when tested in an elution test, an intramuscular implantation test, an intracutaneous test, or a systemic test. In other embodiments, the sNAG nanofibers used in the methods described herein have Grade 0 or Grade 1 when tested in an elution test, an intramuscular implantation test, an intracutaneous test, or a systemic test. In yet another embodiment, the sNAG nanofibers used in the methods described herein are at most mildly reactive when tested in an elution test, an intramuscular implantation test, an intracutaneous test, or a systemic test. In one embodiment, the sNAG nanofibers or compositions comprising such nanofibers are non-reactive as determined by an intramuscular implantation test. In certain embodiments, the compositions described herein do not cause an allergenic reaction or an irritation, e.g., at the site of application. In other embodiments, the compositions described herein cause at most a mild allergenic reaction or a mild irritation, e.g., at the site of application.

The contemplated modes of administration of the compositions described herein are topical, e.g., topical on the skin; topical at the site of a wound, a surgery, a bacterial infection, or a symptom of an infection (e.g., a swelling); and topical to a body surface such as the skin, mucous membranes (e.g., vagina, anus, throat, eyes, ears), or the surface of other tissues. In certain embodiments, the sNAG nanofibers or compositions comprising such nanofibers are formulated as a dressing, a bandage, a mat, a spray, a liquid, a suspension, a membrane, a powder, an ointment, a cream, a paste, a suppository, or a gel. In some embodiments, the sNAG nanofibers or compositions comprising such nanofibers are formulated as a cream, a gel, an ointment, a membrane, a powder, a spray, or a suppository.

In another aspect, described herein are compositions for use in the methods described herein. In a specific embodiment, the compositions comprise sNAG nanofibers. In certain embodiments, the compositions described herein comprise sNAG nanofibers and one or more additional active ingredients useful in preventing and/or treating a bacterial infection, a disease associated with a bacterial infection, or a symptom thereof. In some embodiments, the additional active ingredient is an anti-bacterial agent. Such additional anti-bacterial agent may be an antibiotic. In another embodiment, such additional anti-bacterial agent is zinc. In yet another embodiment, the compositions described herein do not comprise an antibiotic. In yet other embodiments, the compositions described herein do not comprise any additional anti-bacterial agent. In one embodiment, the compositions described herein comprise the sNAG nanofibers as the only active ingredient and do not comprise any additional active ingredients.

In specific embodiments, a composition comprises the sNAG nanofibers and an antibiotic. Examples of antibiotics that can be used in the compositions of the invention include microlides (e.g., erythromycin, azithromycin), aminoglycosides (e.g., amikacin, gentamicin, neomycin, streptomycin), cephalosporins (e.g., cefadroxil, cefaclor, cefotaxime, cefepime), fluoroquinolones (e.g., ciprofloxacin, levofloxacin), penicillins (e.g., penicillin, ampicillin, amoxicillin), tetracyclines (e.g., tetracycline, doxycycline), and/or carbapenems (e.g., meropenem, imipenem). The sNAG nanofibers and agents described herein may be used in such compositions. In some embodiments, a composition comprises the sNAG nanofibers and an agent effective to treat or prevent or commonly used to treat or prevent an *S. aures* infection, MRSA infection, a *Pseudomonas* infection, or a *C. difficile* infection (e.g., an antibiotic effective against or commonly used against such infections).

In other embodiments, the compositions described herein are administered in conjunction with one or more additional anti-bacterial agents or any other suitable therapy. In some embodiments, the additional anti-bacterial agent or therapy is an antibiotic (e.g., a standard antibiotic therapy for the bacterial infection or a disease associated with a bacterial infection to be treated, as known in the art or described herein). In some embodiments, the additional anti-bacterial agent is an agent effective to treat or prevent or commonly used to treat or prevent an *S. aures* infection, MRSA infection, a *Pseudomonas* infection, or a *C. difficile* infection (e.g., an antibiotic effective against or commonly used against such infections). In some embodiments, the additional therapy is administered before, simultaneously with or after administration of a sNAG nanofiber composition. In yet another embodiment, the compositions described herein are not administered in conjunction with any other therapy, e.g., not administered in conjunction with an antibiotic.

3.1 Terminology

As used herein, the terms "sNAG nanofiber," "sNAG," "Taliderm," or "Talymed" (formerly known as "Taliderm") are used interchangeably to refer to shortened fibers of poly-N-acetylglucosamine and/or derivatives thereof.

As used herein, the term "about" means a range around a given value wherein the resulting value is the same or substantially the same (e.g., within 10%, 5% or 1%) as the expressly recited value. In one embodiment, "about" means within 10% of a given value or range. In another embodiment, the term "about" means within 5% of a given value or range. In another embodiment, the term "about" means within 1% of a given value or range.

As used herein, the terms "disease," "disorder" or "condition" are used interchangeably to refer to a medical condition in a subject. In a specific embodiment, the disease is the pathological state associated with or caused by a bacterial infection.

As used herein, the term "bacterial infection" means the invasion by, multiplication and/or presence of bacteria in a cell or a subject.

As used herein, the numeric term "log" refers to $\log_{10}$.

As used herein, the terms "therapies" and "therapy" can refer to any protocol(s), method(s), compositions, formulations, and/or agent(s) that can be used in the prevention and/or treatment of a bacterial infection or a symptom or condition associated therewith. In certain embodiments, the term "therapy" refers to a sNAG nanofiber(s) or a pharmaceutical composition comprising a sNAG nanofiber(s). In other embodiments, the term "therapy" refers to a therapy other than a sNAG nanofiber(s) or a pharmaceutical composition comprising a sNAG nanofiber(s). In specific embodiments, an "additional therapy" and "additional therapies" refer to a therapy other than a sNAG nanofiber(s) or a pharmaceutical composition comprising a sNAG nanofiber(s). In a specific embodiment, the therapy includes use of a sNAG nanofiber(s) or pharmaceutical composition comprising a sNAG nanofiber(s) as an adjuvant therapy; for example, using a sNAG nanofiber composition in conjunction with a drug therapy, such as an antibiotic, and/or other therapies useful in treatment and/or prevention of a bacterial infection or a symptom or condition associated therewith.

As used herein, the term "effective amount" in the context of administering a sNAG nanofiber composition to a subject refers to the amount of a sNAG nanofiber that results in a beneficial or therapeutic effect. In specific embodiments, an "effective amount" of a sNAG nanofiber refers to an amount which is sufficient to achieve at least one, two, three, four or more of the following effects: (i) the clearance of a bacterial infection; (ii) the eradication of one or more symptoms associated therewith, (iii) the reduction of time required to clear a bacterial infection; (iv) the reduction or amelioration of the severity of a bacterial infection and/or one or more symptoms associated therewith; (v) the reduction in the duration of a bacterial infection and/or one or more symptoms associated therewith; (vi) the prevention or delay of the generation of a resistant strain or strains of bacteria or reduction of a number of resistant strains of bacteria generated; (vii) the prevention in the recurrence of a bacterial infection and/or one or more symptoms associated therewith; (viii) the reduction or elimination in the bacterial cell population; (ix) the reduction in the severity and/or duration of a condition caused by or associated with a bacterial infection; (x) the reduction in hospitalization of a subject; (xi) the reduction in hospitalization length; (xii) the increase in the survival of a subject; (xiii) the enhancement or improvement of the therapeutic effect of another therapy; (xiv) a reduction in mortality; (xv) the reduction or elimination in the spread of the bacteria from one subject to another subject, or one organ or tissue to another organ or tissue; (xvi) the prevention of an increase in the number of bacteria; (xvii) the prevention of the development or onset of a bacterial infection or one or more symptoms associated therewith; (xviii) the reduction in the number of symptoms associated with a bacterial infection; (xix) the reduction in the duration and/or severity of a condition caused by or associated with a bacterial infection; (xx) the inhibition or reduction in production of a bacterial toxin or toxins associated with a bacterial infection; (xxi) the stabilization or reduction of inflammation associated with a bacterial infection; (xxii) the induction of the expression of one or more defensin proteins and/or defensin-like proteins; (xxiii) the induction of the expression of one or more Toll-like receptors; (xxiv) the induction of the expression of one or more proteins that are beneficial for clearance or reduction in a bacterial infection or one or more symptoms associated therewith; (xxvi) the reduction in organ failure associated with a bacterial infection or a disease associated therewith; (xxvii) the prevention of the onset, development or recurrence of a condition caused by or associated with a bacterial infection; and/or (xxviii) improvement in quality of life as assessed by methods well known in the art, e.g., a questionnaire. In specific embodiments, an "effective amount" of a sNAG nanofiber refers to an amount of a sNAG nanofiber composition specified herein, e.g., in Section 5.6, infra.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "premature human infant" refers to a newborn to 1 year old year human who was born of less than 37 weeks gestational age (e.g., before 37 weeks, 36 weeks, 35 weeks, 34 weeks, 33 weeks, 32 weeks, 31 weeks, 30 weeks, 29 weeks, 28 weeks, or less than 28 weeks of pregnancy).

As used herein, the term "human toddler" refers to a human that is 1 year to 3 years old.

As used herein, the term "majority" refers to greater than 50%, including, e.g., 50.5%, 51%, 55%, etc.

As used herein, the terms "subject" and "patient" are used interchangeably to refer to an animal (e.g., cow, horse, sheep, pig, chicken, turkey, quail, cat, dog, mouse, rat, rabbit, guinea pig, etc.). In a specific embodiment, the subject is a mammal such as a non-primate or a primate, e.g., a human. In specific embodiments, the subject is a human. See Section 5.5, infra, for more information concerning patients treated in accordance with the methods provided herein.

As used herein, the term "low expression," in the context of expression of a gene (e.g., based on the level of protein or peptide produced by the gene) refers to an expression that is less than the "normal" expression of the gene. In a specific embodiment, "low expression" refers to expression of a gene that is less than 90%, less than 80%, less than 75%, less than 70%, less than 65%, less than 60%, less than 55%, less than 50%, less than 45%, less than 40%, less than 35%, less than 30%, less than 25%, or less than 20% of the "normal" expression of the gene. In another specific embodiment, "low expression" refers to expression of a gene that is about 20-fold, about 15-fold, about 10-fold, about 5-fold, about 4-fold, about 3-fold, about 2-fold, or about 1.5 fold less than the "normal" expression of the gene.

4. BRIEF DESCRIPTION OF FIGURES

Figure 1B:
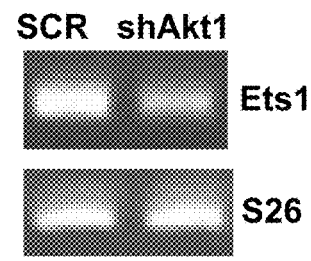
Figure 1C:
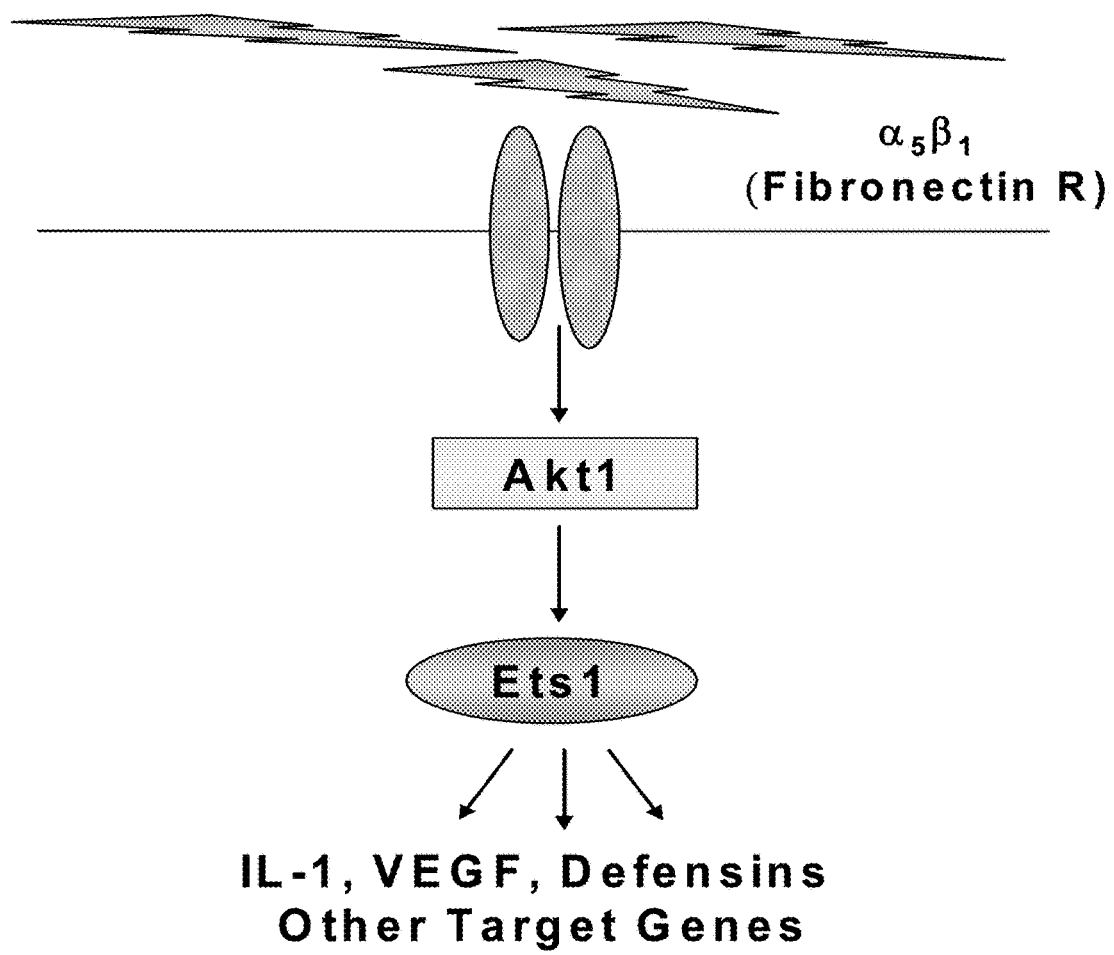

FIGS. 1A-C. Nanofibers stimulate Akt 1 activation, an upstream regulator of Ets1. (FIG. 1A) Western blot analysis of phospho-Akt in response to NAG and sNAG stimulation of serum starved EC. (FIG. 1B) RT-PCR analysis of EC infected either with scrambled control ("SCR") or Akt1 shRNA lentiviruses and assessed for expression of Ets1 and S26 as a loading control. (FIG. 1C) Schematic of a signal transduction pathway transducing a signal from sNAG nanofibers to Akt1, Ets1 and Defensins.

Figure 2A:
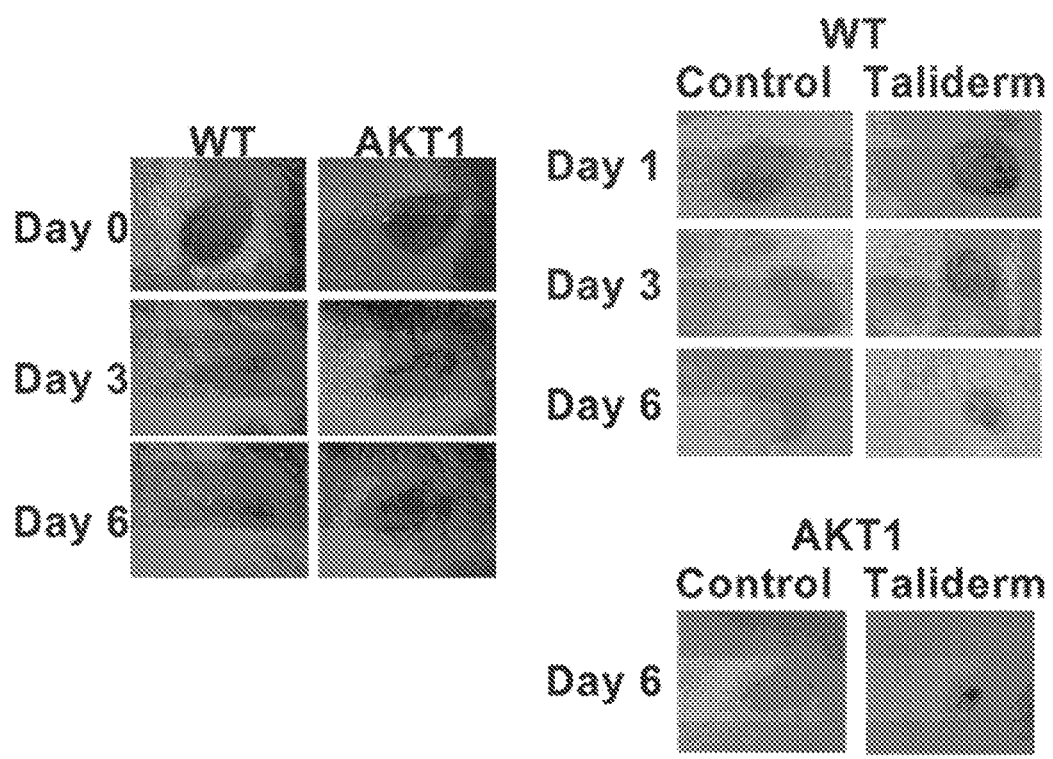
Figure 2B:
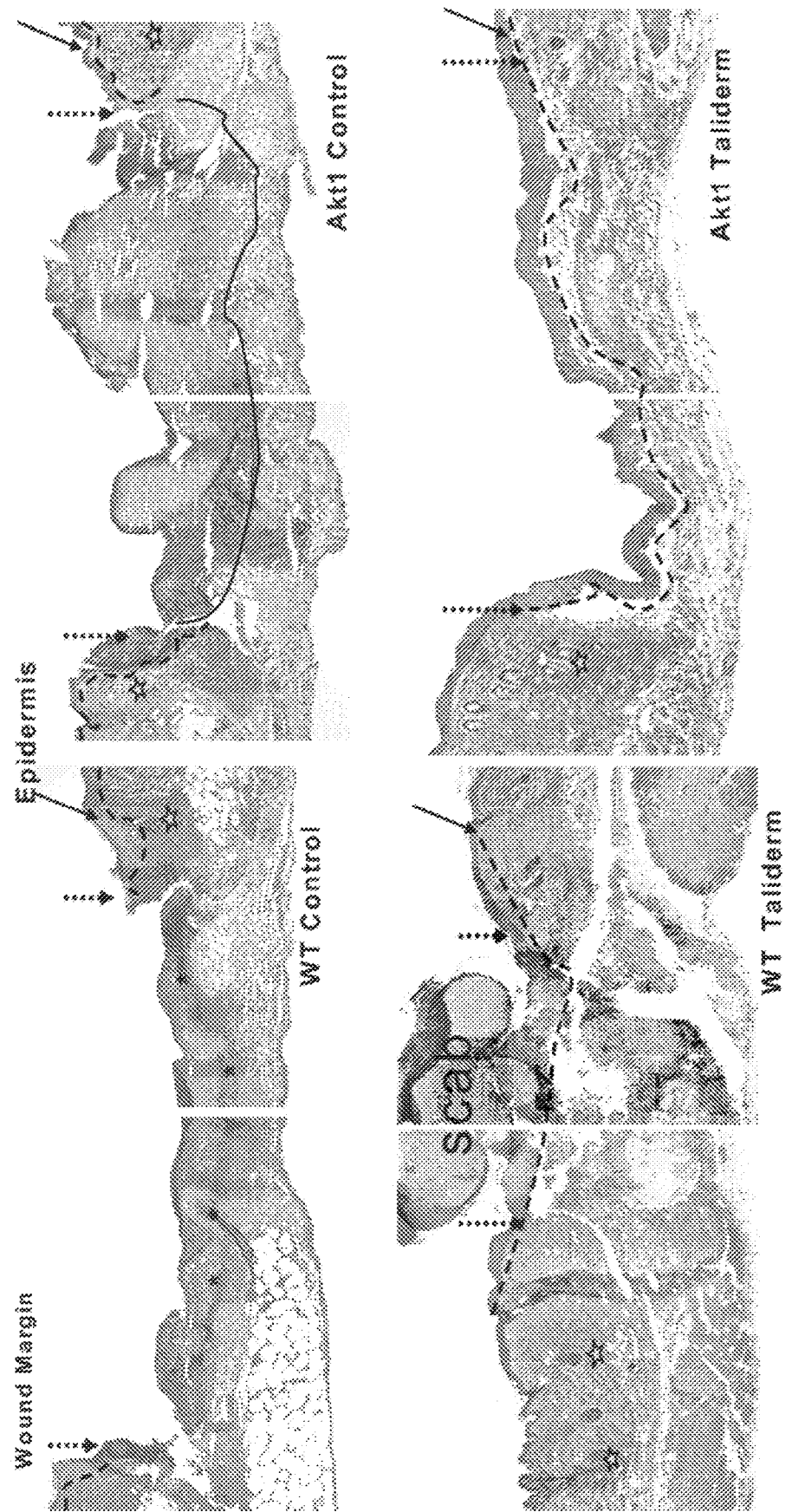

FIGS. 2A-2B. Delayed wound healing in Akt1 null animals is partially rescued by Taliderm treatment. (FIG. 2A) Representative images of wounded WT and AKT1 null mice with and without treatment of Taliderm. (FIG. 2B) H&E staining of representative mouse skin sections from day 3 wounds.

Figure 3A:
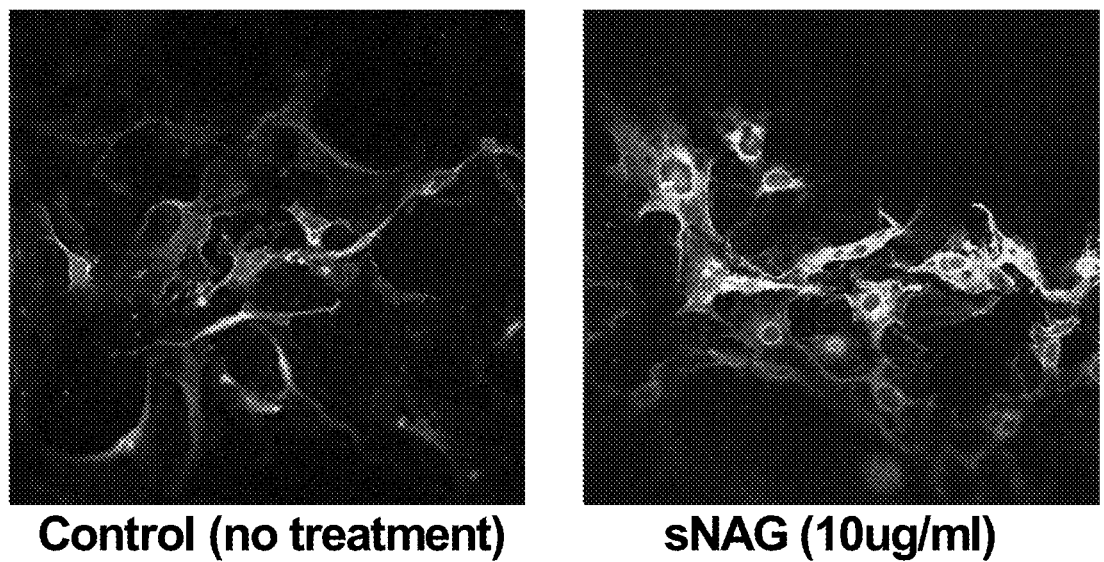
Figure 3B:
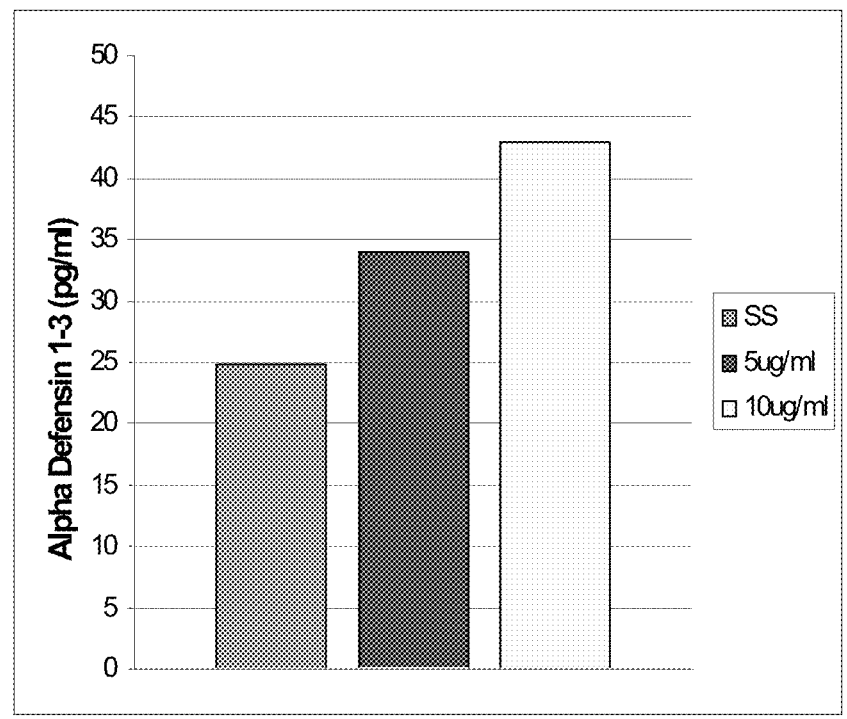

FIGS. 3A-B. sNAG nanofibers stimulate cytokine and defensin expression in primary endothelial cells. (FIG. 3A) Immunohistochemisty of EC treated with or without sNAG using an antibody directed against α-defensin. (FIG. 3B) ELISA showing that nanofiber treatment of EC results in the secretion of α-defensins 1-3 (serum starved, treated with 5 μg/ml or 10 μg/ml sNAG).

Figure 4A:
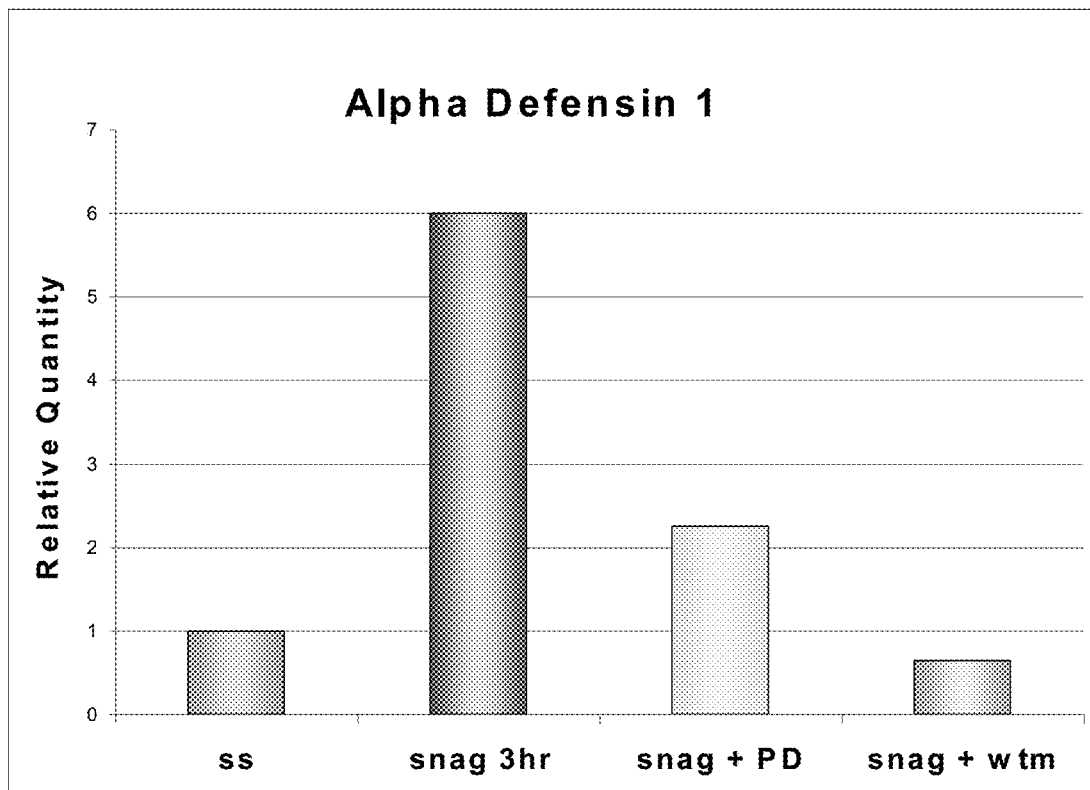
Figure 4B:
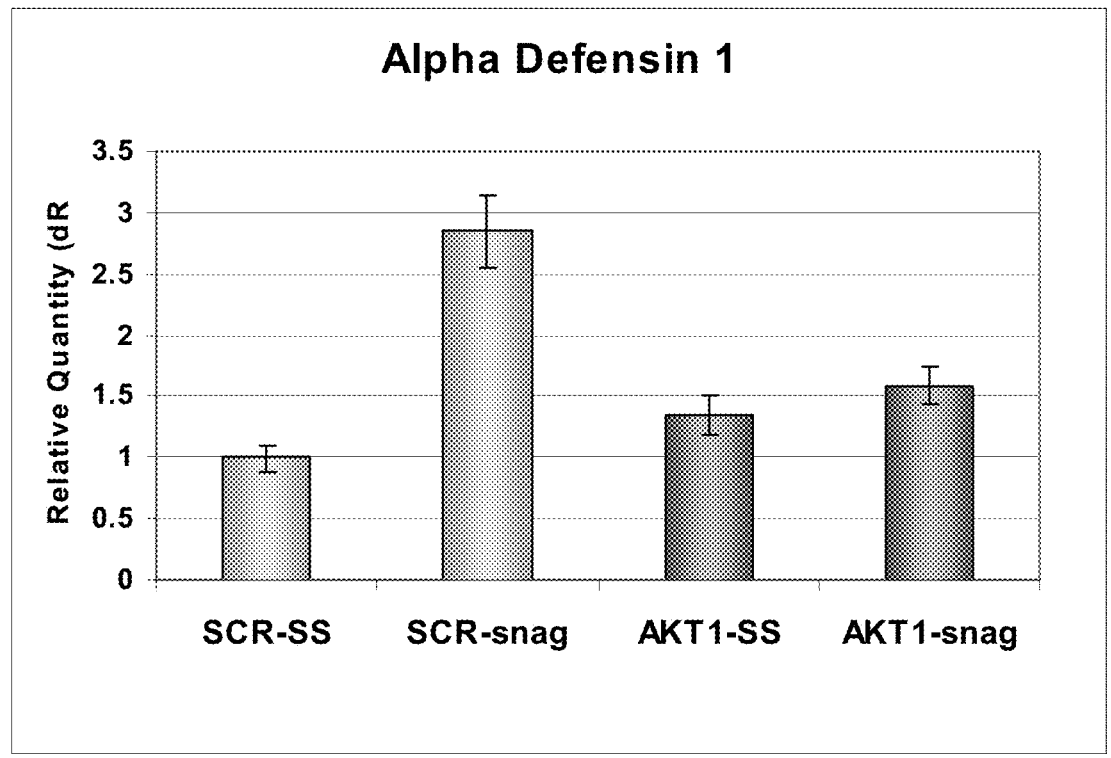

FIGS. 4A-B. sNAG nanofibers stimulate defensin expression in primary endothelial cells in an Akt1 dependent manner. FIGS. 4A-4B Quantitative RT-PCR analyses of serum starved EC ("ss") treated with or without sNAG ("snag"), with or without PD98059 (MAPK inhibitor, "PD"), Wortmannin (PI3K inhibitor, "wtm") or infected with a scrambled control ("SCR"), or Akt1 ("AKT1") shRNA lentiviruses and assessed for expression of the genes indicated.

Figure 5A:
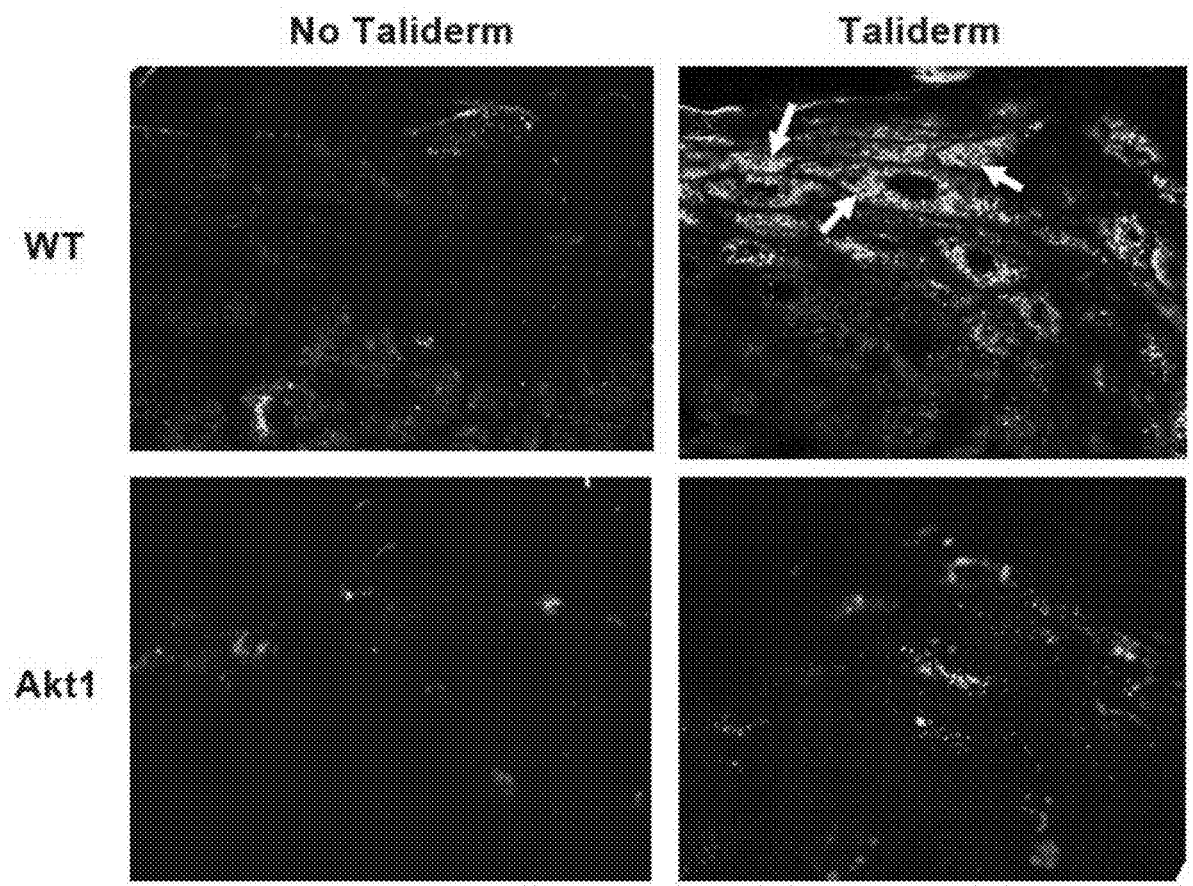
Figure 5B:
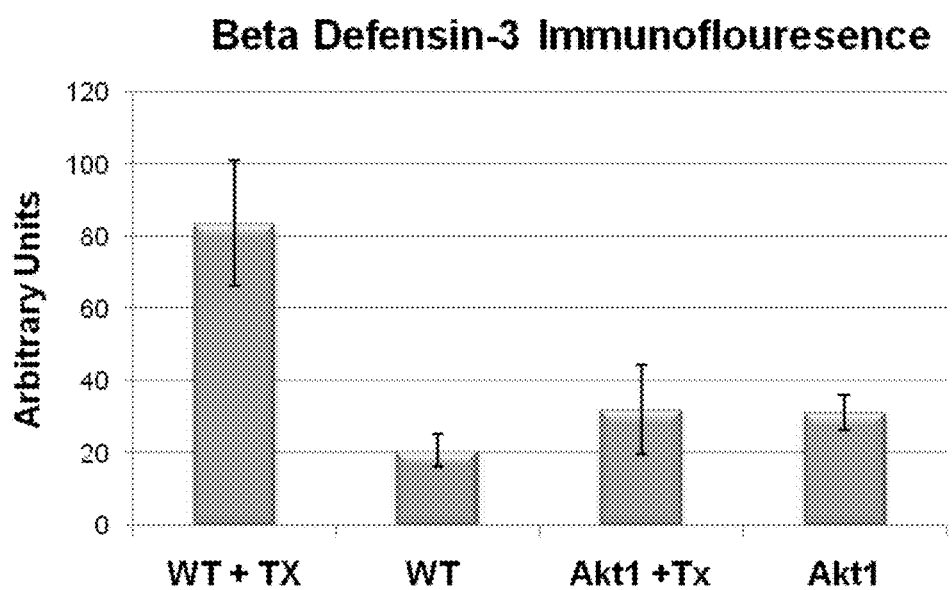
Figure 5C:
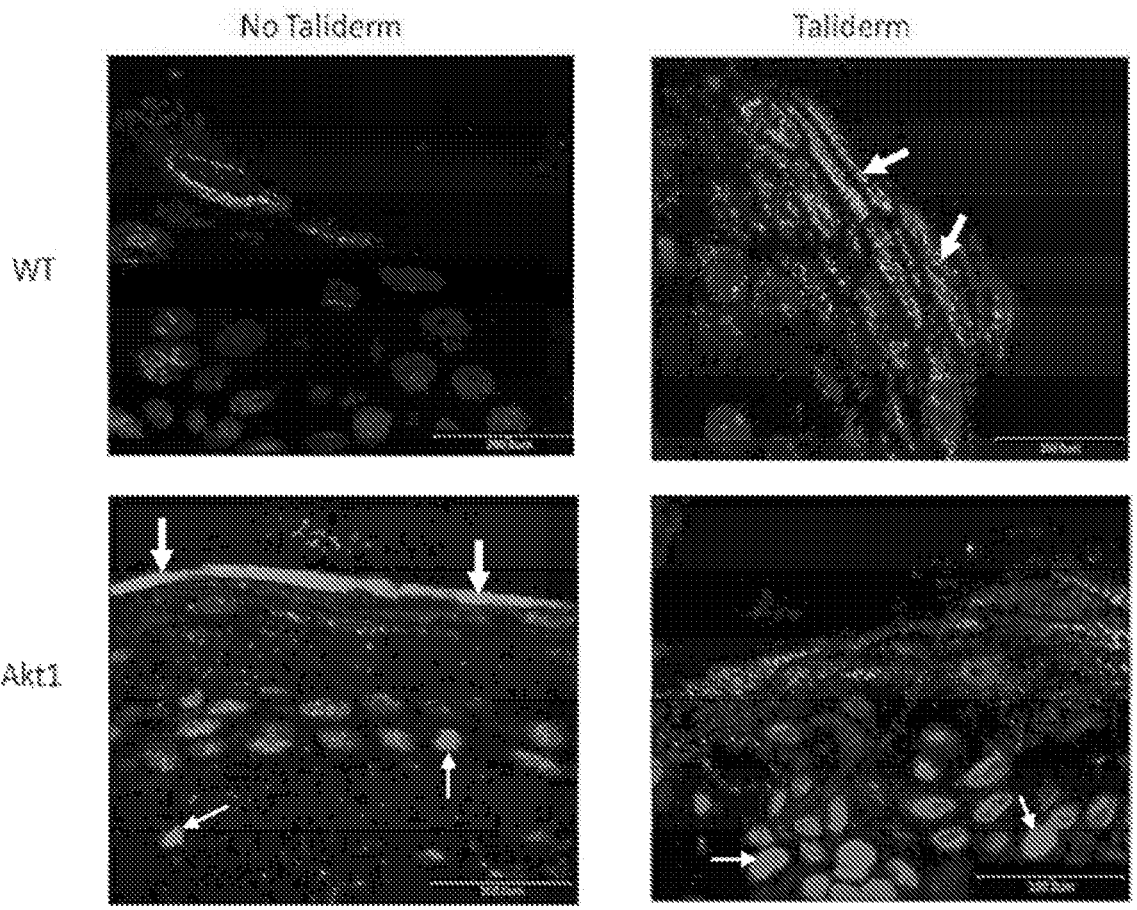

FIGS. 5A-C. sNAG nanofibers stimulate β-defensin 3 expression in mouse keratinocytes. (FIG. 5A) Immunofluorescent staining with β-defensin 3 (visible as bright staining in the upper right hand panel; see, e.g., thick white arrows) and Involucrin antibodies of paraffin embedded mouse cutaneous wound sections from WT and Akt1 null animals on Day 3. (FIG. 5B) Quantification of β-defensin 3 immunofluorescent staining using NIHImageJ software (TX=Taliderm; Akt1=Akt1 null). (FIG. 5C) Immunofluorescent staining of WT and Akt1 null treated and untreated keratinocytes with β-Defensin 3 (visible as bright staining; see, e.g., thick white arrows) and TOPRO-3 (nuclei staining; see, e.g., thin white arrows). Notice the increase in β-Defensin 3 staining in WT and Akt1 Taliderm treated wounds.

Figure 6:
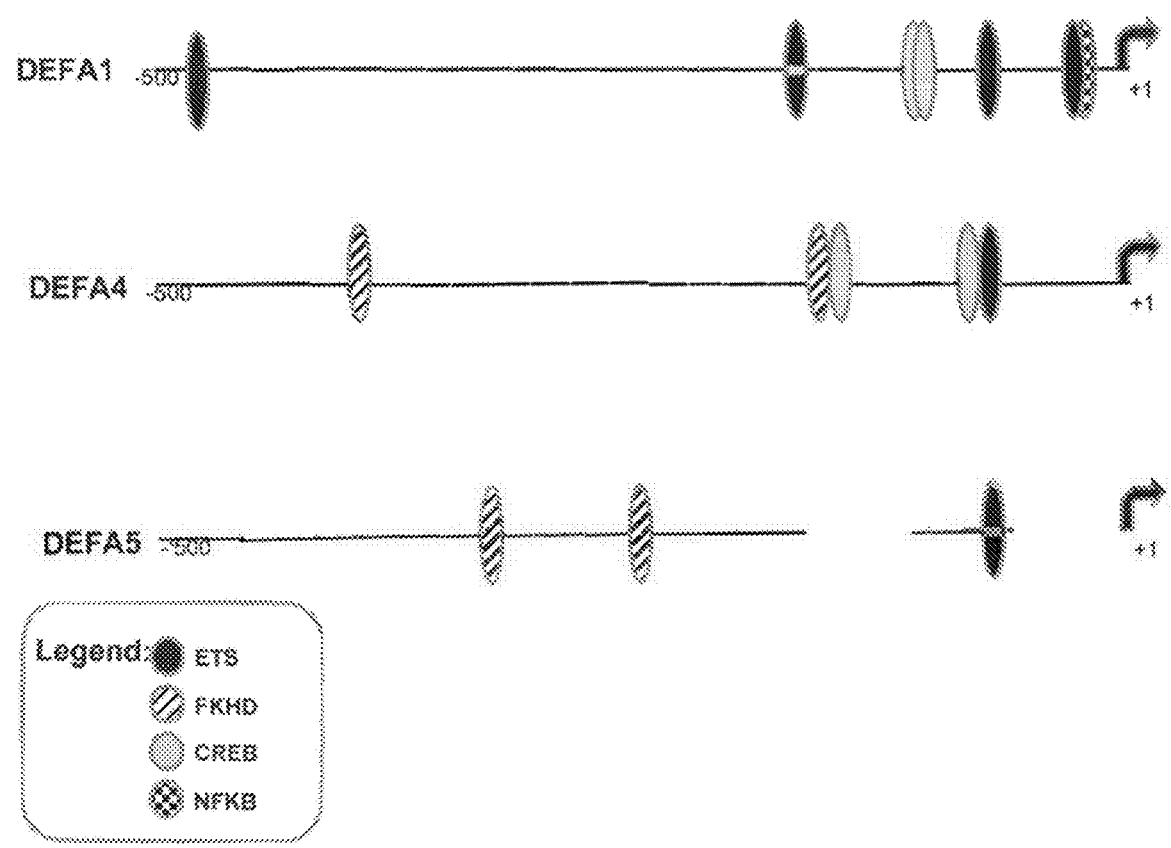

FIG. 6. Akt1 dependent transcription factor binding sites. Schematic of Akt1 dependent transcription factor binding sites. Using Genomatix software, 500 bp upstream of the transcription start site was analyzed for conserved sites on the mRNA of DEF1, 4, and 5 (ETS-black ovals; FKHD-striped ovals; CREB-white ovals; NFKB-checkered ovals).

Figure 7A:
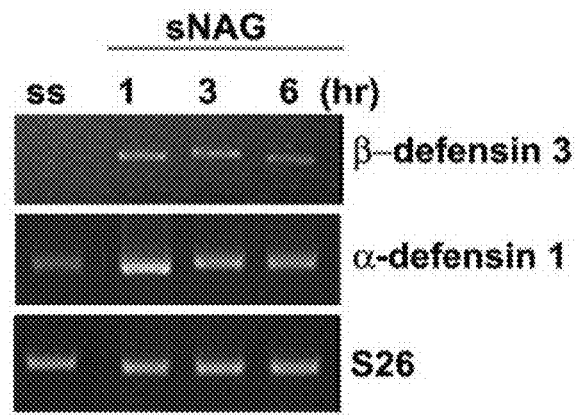
Figure 7B:
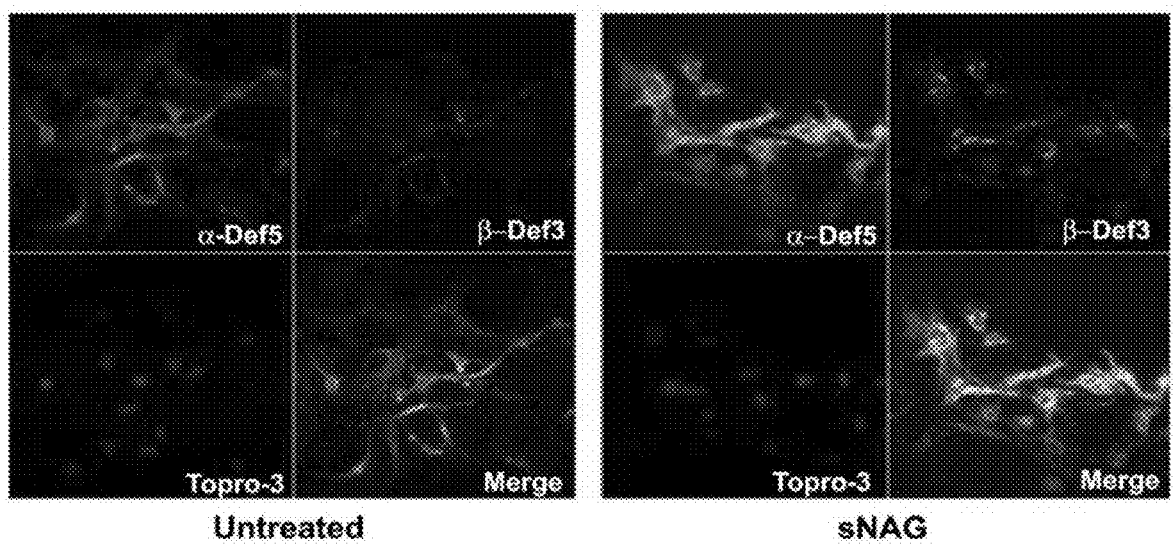
Figure 7C:
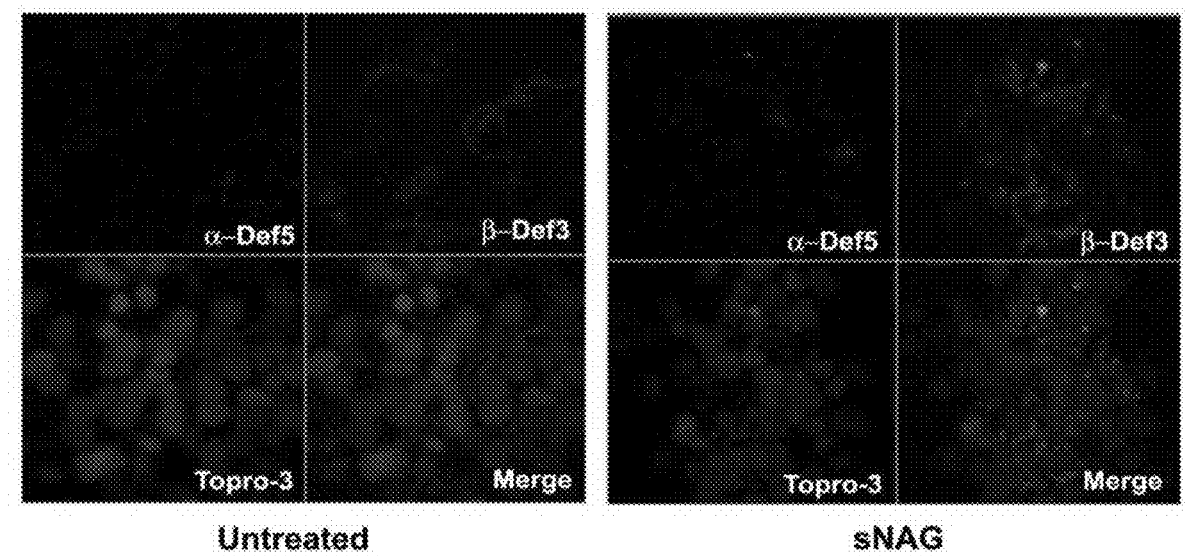

FIGS. 7A-C. sNAG treatment results in expression and secretion of defensins in vitro. (FIG. 7A) TPCR analysis of serum starved ("SS") primary endothelial cells treated with sNAG (50 µg/ml) for the times indicated and assessed for expression of β-defensin 3 and α-defensin 1. (FIG. 7B) Immunofluorescent labeling of endothelial cells either serum starved (untreated) or treated with sNAG nanofibers (10 µg/ml for 5 hrs). Antibodies are directed against α-defensin 5 (FITC, upper left hand panel), β-defensin 3 (Texas Red, upper right hand panel). Nuclei are stained with TOPRO-3 (Blue, lower left hand panel). Lower right hand panel represents triple overlay. (FIG. 7C) Immunofluorescent labeling of keratinocytes (HaCat) that are either serum starved (untreated) or treated with sNAG nanofibers (10 µg/ml for 5 hours). Antibodies are directed against α-defensin 5 (FITC, upper left hand panel), β-defensin 3 (Texas Red, upper right hand panel). Nuclei are stained with TOPRO-3 (Blue, lower left hand panel).

FIGS. 8A-E. sNAG induced defensin expression is dependent on Akt1. (FIG. 8A) Quantitative RT-PCR analyses using primers directed against α-defensin 1 from total RNA isolated from serum starved endothelial cells treated with or without sNAG for 3 hours, with or without pretreatment with PD098059 ("PD")(50 µM), wortmannin ("WTM")(100 nm). Quantitation is relative to the S26 protein subunit. (FIG. 8B) Quantitation of β-defensin 3 expression from total RNA isolated from serum starved endothelial cells treated with or without sNAG for 3 hours, with or without PD98059 (50 µm), wortmannin (100 nm) and shown as relative to S26. (FIG. 8C) Western Blot analysis of phospho-Akt in serum starved endothelial cells (SS) stimulated with sNAG for the times indicated. Line indicates where lanes have been removed (FIG. 8D) Quantitative RT-PCR analyses of serum starved endothelial cells infected with a scrambled control (SCR) or Akt1 shRNA lentiviruses, treated with or without sNAG and assessed for α-defensin 4 expression. Quantitation is shown relative to S26. (FIG. 8E) Quantitation of β-defensin 3 expression from total RNA isolated from serum starved endothelial cells infected with a scrambled control (SCR) or Akt1 shRNA lentiviruses, treated with or without sNAG. Quantitation is shown relative to S26. All experiments were done in at least triplicate and repeated at least three independent times and p values are shown.

Figure 9A:
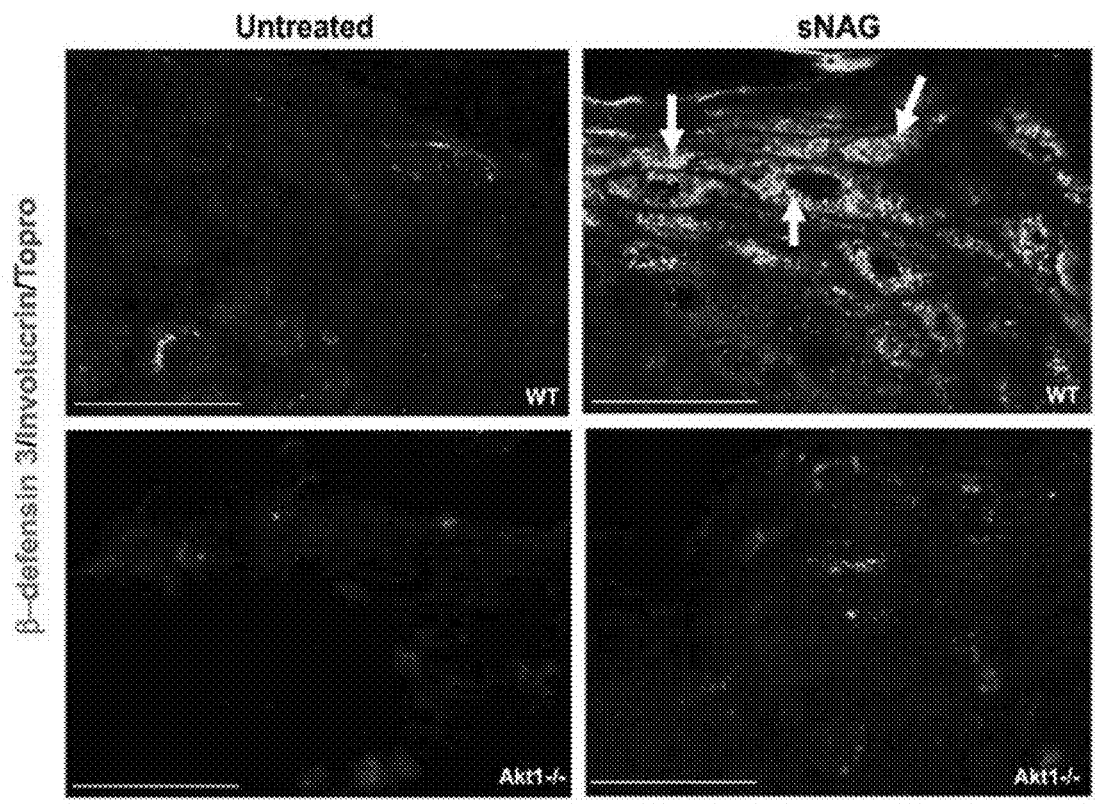
Figure 9B:
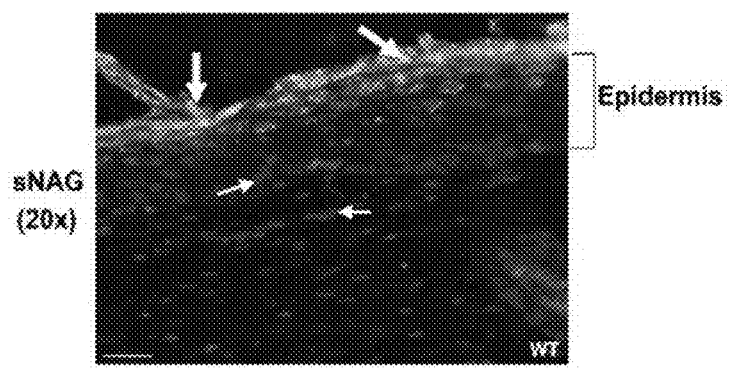
Figure 9C:
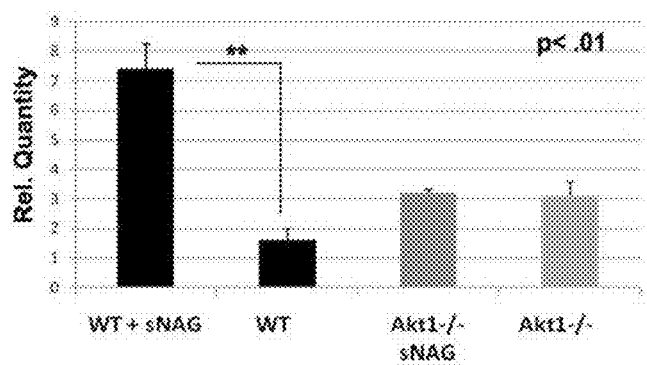

FIGS. 9A-C. sNAG induced defensin expression in vivo requires Akt1. (FIG. 9A) Paraffin embedded sections of cutaneous wounds harvested on day 3 post wounding from both WT (n=3) and Akt1 mice. Wounds were either untreated or treated with sNAG membrane. Immunofluorescence was performed using antibodies directed against β-defensin 3 (green, visible as bright staining in the upper right hand panel; see, e.g., white thick arrows), Involucrin (Red), and Topro (Blue, nuclei staining; see, e.g., white thin arrows). (FIG. 9B) Paraffin embedded section from WT treated with sNAG harvested on day 3. Immunofluorescence was performed using antibodies directed against β-defensin 3 (green, visible as bright staining; see, e.g., thick white arrows), Involucrin (Red), and Topro (Blue, nuclei staining; see, e.g., thin white arrows). This lower magnification (20×) is included to better illustrate the epidermal layers expressing β-defensin 3. Scale bars=50 µm. (FIG. 9C) Quantitation of β-defensin 3 expression from paraffin embedded sections was performed using NIH ImageJ software. Experiments were repeated three independent times and p values are shown.

Figure 10:
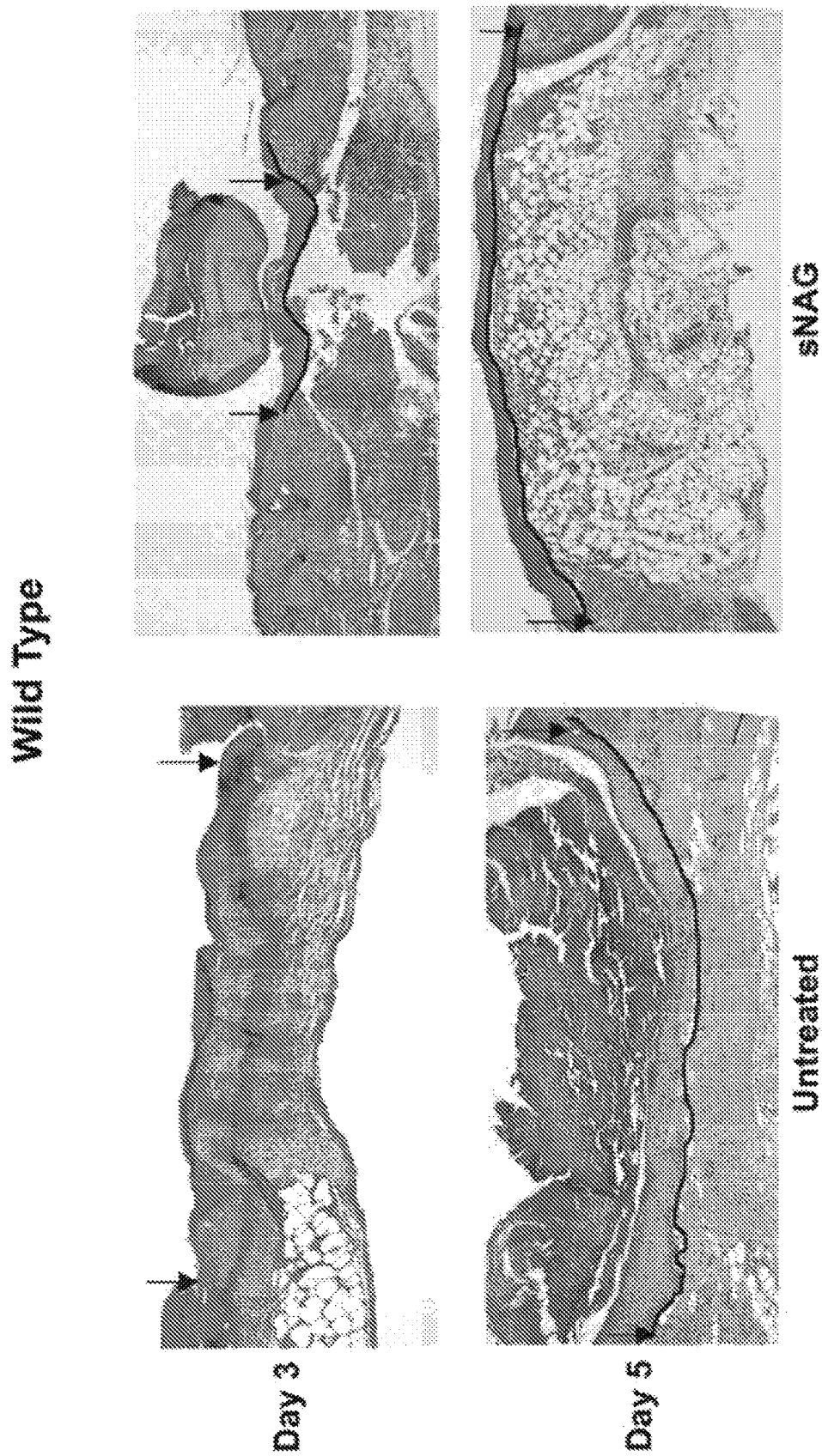

FIG. 10. sNAG treatment increases wound closure in wild type mice. H&E staining of wound tissue sections derived from C57B16 wild type animals either untreated or treated with sNAG membrane. The day post-wound is indicated to the left of each panel. The solid black line follows the keratinocyte cell layer indicating wound closure. Black arrows indicate the margin of the wound bed.

FIGS. 11A-G. sNAG treatment reduces bacterial infection in an Akt1 dependent manner. (FIG. 11A) Tissue gram staining of S. aureus infected wounds from WT mice. WT mice were wounded using a 4 mm biopsy punch. Immediately after wounding mice were inoculated with $1 \times 10^9$ cfu/ml. 30 minutes post-infection, mice in the treated group were treated with Taliderm. Skin samples were taken 5 days post-treatment and sectioned for analysis. Tissue gram staining was performed. Dark purple staining indicates gram-positive bacteria and neutrophils that have engulfed bacteria. Sections under 20× and 40× magnification are shown. (FIG. 11B) Tissue gram staining of paraffin embedded S. aureus infected wounds from WT and Akt1 null mice (n=3). Infected wounds were either untreated or treated with sNAG membrane and wound beds were harvested on day 3 and day 5 for analysis. Dark purple staining indicates the presence of gram positive bacteria in the wound bed. Black arrows indicate examples of gram positive staining. Note the accumulation of positive staining in untreated WT that is lacking in WT animals treated with sNAG. Scale bars=50 µm. (FIG. 11C) CFUs derived from day 5 post wounding were quantitated from S. aureus infected wounds using both treated and untreated WT (n=3) and Akt1 mice (n=3). Wild type mice that were sNAG treated show a significant (p<0.01) decrease in bacteria load in the wound beds as compared to Akt1 null animals. All experiments were repeated three independent times and the p values are shown. (FIG. 11D) CFU quantitated from infected wounds at day 3 post wounding in a similar fashion described in (FIG. 11C). sNAG treatment of infected wounds shows a significant decrease in CFU of both WT and Akt1 null animals on day 3, but the WT animals show an approximate 10 fold difference compared to a 2 fold difference in Akt1 animals. (FIG. 11E) Quantitation of CFUs in S. aureus cultures that were either untreated or treated with various amounts of sNAG nanofibers. Each experiment was performed three independent times and p values are shown. (FIG. 11F) Tissue gram staining of S. aureus infected wounds harvested on day 3 post wound from WT mice (n=3) that were treated with or without β-defensin 3 peptide (1.0 uM). Note the decrease in gram positive staining in infected wounds that were treated with β-defensin 3 peptide. (FIG. 11G) Quantitation of CFUs from S. aureus infected WT mice (n=3) treated with or without β-defensin 3 peptide. Infected wounds that were treated with peptide show a significant decrease (p<0.05) in CFU. Scale bars=50 µm. Each experiment was performed three independent times and p values are shown.

Figure 12A:
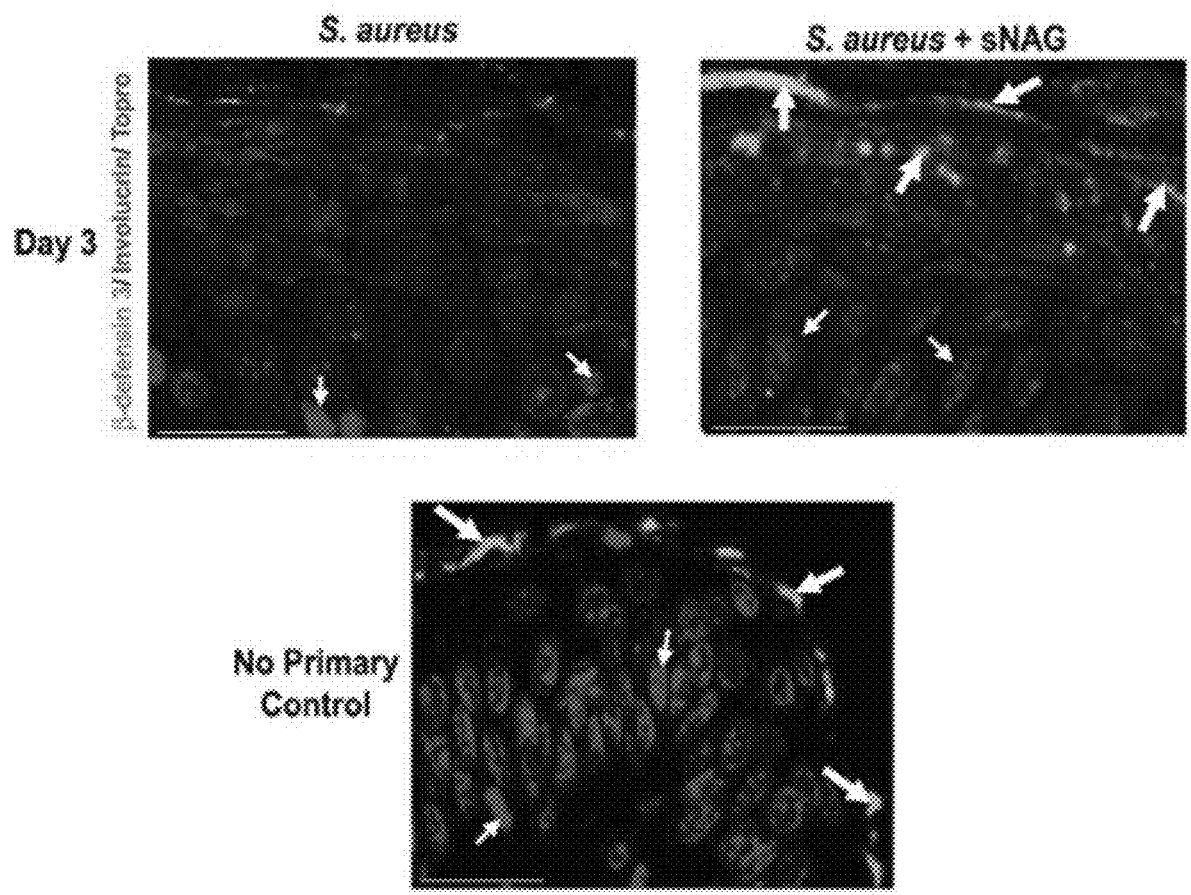
Figure 12B:
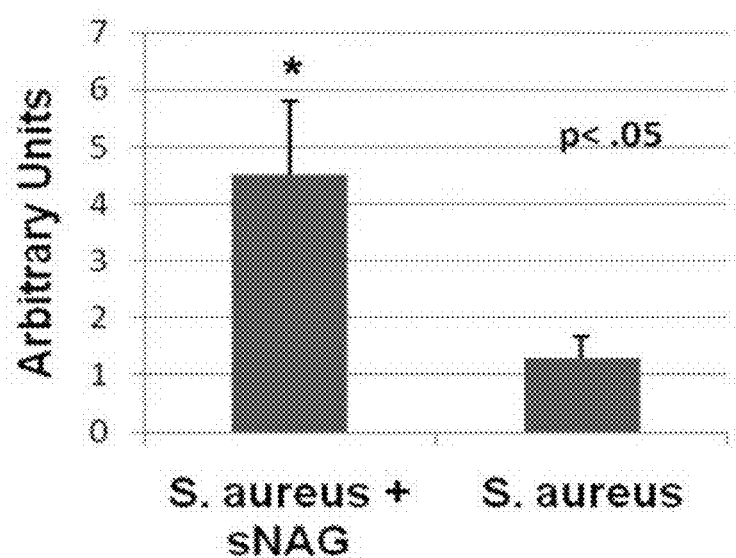

FIGS. 12A-B. Rapid induction of defensin expression by sNAG treatment of S. aureus infected wounds. (FIG. 12A)

Paraffin embedded tissue sections from *S. aureus* infected wounds, harvested on day 3, were subjected to immunofluorescence using antibodies directed against β-defensin 3 (green, visible as bright staining in the upper right hand panel and in the lower panel in the middle; see, e.g., thick white arrows), Involucrin (red) to mark the keratinocyte layer, and Topro (blue, nuclei staining; see, e.g., thin white arrows) from both sNAG treated WT (n=3) and untreated WT mice (n=3). Non specific staining of keratin is indicated by the no primary control which was stained with secondary antibody only. Scale bar=50 μm. (FIG. 12B) Quantitation of β-defensin 3 expression from paraffin embedded sections using NIH ImageJ software. *S. aureus* infected wounds that were treated with sNAG show a significant increase (p<0.05) in β-defensin 3 staining. Experiments were repeated three independent times and p values are shown.

Figure 13A:
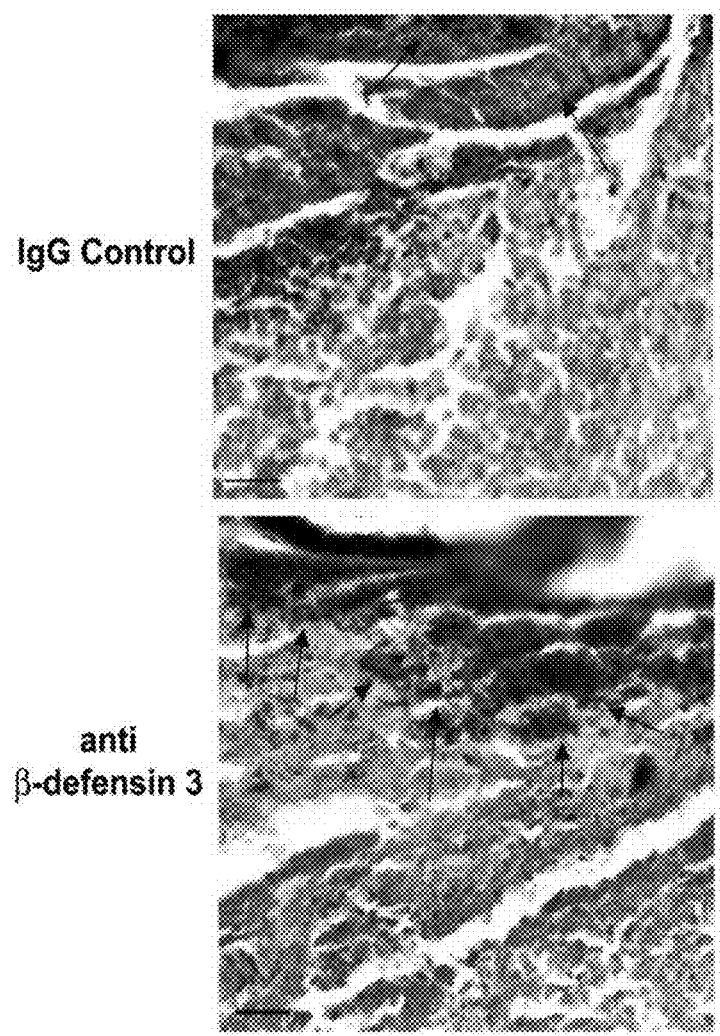
Figure 13B:
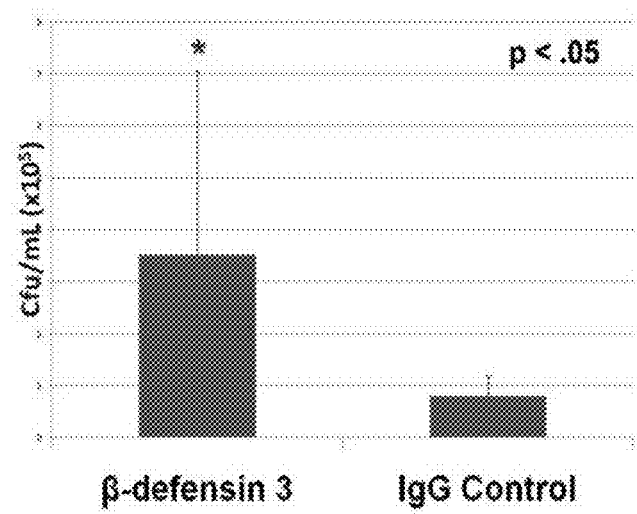

FIGS. 13A-B. Antibodies against β-defensin 3 impedes antibacterial effects of sNAG treatment. (FIG. 13A) Tissue gram staining of paraffin embedded *S. aureus* infected wounds treated with sNAG from WT mice (n=3) that were harvested on Day 3. sNAG treated wounds were treated with either β-defensin 3 antibody or isotype control goat IgG antibody prior to sNAG treatment. Representative images show increased accumulation gram positive staining (black arrows) in the wound beds of mice treated with an antibody directed against β-defensin 3. Scale bar=20 μm. (FIG. 13B) Quantitation of CFUs from *S. aureus* infected WT mice treated either β-defensin 3 antibody (n=3) or control IgG antibody (n=3) prior to sNAG treatment. β-defensin 3 application significantly increased (p<0.05) CFU.

Figure 14:
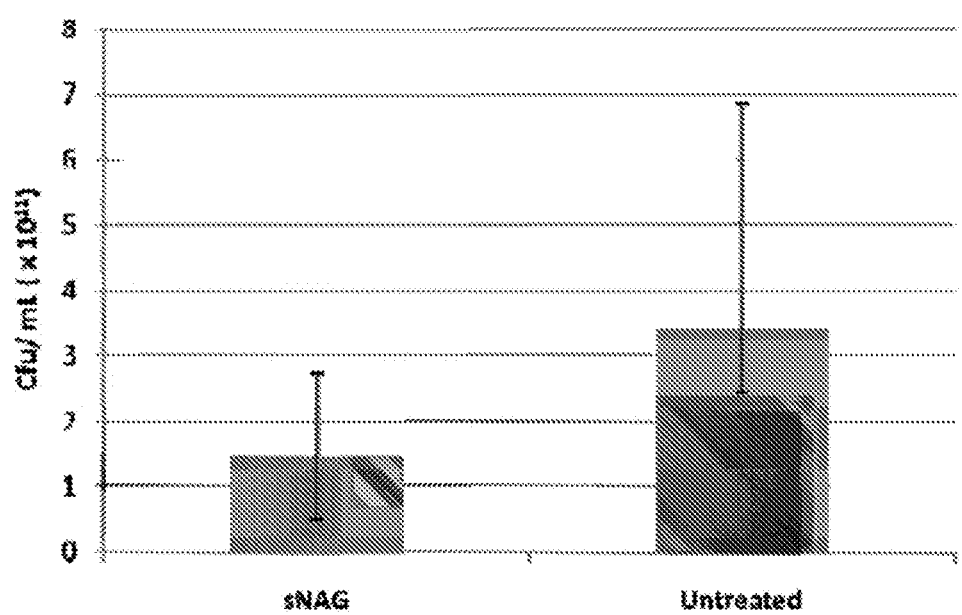

FIG. 14. sNAG treatment reduces bacterial infection by *Pseudomonas aeruginosa*. Mice were wounded using a 4 mm biopsy punch, inoculated with $1.5\times10^9$ cfu/ml *P. aeruginosa*, infected wounds were either untreated (n=6) or treated (n=6) with sNAG membrane (n=6) 30 min post-infection, wound beds were harvested on day 3 for analysis, cultured for 30 minutes, plated, and CFUs of the untreated and treated infected wounds were quantitated. sNAG treated mice show a significant (p<0.05) decrease in bacteria load in the wound beds as compared to untreated animals.

FIGS. 15A-D. Effect of irradiation on chemical and physical structure of pGlcNAc fibers. (FIG. 15A) Correlation between molecular weight of pGlcNAc and irradiation level/formulation for irradiation. (FIG. 15B) Infrared (IR) spectrum of non-irradiated pGlcNAc slurry (top line), pGlcNAc slurry irradiated at 100 kGy (bottom line), and pGlcNAc slurry irradiated at 200 kGy (middle line). (FIG. 15C) Scanning electron microscopic (SEM) analyses of pGlcNAc. (FIG. 15D) Scanning electron microscopic (SEM) analyses of sNAG.

Figure 16:
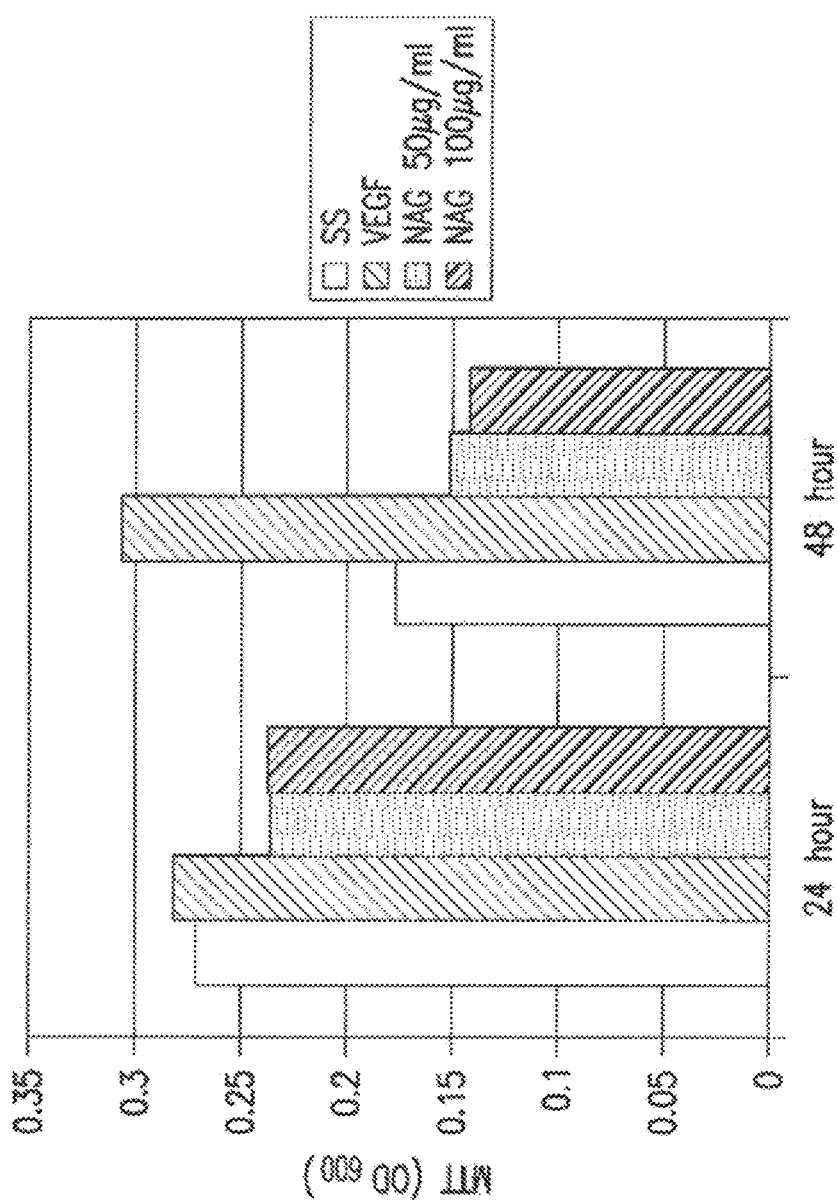

FIG. 16. pGlcNAc did not affect metabolic rate. For each time period (i.e., at 24 and 48 hours), the identity for each of the four bars (from left to right) is as follows: serum starvation (SS), VEGF, and pGlcNAc (NAG) at 50 and 100 μg/ml.

Figure 17:
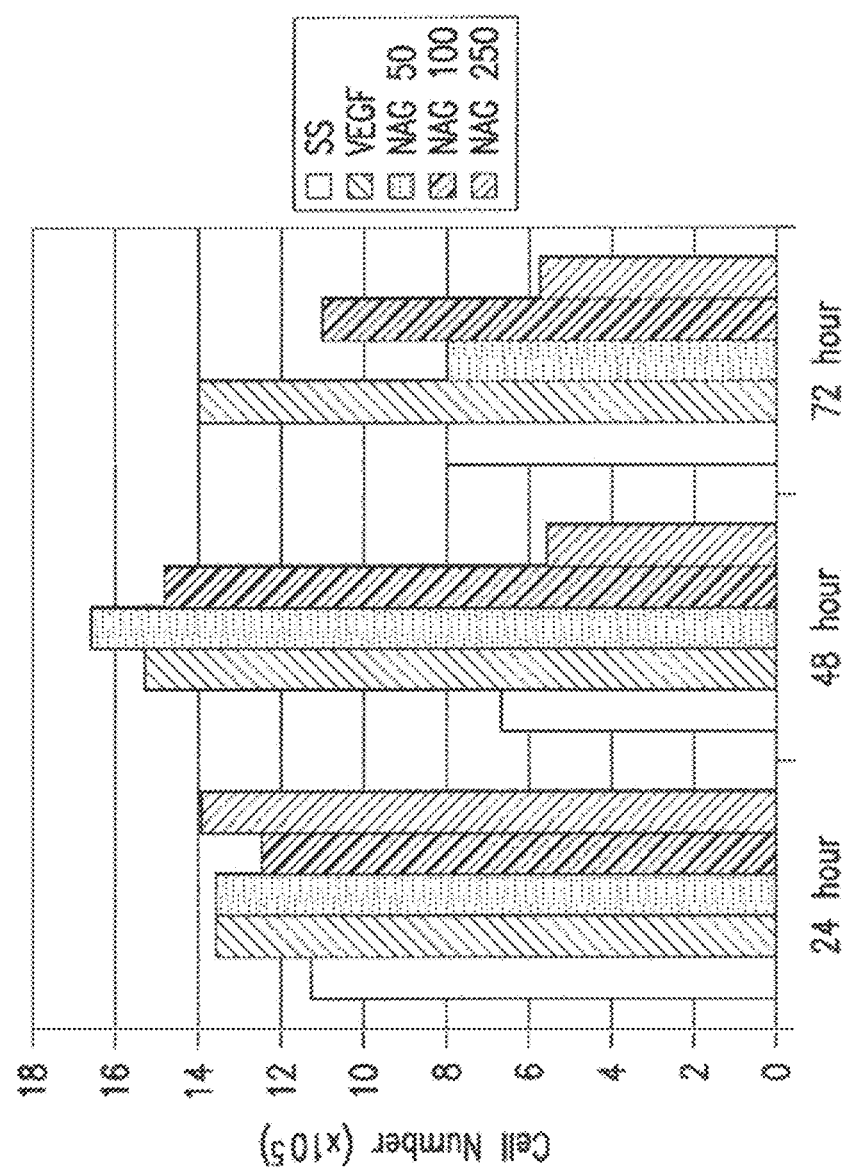

FIG. 17. pGlcNAc protected human umbilical vein endothelial cell (EC) from cell death induced by serum deprivation. For each time period (i.e., at 24, 48 and 72 hours), the identity for each of the five bars (from left to right) is as follows: serum starvation (SS), VEGF, and pGlcNAc (NAG) at 50, 100, and 250 μg/ml.

Figure 18:
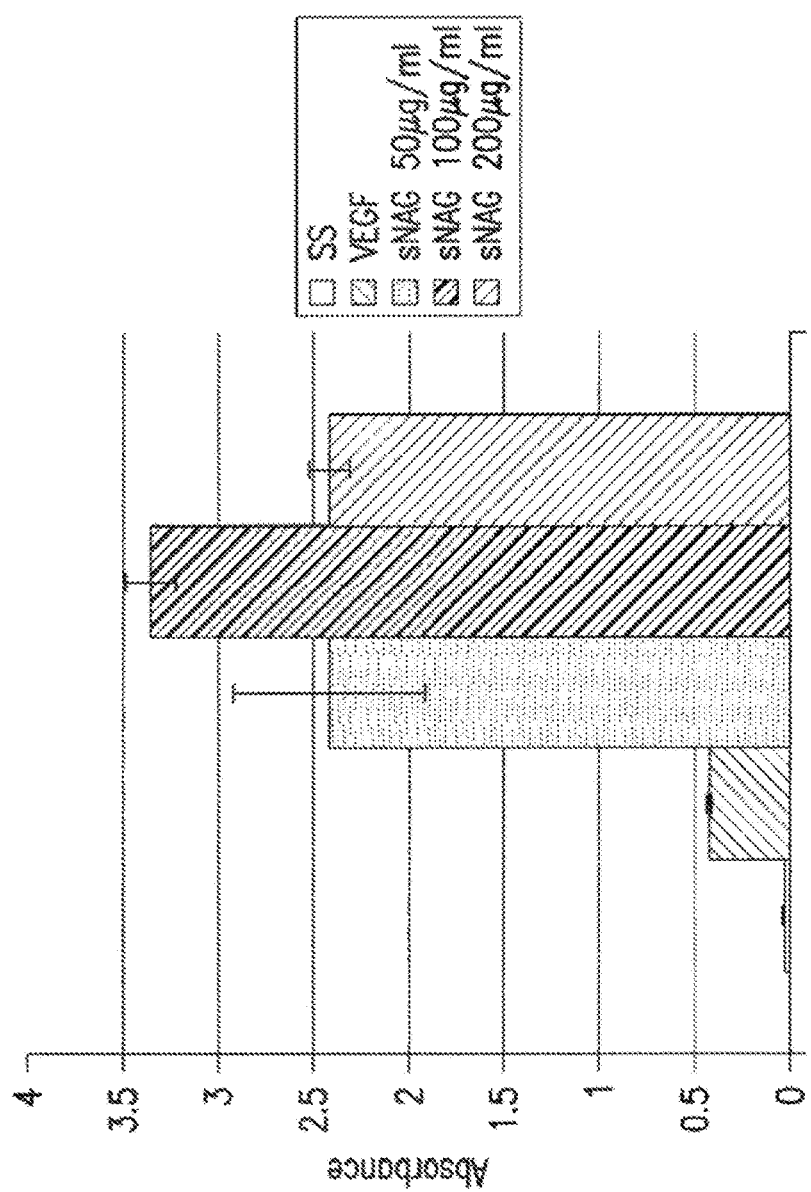

FIG. 18. sNAG induced marked increase in metabolic rate. Identity for each of the five bars (from left to right) is as follows: serum starvation (SS), VEGF, and sNAG at 50, 100 and 200 μg/ml.

Figure 19:
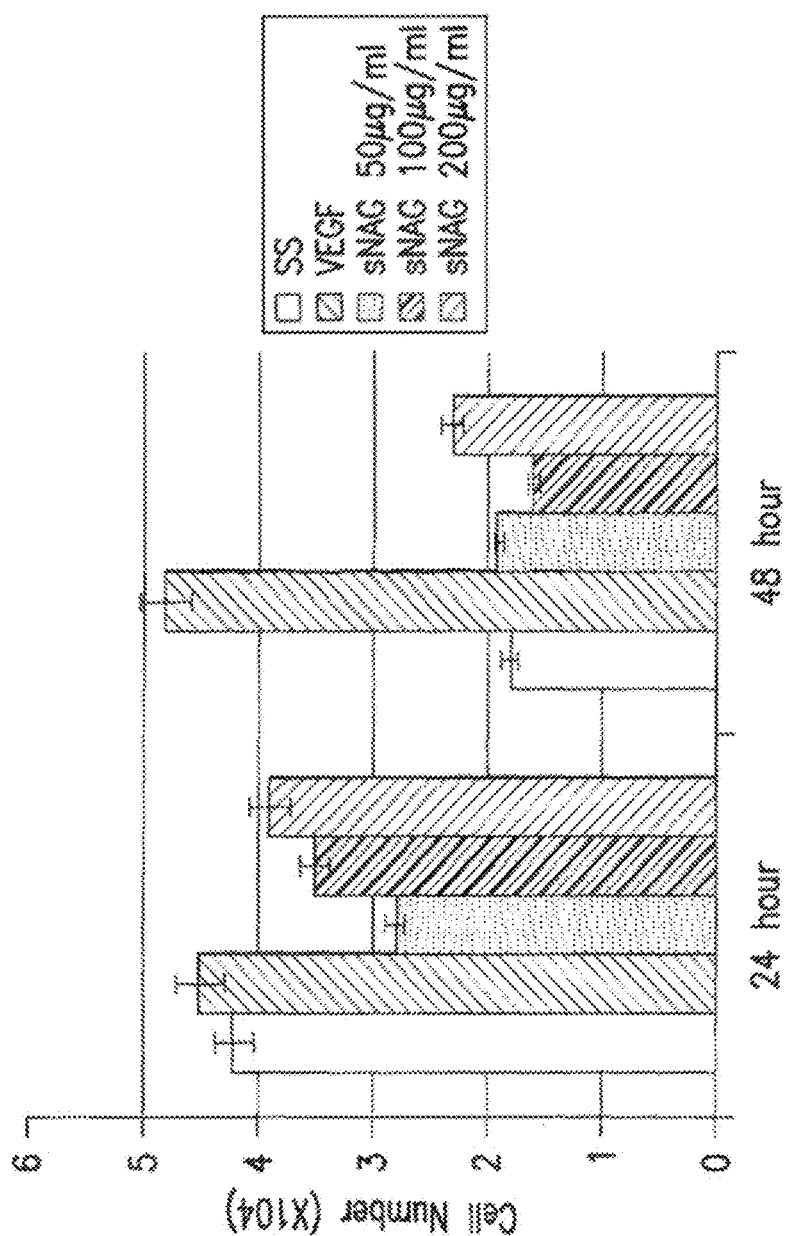

FIG. 19. sNAG did not protect EC from cell death induced by serum deprivation. For each time period (i.e., at 24 and 48 hours), the identity for each of the five bars (from left to right) is as follows: serum starvation (SS), VEGF, and sNAG at 50, 100 and 200 μg/ml.

5. DETAILED DESCRIPTION

Figure 11A:
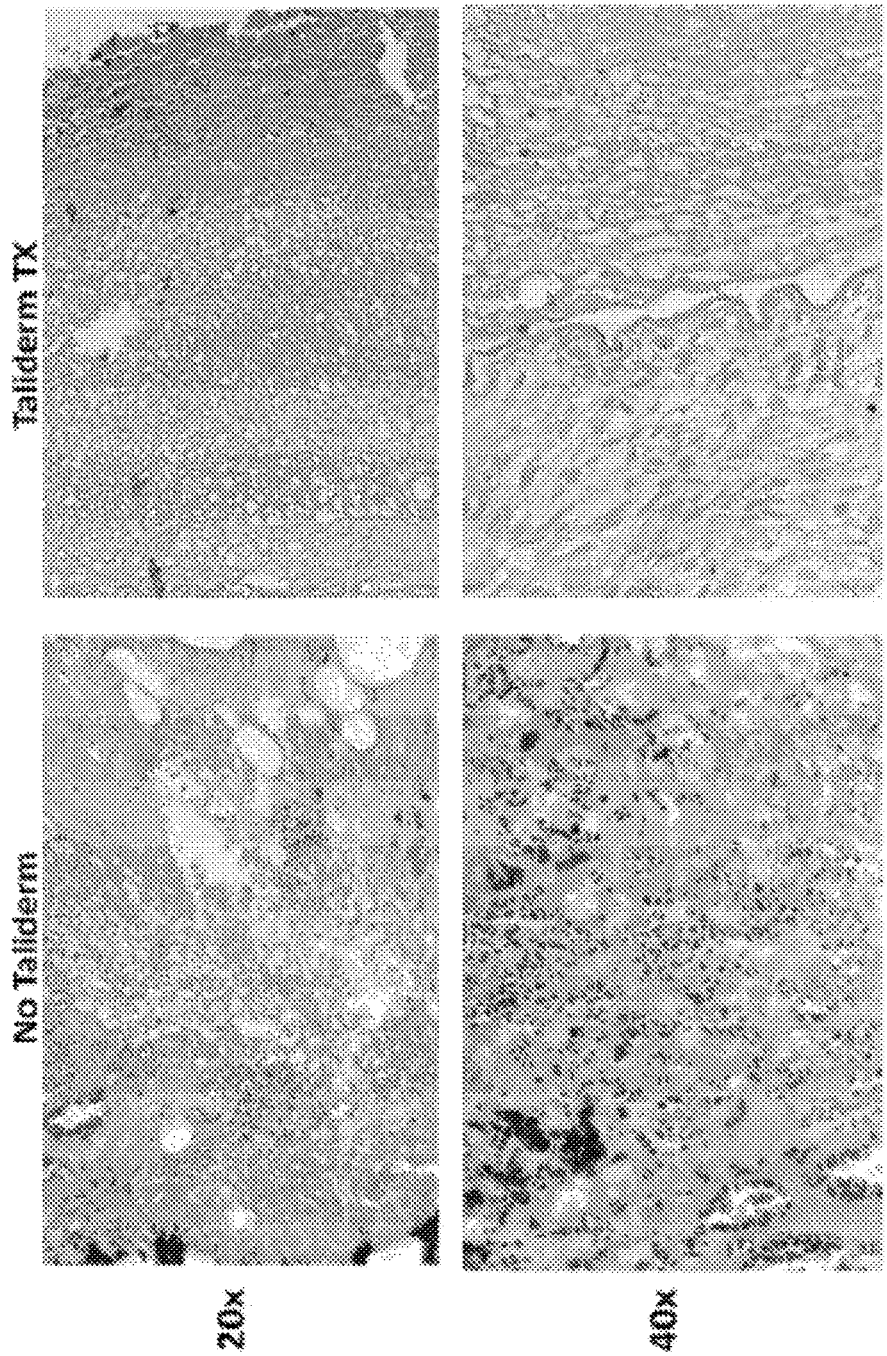
Figures 11C, 11D, 11E:
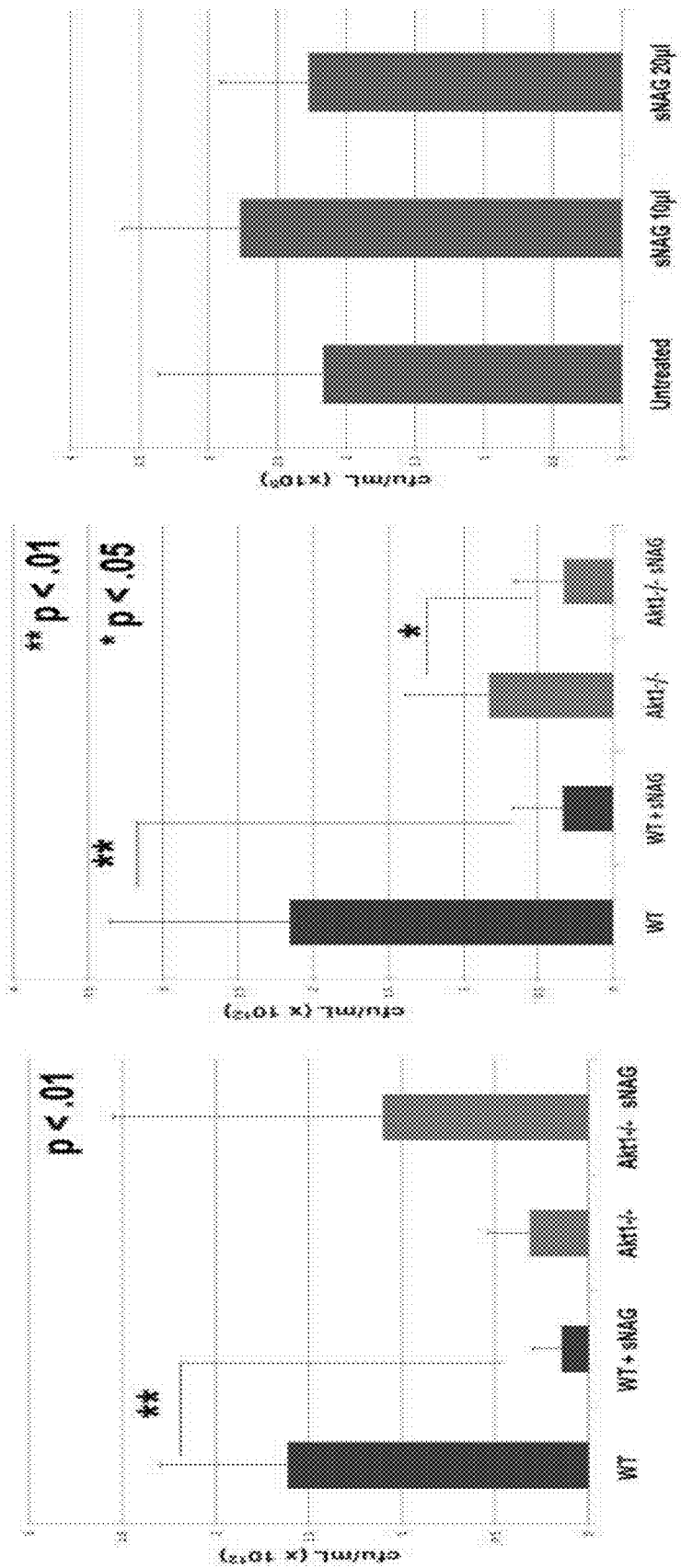
Figure 11F:
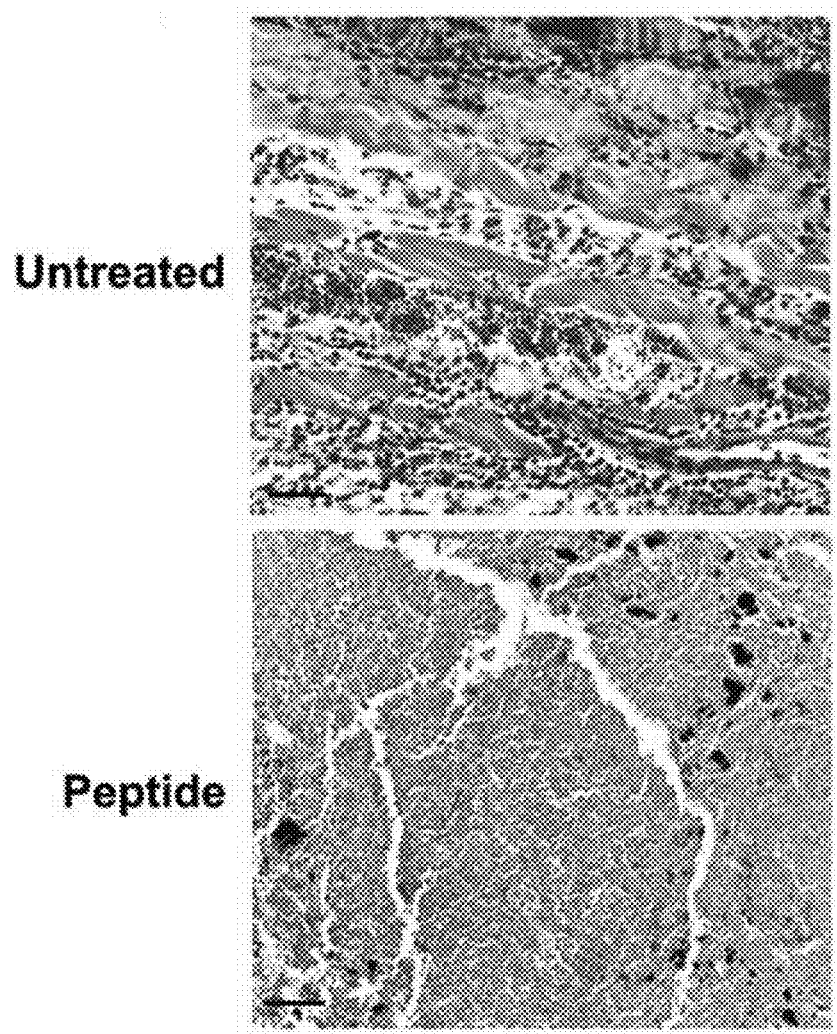
Figure 11G:
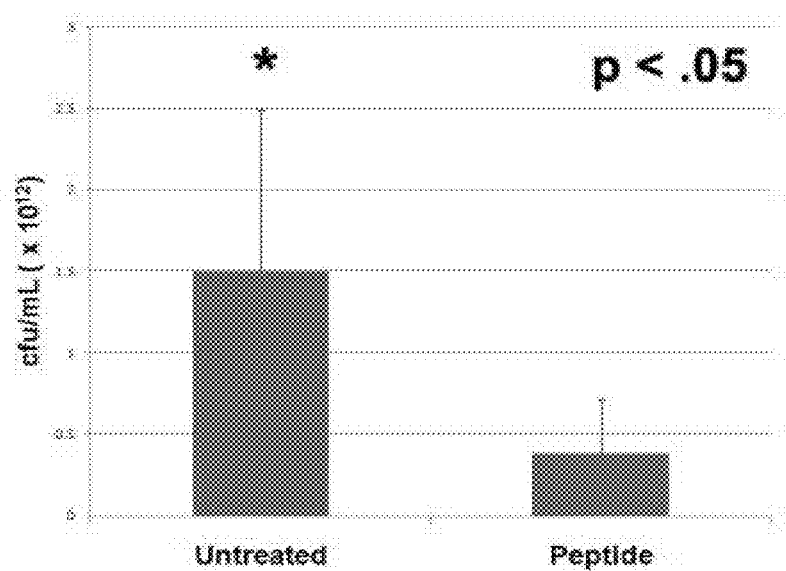

The inventors have discovered that sNAG nanofibers decrease bacterial infection of cutaneous wounds infected with *Staphylococcus aureus* and *Pseudomonas aeurginosa*. Without being bound by any specific mechanism of action, data presented in Section 6.2 suggests that the antibacterial effect of sNAG is not due to a direct interaction of sNAG with the bacteria but is due to downstream affects such as, for example, the regulation of defensins by Akt1 activation. Specifically, data show that treatment of bacterial cultures with sNAG nanofibers in vitro does not affect bacterial count indicating that sNAG nanofibers do not directly inhibit bacterial growth. In a specific example described in Section 6.2.2.5 and illustrated in FIG. 11E, sNAG nanofibers do not have a direct effect on growth or survival of *Staphylococcus aureus*. The test described in Section 6.2.2.5, infra, may be used to test the lack of a direct effect of sNAG nanofibers on bacterial growth or survival. In this example, *S. aureus* cultures in solution were treated with varying concentrations of sNAG nanofibers for three hours, cultures were then plated overnight at 37° C. and bacterial CFU/ml determined. As shown in FIG. 11E, no effect on bacterial growth or survival was observed.

The inventors of the present invention have found that sNAG nanofibers can stimulate expression of defensins, which may boost the innate anti-bacterial response. It is widely accepted that defensins are important players in innate immunity and function in anti-bacterial activities. As demonstrated in the examples presented in Sections 6.1 and 6.2, infra, the inventors of the present invention have found that sNAG nanofibers can increase the expression of both α- and β-type defensins in endothelial cells and β-type defensins in keratinocytes in vitro and in a wound healing model in vivo.

Further, as demonstrated in the examples presented in Sections 6.1 and 6.2, infra, but without being bound by any specific mechanism of action, Akt1 appears to be important for sNAG-dependent defensin expression in vitro and in vivo, in a wound healing model. Consistently, sNAG treatment decreased bacterial infection of cutaneous wounds infected with *Staphylococcus aureus* in wild type control animals but not in similarly treated Akt1 null animals.

The inventors of this invention have also found that a number of Toll-like receptors can be up-regulated by sNAG treatment of human endothelial cells. Toll-like receptors ("TLRs" or "TLR") are highly conserved receptors that recognize specific molecular patterns of bacterial components leading to activation of innate immunity. Recent work has linked human defensin expression to TLR activation. In particular, stimulation of TLRs can lead to increased defensin synthesis. Thus, without being bound by any mechanism of action, sNAG nanofibers may act as a stimulator of innate immunity and bacterial clearance via the activation of Akt1.

Accordingly, described herein is the use of sNAG nanofibers as a novel method for preventing and/or treating bacterial infections and diseases associated therewith. In certain embodiments, treatment of bacterial infections with sNAG nanofibers decreases the bacterial load in patients. In specific embodiments, the use of sNAG nanofibers enhances wound closure while simultaneously eradicating, decreasing or preventing bacterial infection of the wound.

5.1 sNAG Nanofibers

Described herein are sNAG nanofiber compositions. The sNAG nanofibers comprise fibers of poly-N-acetylglucosamine and/or a derivative(s) thereof, the majority of which are less than 30 microns in length and at least 1 micron in length as measured by any method known to one skilled in the art, for example, by scanning electron microscopy ("SEM"). Such sNAG nanofibers may be obtained, for example, as described herein.

In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are less than about 30, 25, 20, 15, 12, 10, 9, 8, 7, 6, 5, 4, or 3 microns in length, and at least 1 micron in length as measured by any method known to one skilled in the art, for example, by SEM. In specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are less than about 15 microns or less than about 12 microns in length, and at least 1 micron in length as measured by any method known to one skilled in the art, for example, by SEM. In specific embodiments, all (100%) of the sNAG nanofibers are less than about 15 microns in length, and at least 1 micron in length as measured by any method known to one skilled in the art, for example, by SEM. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are equal to or less than 14, 13, 12, 11, 10, 9, 8 or 7 microns in length, and at least 1 micron in length as measured by any method known to one skilled in the art, for example, by SEM. In some embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between 1 to 15, 2 to 15, 2 to 14, 1 to 12, 2 to 12, 1 to 10, 2 to 10, 3 to 12, 3 to 10, 1 to 9, 2 to 9, 3 to 9, 1 to 8, 2 to 8, 3 to 8, 4 to 8, 1 to 7, 2 to 7, 3 to 7, 4 to 7, 1 to 6, 1 to 5, 1 to 4, or 1 to 3 microns in length as measured by any method known to one skilled in the art, for example, by SEM.

In a specific embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are about 8, 7, 6, 5, 4, 3 or 2 microns in length as measured by any method known to one skilled in the art, for example, by SEM. In another specific embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between about 2 to about 10 microns, about 3 to about 8 microns, or about 4 to about 7 microns in length as measured by any method known to one skilled in the art, for example, by SEM. In another specific embodiment, all (100%) of the sNAG nanofibers are between about 2 to about 10 microns, about 3 to about 8 microns, or about 4 to about 7 microns in length as measured by any method known to one skilled in the art, for example, by SEM.

In certain embodiments, the sNAG nanofibers fibers are in a range between 0.005 to 5 microns in thickness and/or diameter as determined by electron microscopy. In specific embodiments, the sNAG nanofibers are about 0.01, 0.02, 0.03, 0.04, 0.05, 0.06, 0.07, 0.08, 0.09, 0.1, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, 2, 2.2, 2.4, 2.6, 2.8, 3 or 4 microns in thickness and/or diameter on average, or any range in between (e.g., 0.02 to 2 microns, 0.02 to 1 microns, 0.02 to 0.75 microns, 0.02 to 0.5 microns, 0.02 to 0.5 microns, 0.05 to 1 microns, 0.05 to 0.75 microns, 0.05 to 0.5 microns, 0.1 to 1 microns, 0.1 to 0.75 microns, 0.1 to 0.5 microns, etc.). In specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.02 to 1 microns. In other specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.05 to 0.5 microns. In specific embodiments, all (100%) of the sNAG nanofibers have a thickness or diameter of about 0.02 to 1 microns or about 0.05 to 0.5 microns. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.02 to 2 microns, 0.02 to 1 microns, 0.02 to 0.75 microns, 0.02 to 0.5 microns, 0.02 to 0.5 microns, 0.05 to 1 microns, 0.05 to 0.75 microns, 0.05 to 0.5 microns, 0.1 to 1 microns, 0.1 to 0.75 microns, or 0.1 to 0.5 microns.

In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between 1 and 15 microns in length and have a thickness or diameter of about 0.02 to 1 microns.

In certain embodiments, the molecular weight of the sNAG nanofibers is less than 100 kDa, 90 kDa, 80 kDa, 75 kDa, 70 kDa, 65 kDa, 60 kDa, 55 kDa, 50 kDa, 45 kDA, 40 kDa, 35 kDa, 30 kDa, or 25 kDa. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight of less than 100 kDa, 90 kDa, 80 kDa, 75 kDa, 70 kDa, 65 kDa, 60 kDa, 55 kDa, 50 kDa, 45 kDA, 40 kDa, 35 kDa, 30 kDa, or 25 kDa. In other embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight between about 5 kDa to 100 kDa, about 10 kDa to 100 kDa, about 20 kDa to 100 kDa, about 10 kDa to 80 kDa, about 20 kDa to 80 kDa, 20 kDa to 75 kDa, about 25 kDa to about 75 kDa, about 30 kDa to about 80 kDa, about 30 kDa to about 75 kDa, about 40 kda to about 80 kDa, about 40 kDa to about 75 kDa, about 40 kDa to about 70 kDa, about 50 kDa to about 70 kDa, or about 55 kDa to about 65 kDa. In one embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight of about 60 kDa.

In certain embodiments, 1% to 5%, 5% to 10%, 5% to 15%, 20% to 30% or 25% to 30% of the sNAG nanofibers are deacetylated. In some embodiments, 1%, 5%, 10%, 15%, 20%, 25%, or 30% of the sNAG nanofibers are deacetylated. In other embodiments, less than 30%, 25%, 20%, 15%, 10%, 5%, 4%, 3%, 2% or 1% of the sNAG nanofibers are deacetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the sNAG nanofibers are deacetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the sNAG nanofibers are deacetylated.

In certain embodiments, 70% to 80%, 75% to 80%, 75% to 85%, 85% to 95%, 90% to 95%, 90% to 99% or 95% to 100% of the sNAG nanofibers are acetylated. In some embodiments, 70%, 75%, 80%, 85%, 90%, 95%, 98%, 99% or 100% of the sNAG nanofibers are acetylated. In other embodiments, more than 70%, 75%, 80%, 85%, 90%, 95%, 98%, 99%, 99.5% or 99.9% of the sNAG nanofibers are acetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the sNAG nanofibers are acetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the sNAG nanofibers are acetylated.

In some embodiments, the sNAG nanofibers comprise at least one glucosamine monosaccharide, and may further comprise at least 10%, 20%, 30%, 40%, 50%, 60%, 70%, 80%, 90%, 95% or 99% of the N-acetylglucosamine monosaccharides. In other embodiments, the sNAG nanofibers comprise at least one N-acetylglucosamine monosaccharide, and may further comprise at least 10%, 20%, 30%, 40%, 50%, 60%, 70%, 80%, 90%, 95% or 99% of glucosamine monosaccharides.

In one aspect, the sNAG nanofibers increase the metabolic rate of serum-starved human umbilical cord vein endothelial cells ("EC") in a MTT assay. A MTT assay is a laboratory test and a standard colorimetric assay (an assay which measures changes in color) for measuring cellular proliferation (cell growth). Briefly, yellow MTT (3-(4,5-Dimethylthiazol-2-yl)-2,5-diphenyltetrazolium bromide, a tetrazole) is reduced to purple formazan in the mitochondria of living cells. This reduction takes place only when mitochondrial reductase enzymes are active, and therefore conversion can be directly related to the number of viable (living) cells. The metabolic rate of cells may be determined by other techniques commonly known to the skilled artisan.

In another aspect, the sNAG nanofibers do not rescue apoptosis of serum-starved EC in a trypan blue exclusion test. A trypan blue exclusion test is a dye exclusion test used to determine the number of viable cells present in a cell suspension. It is based on the principle that live cells possess intact cell membranes that exclude certain dyes, such as trypan blue, Eosin, or propidium, whereas dead cells do not. The viability of cells may be determined by other techniques commonly known to the skilled artisan.

In certain embodiments, compositions comprising the sNAG nanofibers are described, wherein the sNAG nanofibers increase the metabolic rate of serum-starved human umbilical cord vein endothelial cells in a MTT assay and/or do not rescue apoptosis of serum-starved human umbilical cord vein endothelial cells in a trypan blue exclusion test. In some embodiments, the sNAG nanofibers increase the metabolic rate of serum-starved human umbilical cord vein endothelial cells in a MTT assay and do not rescue apoptosis of serum-starved human umbilical cord vein endothelial cells in a trypan blue exclusion test.

In a specific embodiment, the sNAG nanofibers are biocompatible. Biocompatibility may be determined by a variety of techniques, including, but not limited to such procedures as the elution test, intramuscular implantation, or intracutaneous or systemic injection into animal subjects. Such tests are described in U.S. Pat. No. 6,686,342 (see, e.g., Example 10), which is incorporated by reference herein in its entirety.

In certain embodiments, the sNAG nanofibers used in the methods described herein are non-reactive in a biocompatibility test or tests. For example, the sNAG nanofibers used in the methods described herein may be non-reactive when tested in an elution test, an intramuscular implantation test, an intracutaneous test, and/or a systemic test. In other embodiments, the sNAG nanofibers used in the methods described herein have Grade 0 or Grade 1 test score when tested in an elution test, an intramuscular implantation test, an intracutaneous test, or a systemic test. In yet another embodiment, the sNAG nanofibers used in the methods described herein are at most mildly reactive when tested in an elution test, an intramuscular implantation test, an intracutaneous test, and/or a systemic test. In certain embodiments, the compositions described herein do not cause an allergenic reaction or an irritation. In other embodiments, the compositions described herein cause at most a mild allergenic reaction or a mild irritation, e.g., at the site of application. The relevant tests and evaluation of test results are described in, e.g., U.S. Pat. No. 6,686,342, which is incorporated herein by reference in its entirety, and in Section 6.8, infra.

In a specific embodiment, the sNAG nanofibers are non-reactive when tested in an intramuscular implantation test. In one aspect, an intramuscular implantation test is an intramuscular implantation test—ISO 4 week implantation, as described in Section 6.8.3, infra. In certain embodiments, the sNAG nanofibers display no biological reactivity as determined by an elution test (Elution Test Grade=0). In some embodiments, the sNAG nanofibers have a test score equal to "0" and/or are at most a negligible irritant as determined by intracutaneous injection test. In some embodiments, the sNAG nanofibers elicit no intradermal reaction (i.e., Grade I reaction) in Kligman test and/or have a weak allergenic potential as determined by Kligman test.

In certain aspects, the sNAG nanofibers are immunoneutral (i.e., they do not elicit an immune response).

In some embodiments, the sNAG nanofibers are biodegradable. The sNAG nanofibers preferably degrade within about 1 day, 2 days, 3 days, 5 days, 7 days (1 week), 8 days, 10 days, 12 days, 14 days (2 weeks), 17 days, 21 days (3 weeks), 25 days, 28 days (4 weeks), 30 days, 1 month, 35 days, 40 days, 45 days, 50 days, 55 days, 60 days, 2 months, 65 days, 70 days, 75 days, 80 days, 85 days, 90 days, 3 months, 95 days, 100 days or 4 months after administration or implantation into a patient.

In certain embodiments, the sNAG nanofibers do not cause a detectable foreign body reaction. A foreign body reaction, which may occur during wound healing, includes accumulation of exudate at the site of injury, infiltration of inflammatory cells to debride the area, and the formation of granulation tissue. The persistent presence of a foreign body can inhibit full healing. Rather than the resorption and reconstruction that occurs in wound healing, the foreign body reaction is characterized by the formation of foreign body giant cells, encapsulation of the foreign object, and chronic inflammation. Encapsulation refers to the firm, generally avascular collagen shell deposited around a foreign body, effectively isolating it from the host tissues. In one embodiment, treatment of a site (e.g., a wound or a site of a bacterial infection in a wound) with the sNAG nanofibers does not elicit a detectable foreign body reaction in 1 day, 3 days, 5 days, 7 days, 10 days or 14 days after treatment. In one such embodiment, treatment of a site (e.g., a wound) with the sNAG nanofibers does not elicit a foreign body encapsulations in 1 day, 3 days, 5 days, 7 days, 10 days or 14 days after treatment.

In some embodiments, the sNAG nanofibers (i) comprise fibers, wherein majority of the fibers are between about 1 and 15 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In certain embodiments, the sNAG nanofibers (i) comprise fibers, wherein majority of the fibers are between about 1 and 12 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In certain embodiments, the sNAG nanofibers (i) comprise fibers, wherein majority of the fibers are between about 4 and 7 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test.

In certain embodiments, the sNAG nanofibers do not have a direct effect on the growth or survival of bacteria, such as *S. aureus*, as determined by one skilled in the art. In other embodiments, sNAG nanofibers do not have a direct effect on the growth or survival of bacteria, such as *S. aureus*, as determined by the methods set forth in Section 6.2.2.5, infra. In some embodiments, the sNAG nanofibers do not have a direct effect in vitro on bacterial growth or survival. In one embodiment, the sNAG nanofibers do not have a direct effect (e.g., in vitro) on growth or survival of gram-negative bacteria. In another embodiment, the sNAG nanofibers do not have a direct effect (e.g., in vitro) on growth or survival of gram-positive bacteria. In yet another embodiment, the sNAG nanofibers do not have a direct effect (e.g., in vitro) on growth or survival of either gram-positive or gram-negative bacteria. In some embodiments, the sNAG nanofiber or a sNAG nanofiber composition does not bind bacteria (e.g., gram-positive bacteria, gram-negative bacteria, or both types of bacteria). In some embodiments, incubation of a bacterial culture with the sNAG nanofibers (e.g., 50-500 µg of sNAG nanofibers) in vitro does not reduce bacterial load in 10 minutes, 30 minutes, 1 hour, 2 hours, 3 hours, 6 hours, 12 hours, 24 hours, 48 hours, 72 hours or 96 hours of incubation (wherein the bacterial culture may be gram-positive and/or a gram-negative). In some embodiments, incubation of a *S. aureus* culture with sNAG nanofibers (e.g., about 80 µg-300 µg, or about 100-200 µg of sNAG naofibers) in vitro does not reduce bacterial load in 2 hours, 3 hours, 6 hours or 24 hours of incubation. In yet other embodiments, the sNAG nanofibers reduce bacterial growth or survival in vitro by less than 1 log, 0.9 log, 0.8 log, 0.75 log, 0.7 log, 0.6 log, 0.5 log, 0.4 log, 0.3 log, 0.25 log, 0.2 log, 0.1 log, 0.05 log, or 0.025 log, for example, when *Staphylococcus aureus* bacterial cultures are treated/incubated with the sNAG nanofibers in vitro. In some embodiments, the sNAG nanofibers reduce bacterial growth or survival in vitro by less than $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ cfu/ml, for example, when *Staphylococcus aureus* bacterial cultures are treated/incubated with the sNAG nanofibers in vitro. The tests of the effect of sNAG nanofibers on bacterial growth or survival and the evaluation of the test results are described, for example, in Example 2 (e.g., Section 6.2.2.5) and FIG. 11E, infra.

In some embodiments, the sNAG nanofibers (i) comprise fibers, wherein majority of the fibers are between about 1 and 15 microns, 1 and 12 microns, or 4 and 7 microns in length, (ii) do not have an effect on bacterial growth or survival of *Staphylococcus aureus* bacterial cultures in vitro, and (iii) are non-reactive when tested in a biocompatibility test (e.g., an intramuscular implantation test).

In certain embodiments, the sNAG nanofibers induce a certain pattern of gene expression (RNA or protein expression as determined by, e.g., RT-PCR, microarray or ELISA) in a cell, tissue or organ treated with or exposed to a sNAG nanofiber composition. Specifically, in some embodiments, the sNAG nanofibers or a composition comprising the sNAG nanofibers induce expression of one or more defensin proteins, one or more defensin-like proteins, and/or one or more Toll-like receptors. In yet other embodiments, the sNAG nanofibers or a composition comprising the sNAG nanofibers induce expression of one or more proteins that are known to have an anti-bacterial effect.

In certain embodiments, the sNAG nanofibers or a composition comprising the sNAG nanofibers induce expression of one or more α-defensins (e.g., DEFA1 (i.e., α-defensin 1), DEFA1B, DEFA3, DEFA4, DEFA5, DEFA6), one or more β-defensins (e.g., DEFB1 (i.e., β-defensin 1), DEFB2, DEFB4, DEFB103A, DEFB104A, DEFB105B, DEFB107B, DEFB108B, DEFB110, DEFB112, DEFB114, DEFB118, DEFB119, DEFB123, DEFB124, DEFB125, DEFB126, DEFB127, DEFB128, DEFB129, DEFB131, DEFB136), and/or one or more θ-defensins (e.g., DEFT1P). In some embodiments, the sNAG nanofibers or a composition comprising the sNAG nanofibers induce expression of one or more of DEFA1, DEFA3, DEFA4, DEFA5, DEFB1, DEFB3, DEFB103A, DEFB104A, DEFB108B, DEFB112, DEFB114, DEFB118, DEFB119, DEFB123, DEFB124, DEFB125, DEFB126, DEFB128, DEFB129 and DEFB131. In certain embodiments, the sNAG nanofibers or a composition comprising the sNAG nanofibers induce expression of one or more Toll receptors (e.g., TLR1, TLR2, TLR3, TLR4, TLR5, TLR6, TLR7, TLR8, TLR9, TLR10, TLR11, and/or TLR12). In other embodiments, the sNAG nanofibers or a composition comprising the sNAG nanofibers induce expression of one or more of IL-1, CEACAM3, SPAG11, SIGIRR (IL1-like receptor), IRAK1, IRAK2, IRAK4, TBK1, TRAF6 and IKKi. In some embodiments, the sNAG nanofibers or a composition comprising the sNAG nanofibers induce expression of one or more of IRAK2, SIGIRR, TLR1, TLR2, TLR4, TLR7, TLR8, TLR10 and TRAF6. In one embodiment, the sNAG nanofibers or a composition comprising the sNAG nanofibers induce expression of at least one of the above-listed gene products.

In some embodiments, the sNAG nanofibers or a composition comprising the sNAG nanofibers induce expression of one or more of the above-listed genes in the amount equal to or more than about 0.25 fold, 0.5 fold, 1 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 12 fold, 15 fold or 20 fold as compared to the level of expression of the one or more of the above-listed genes in a cell, tissue or organ of a subject before treatment with the sNAG nanofibers (e.g., a known average level of expression of the one or more of the above-listed genes). In some embodiments, the sNAG nanofibers or a composition comprising the sNAG nanofibers induce expression of one or more of the above-listed genes in the amount equal to or more than about 10%, 25%, 50%, 75%, 100%, 125%, 150%, 175%, 200%, 225%, 250%, 275%, 300%, 350%, 400%, 450%, 500%, 550%, 600%, 650%, 700%, 750%, 800%, 900% or 1000% the level of expression of the one or more of the above-listed genes in a cell, tissue or organ of a subject before treatment with the sNAG nanofibers (e.g., a known average level of expression of the one or more of the above-listed genes).

In some embodiments, the sNAG nanofibers but not long poly-N-acetylglucosamine, chitin and/or chitosan induce expression of the one or more genes listed above, as determined by a method known to one skilled in the art, or described herein. In some of these embodiments, long poly-N-acetylglucosamine, chitin and/or chitosan do not induce expression of the one or more genes listed above or induce lower level (e.g., more than 1.25 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold lower) of expression of the one or more genes listed above as compared to the level of expression of the one or more genes listed above induced by the sNAG nanofibers, as determined by a method known to one skilled in the art, or described herein.

In certain embodiments, the sNAG nanofibers or a composition comprising the sNAG nanofibers induce a gene expression profile that is consistent with, similar to, about the same as, or equivalent to one or more gene expression profiles demonstrated in Tables I, II, III, V, VIII and IX, Sections 6.2-6.5, infra. In some embodiments, the sNAG nanofibers or a composition comprising the sNAG nanofibers induce expression of one or more of the genes shown to be upregulated by sNAG treatment in Tables I, II, III, V, VIII and IX, Sections 6.2-6.5, infra. In some embodiments, the sNAG nanofibers or a composition comprising the sNAG nanofibers induce expression of the majority or all of the genes shown to be upregulated by sNAG treatment in Tables I, II, III, V, VIII and IX, Sections 6.2-6.5, infra. In some of these embodiments, gene expression levels are measured at 1 hour, 2 hours, 4 hours, 5 hours, 6 hours, 8 hours, 10 hours, 12 hours, 14 hours, 16 hours, 18 hours, 20 hours, 24 hours, 48 hours, 3 days or 5 days after treatment of a cell, tissue or organ with a sNAG nanofiber composition by a method known to one skilled in the art, or described herein.

In certain embodiments, the sNAG nanofibers or a composition comprising the sNAG nanofibers induce a gene expression profile that differs from the profile induced by long poly-N-acetylglucosamine polymers or fibers. In specific embodiments, a gene expression profile induced by the sNAG nanofibers is consistent with, similar to, about the same as, or equivalent to that shown in Tables I, II, III, V, VIII and IX, Sections 6.2-6.5, infra, whereas gene expression profile induced by long poly-N-acetylglucosamine polymers or fibers is consistent with, similar to, about the same with, or equivalent to that shown in Table VIII and/or IX, Section 6.5, infra. In other embodiments, the sNAG nanofibers or a composition comprising the sNAG nanofibers induce a gene expression profile that differs from the gene expression profile induced by chitin or chitosan.

In a specific embodiment, the sNAG nanofibers are obtained by irradiating poly-N-acetylglucosamine and/or a derivative thereof. See Section 5.1.1, infra, regarding poly-N-acetylglucosamine and derivatives thereof and Section 5.2, infra, regarding methods for producing the sNAG nanofibers using irradiation. Irradiation may be used to reduce the length of poly-N-acetylglucosamine fibers and/or poly-N-acetylglucosamine derivative fibers to form shortened poly-$\beta$-1→4-N-acetylgulcosamine fibers and/or shortened poly-N-acetylglucosamine derivative fibers, i.e. sNAG nanofibers. Specifically, irradiation may be used to reduce the length and molecular weight of poly-N-acetylglucosamine or a derivative thereof without disturbing its microstructure. The infrared spectrum (IR) of sNAG nanofibers is similar to, about the same as, or equivalent to that of the non-irradiated poly-$\beta$-1→4-N-acetylgulcosamine or a derivative thereof.

In one embodiment, the sNAG nanofibers are not derived from chitin or chitosan. Whereas in another embodiment, the compositions described herein may be derived from chitin or chitosan, or the sNAG nanofibers may be derived from chitin or chitosan.

5.1.1 Poly-N-Acetylglucosamine and Derivatives Thereof

U.S. Pat. Nos. 5,622,834; 5,623,064; 5,624,679; 5,686,115; 5,858,350; 6,599,720; 6,686,342; 7,115,588 and U.S. Patent Pub. 2009/0117175 (each of which is incorporated herein by reference) describe the poly-N-acetylglucosamine and derivatives thereof, and methods of producing the same. In some embodiments, the poly-N-acetylglucosamine has a $\beta$-1→4 configuration. In other embodiments, the poly-N-acetylglucosamine has a $\alpha$-1→4 configuration. The poly-N-acetylglucosamine and derivatives thereof may be in the form of a polymer or in the form of a fiber.

Poly-N-acetylglucosamine can, for example, be produced by, and may be purified from, microalgae, preferably diatoms. The diatoms which may be used as starting sources for the production of the poly-N-acetylglucosamine include, but are not limited to members of the Coscinodiscus genus, the *Cyclotella* genus, and the *Thalassiosira* genus. Poly-N-acetylglucosamine may be obtained from diatom cultures via a number of different methods, including the mechanical force method and chemical/biological method known in the art (see, e.g., U.S. Pat. Nos. 5,622,834; 5,623,064; 5,624,679; 5,686,115; 5,858,350; 6,599,720; 6,686,342; and 7,115,588, each of which is incorporated herein by reference in its entirety). In certain embodiments, the poly-N-acetylglucosamine is not derived from one or more of the following: a shell fish, a crustacean, an insect, a fungi or yeasts.

In one embodiment, poly-$\beta$-1→4-N-acetylglucosamine is derived from a process comprising a) treating a microalgae comprising a cell body and a poly-$\beta$-1→4-N-acetylglucosamine polymer fiber with a biological agent (such as hydrofluoric) capable of separating the N-acetylglucosamine polymer fiber from the cell body for a sufficient time so that the poly-$\beta$-1→4-N-acetylglucosamine polymer fiber is released from the cell body; b) segregating the poly-$\beta$-1→4-N-acetylglucosamine polymer fiber from the cell body; and c) removing contaminants from the segregated poly-$\beta$-1→4-N-acetylglucosamine polymer fiber, so that the poly-$\beta$-1→4-N-acetylglucosamine polymer is isolated and purified.

In other embodiments, the poly-β-1→4-N-acetylglucosamine may be derived from one or more of the following: a shell fish, a crustacean, an insect, a fungi or yeasts. In certain embodiments, the compositions described herein do not comprise chitin or chitosan.

One or more of the monosaccharide units of the poly-N-acetylglucosamine may be deacetylated. In certain embodiments, 1% to 5%, 5% to 10%, 5% to 15%, 20% to 30% or 25% to 30% of the poly-N-acetylglucosamine is deacetylated. In some embodiments, 1%, 5%, 10%, 15%, 20%, 25%, or 30% of the poly-N-acetylglucosamine is deacetylated. In other embodiments, less than 30%, 25%, 20%, 15%, 10%, 5%, 4%, 3%, 2% or 1% of the poly-N-acetylglucosamine is deacetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the poly-N-acetylglucosamine is deacetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the poly-N-acetylglucosamine is deacetylated.

In certain embodiments, a poly-N-acetylglucosamine composition comprises 70% to 80%, 75% to 80%, 75% to 85%, 85% to 95%, 90% to 95%, 90% to 99% or 95% to 100% of acetylated glucosamine (i.e., N-acetylglucosamine) monosaccharides. In some embodiments, a poly-N-acetylglucosamine composition comprises 70%, 75%, 80%, 85%, 90%, 95%, 98%, 99% or 100% of acetylated glucosamine (i.e., N-acetylglucosamine) monosaccharides. In other embodiments, a poly-N-acetylglucosamine composition comprises more than 70%, 75%, 80%, 85%, 90%, 95%, 98%, 99%, 99.5% or 99.9% of the acetylated glucosamine. In some embodiments, a poly-N-acetylglucosamine composition comprises equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the acetylated glucosamine. In other embodiments, a poly-N-acetylglucosamine composition comprises less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the acetylated glucosamine.

In some embodiments, a poly-N-acetylglucosamine composition comprises at least one glucosamine monosaccharide, and may further comprise at least 10%, 20%, 30%, 40%, 50%, 60%, 70%, 80%, 90%, 95% or 99% of N-acetylglucosamine monosaccharides. In other embodiments, a poly-N-acetylglucosamine composition comprises at least one N-acetylglucosamine monosaccharide, and may further comprise at least 10%, 20%, 30%, 40%, 50%, 60%, 70%, 80%, 90%, 95% or 99% of glucosamine monosaccharides.

Derivatives of poly-N-acetylglucosamine may also be used in a composition described herein. Derivatives of poly-N-acetylglucosamine and methods of making such derivatives are described in U.S. Pat. No. 5,623,064 (see, e.g., Section 5.4), which is incorporated by reference herein in its entirety. Derivatives of poly-N-acetylglucosamine may include, but are not limited to, partially or completely deacetylated poly-N-acetylglucosamine, or its deacetylated derivatives. Further, poly-N-acetylglucosamine may bederivatized by being sulfated, phosphorylated and/or nitrated. Poly-N-acetylglucosamine derivatives include, e.g., sulfated poly-N-acetylglucosamine derivatives, phosphorylated poly-N-acetylglucosamine derivatives, or nitrated poly-N-acetylglucosamine derivatives. Additionally, one or more of the monosaccharide units of the poly-N-acetylglucosamine may contain one or more sulfonyl groups one or more O-acyl groups. In addition, one or more of the monosaccharides of the deacetylated poly-N-acetylglucosamine may contain an N-acyl group. One or more of the monosaccharides of the poly-N-acetylglucosamine or of its deacetylated derivative, may contain an O-alkyl group. One or more of the monosaccharide units of the poly-N-acetylglucosamine may be an alkali derivative. One or more of the monosaccharide units of the deacetylated derivative of poly-N-acetylglucosamine may contain an N-alkyl group. One or more of the monosaccharide units of the deacetylated derivative of poly-N-acetylglucosamine may contain at least one deoxyhalogen derivative. One or more of the monosaccharide units of the deacetylated derivative of poly-N-acetylglucosamine may form a salt. One or more of the monosaccharide units of the deacetylated derivative of poly-N-acetylglucosamine may form a metal chelate. In a specific embodiment, the metal is zinc. One or more of the monosaccharide units of the deacetylated derivative of poly-N-acetylglucosamine may contain an N-alkylidene or an N-arylidene group. In one embodiment, the derivative is an acetate derivative. In another embodiment, the derivative is not an acetate derivative. In one embodiment the poly-N-acetylglucosamine or deacetylated poly-N-acetylglucosamine is derivatized with lactic acid. Wherein, in another embodiment, the derivative is not derivatized with lactic acid.

5.2 Methods of Making sNAG Nanofibers

The poly-N-acetylglucosamine polymers or fibers, and any derivatives of poly-N-acetylglucosamine polymers or fibers described above, can be irradiated as dry polymers or fibers or polymer or fiber membranes. Alternatively, poly-N-acetylglucosamine polymers or fibers, and any derivatives of poly-N-acetylglucosamine polymers or fibers described above, can be irradiated when wet. The methods of making sNAG nanofibers by irradiation and the sNAG nanofibers so produced have been described in U.S. Patent Pub. No. 2009/0117175, which is incorporated by reference herein in its entirety.

In certain embodiments, the poly-N-acetylglucosamine polymers or fibers are formulated into a suspension/slurry or wet cake for irradiation. Irradiation can be performed prior to, concurrently with or following the formulation of the polymers or fibers into its final formulation, such as a dressing. Generally, the polymer or fiber content of suspensions/slurries and wet cakes can vary, for example from about 0.5 mg to about 50 mg of polymer or fiber per 1 ml of distilled water are used for slurries and from about 50 mg to about 1000 mg of polymer or fiber per 1 ml of distilled water are use for wet cake formulations. The polymer or fiber may first be lyophilized, frozen in liquid nitrogen, and pulverized, to make it more susceptible to forming a suspension/slurry or wet cake. Also, the suspensions/slurries can be filtered to remove water such that a wet cake is formed. In certain aspects, the polymer or fiber is irradiated as a suspension comprising about 0.5 mg, 1 mg, 2 mg, 3 mg, 4 mg, 5 mg, 6 mg, 7 mg, 8 mg, 9 mg, 10 mg, 12 mg, 15 mg, 18 mg, 20 mg, 25 mg or 50 mg of polymer or fiber per ml of distilled water, or any range in between the foregoing embodiments (e.g., 1-10 mg/ml, 5-15 mg/ml, 2-8 mg/ml, 20-50 mg/ml, etc.). In other aspects, the polymer or fiber is irradiated as a wet cake, comprising about 50-1,000 mg polymer or fiber per 1 ml of distilled water. In specific embodiments, the wet cake comprises about 50, 100, 200, 300, 400, 500, 600, 700, 800, 900 or 1000 mg of polymer or fiber per 1 ml distilled water, or any range in between (e.g., 100-500 mg/ml, 300-600 mg/ml, 50-1000 mg/ml, etc.).

The irradiation is preferably in the form of gamma radiation, e-beam radiation, or x-rays. Two sources of irradiation are preferred: radioactive nuclides and electricity. In specific embodiment, the radioactive nuclides are cobalt-60 and cesium-137. Both of these nuclides emit gamma rays, which are photons containing no mass. The gamma rays have energies from 0.66 to 1.3 MeV. Using electricity, electrons are generated and accelerated to energies up to 10 MeV or higher. When irradiating polymers or fibers to reduce their size, a consideration to take into account is that the depth of penetration of materials with densities similar to water by 10 MeV electrons is limited to about 3.7 cm with one-sided exposure or about 8.6 cm with two-sided exposure. Depth of penetration decreases at lower electron energies. Electron energy can be converted to x-rays by placing a metal (usually tungsten or tantalum) target in the electron beam path. Conversion to x-rays is limited to electrons with energies up to 5 MeV. X-rays are photons with no mass and can penetrate polymers or fibers similar to gamma rays. There is only about 8% efficiency in the conversion of electron energy to x-ray energy. High powered electron beam machines are needed in x-ray production facilities to account for the low conversion efficiency.

In a specific embodiment, the irradiation is gamma irradiation.

The absorbed dose of radiation is the energy absorbed per unit weight of product, measured in gray (gy) or kilogray (kgy). For dried polymers or fibers, the preferred absorbed dose is about 500-2,000 kgy of radiation, most preferably about 750-1,250 kgy or about 900-1,100 kgy of radiation. For wet polymers or fibers, the preferred absorbed dose is about 100-500 kgy of radiation, most preferably about 150-250 kgy or about 200-250 kgy of radiation.

The dose of radiation can be described in terms of its effect on the length of the polymers or fibers. In specific embodiments, the dose of radiation used preferably reduces the length of the polymer or fiber by anywhere from about 10% to 90% of the starting length of the polymer or fiber, respectively. In specific embodiments, the average length is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the length of the polymer or fiber to anywhere from 1 to 100 microns. In specific embodiments, and depending on the starting fiber length, the average length of the polymer or fiber is reduced to less than about 15 microns, less than about 14 microns, less than about 13 microns, less than about 12 microns, less than about 11 microns, less than about 10 microns, less than about 8 microns, less than about 7 microns, less than about 5 microns, less than about 4 microns, less than about 3 microns, less than 2 microns, or less than 1 microns. In certain embodiments, the length of the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the polymers or fibers is reduced to no greater than about 20 microns, no greater than about 15 microns, no greater than about 12 microns, no greater than about 10 microns, no greater than about 8 microns, no greater than about 7 microns, or no greater than about 5 microns. In certain embodiments, irradiation of the polymers or fibers reduces the length of the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to anywhere between about 1 to 20 microns, between about 1 to 15 microns, between about 2 to 15 microns, between about 1 to 12 microns, between about 2 to 12 microns, between about 1 to 10 microns, between about 2 to 10 microns, between about 1 to 8 microns, between about 2 to 8 microns, between about 1 to 7 microns, between about 2 to 7 microns, between about 3 to 8 microns, between about 4 to 7 microns, between about 1 to 5 microns, between about 2 to 5 microns, between about 3 to 5 microns, between about 4 to 10 microns, or any ranges between the foregoing lengths, which are also encompassed.

The dose of radiation can also be described in terms of its effect on the molecular weight of the polymer or fiber. In specific embodiments, the dose of radiation used preferably reduces the molecular weight of the polymer or fiber by anywhere from about 10% to 90% of the starting weight of the polymer or fiber. In specific embodiments, the average molecular weight is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the molecular weight of the polymer or fiber to anywhere from 1,000 to 1,000,000 daltons. In specific embodiments, and depending on the starting molecular weight, the average molecular weight of the polymer or fiber is reduced to less than 1,000,000 daltons, less than 750,000 daltons, less than 500,000 daltons, less than 300,000 daltons, less than 200,000 daltons, less than 100,000 daltons, less than 90,000 daltons, less than 80,000 daltons, less than 70,000 daltons, less than 60,000 daltons, less than 50,000 daltons, less than 25,000 daltons, less than 10,000 daltons, or less than 5,000 daltons. In certain embodiments, the average molecular weight is reduced to no less than 500 daltons, no less than 1,000 daltons, no less than 2,000 daltons, no less 3,500 daltons, no less than 5,000 daltons, no less than 7,500 daltons, no less than 10,000 daltons, no less than 25,000 daltons, no less than 50,000 daltons, no less than 60,000 daltons or no less than 100,000 daltons. Any ranges between the foregoing average molecular weights are also encompassed; for example, in certain embodiments, irradiation of the polymer or fiber reduces the average molecular weight to anywhere between 10,000 to 100,000 daltons, between 1,000 and 25,000 daltons, between 50,000 and 500,000 daltons, between 25,000 and 100,000 daltons, between 30,000 and 90,000 daltons, between about 40,000 and 80,000 daltons, between about 25,000 and 75,000 daltons, between about 50,000 and 70,000 daltons, or between about 55,000 and 65,000 daltons and so on and so forth. In certain embodiments, irradiation of the polymers or fibers reduces the molecular weight of the majority and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to anywhere between about 20,000 and 100,000 daltons, about 25,000 and 75,000 daltons, about 30,000 and 90,000 daltons, about 40,000 and 80,000 daltons, about 50,000 and 70,000 daltons, or about 55,000 and 65,000 daltons. In certain embodiments, irradiation of the polymers or fibers reduces the molecular weight of the majority and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to about 60,000 daltons.

Following irradiation, slurries can be filtered and dried, and wet cakes can be dried, to form compositions (e.g., dressings and other compositions described herein) that are useful in the practice of the invention.

5.3 Compositions Comprising sNAG Nanofibers

The sNAG nanofibers may be formulated in a variety of compositions for topical administration as described herein.

A composition comprising the sNAG nanofibers may be formulated as a cream, a membrane, a film, a liquid solution, a suspension, a powder, a paste, an ointment, a suppository, a gelatinious composition, an aerosol, a gel, or a spray. In one embodiment, a composition comprising the sNAG nanofibers is formulated as an ultra-thin membrane. In some embodiments, a composition comprising the sNAG nanofibers is formulated as a dressing, a mat, or a bandage. Solid formulations suitable for solution in, or suspension in, liquids prior to administration are also contemplated. It is also possible that such compositions are incorporated in or coated on implantable devices, such as orthopedic implants (for hip, knee, shoulder; pins, screws, etc.), cardiovascular implants (stents, catheters, etc.) and the like where the antibacterial activity would be of benefit.

A composition comprising the sNAG nanofibers may include one or more of pharmaceutically acceptable excipients. Suitable excipients may include water, saline, salt solution, dextrose, glycerol, ethanol and the like, or combinations thereof. Suitable excipients also include starch, glucose, lactose, sucrose, gelatin, malt, rice, flour, chalk, silica gel, sodium stearate, glycerol monostearate, oil (including those of petroleum, animal, vegetable or synthetic origin, such as peanut oil, soybean oil, mineral oil, sesame oil and the like), talc, sodium chloride, dried skim milk, propylene, glycol and the like. In addition, a composition comprising the sNAG nanofibers may include one or more of wetting agents, emulsifying agents, pH buffering agents, and other agents. The sNAG nanofiber compositions may also be incorporated in a physiologically acceptable carrier, for example in a physiologically acceptable carrier suitable for topical application. The term "pharmaceutically acceptable" means approved by a regulatory agency of the Federal or a state government or listed in the U.S. Pharmacopeia or other generally recognized pharmacopeia for use in animals, and more particularly in humans. Examples of suitable pharmaceutical carriers are described in "Remington's Pharmaceutical Sciences" by E. W. Martin.

The final amount of the sNAG nanofibers in a composition may vary. For example, the amount of the sNAG nanofibers in a composition (e.g., prepared for administration to a patient) may be greater than or equal to about 50%, about 60%, about 70%, about 75%, about 80%, about 85%, about 90%, about 95%, about 98%, or about 99% weight by volume. In one embodiment, the amount of the sNAG nanofibers in a composition is about 95%, about 98%, about 99, or about 100%. Also, the amount of the sNAG nanofibers in a composition (e.g., prepared for administration to a patient) may be about 50%-100%, about 60%-100%, about 70%-100%, about 75%-100%, about 80%-100%, about 90%-100%, about 95%-100%, about 70%-95%, about 75%-95%, about 80%-95%, about 90%-95%, about 70%-90%, about 75%-90%, or about 80%-90% weight/volume. A composition may comprise more than 30%, 40%, 50%, 60%, 70%, 75%, 80%, 90%, 95% or 99% solution of the sNAG nanofibers.

A sNAG nanofiber composition may be formulated into a wound dressing. In certain embodiments, a sNAG nanofiber composition is formulated as a wound dressing in the form of a barrier, a membrane, or a film. Alternatively, a sNAG nanofiber composition may be added to dressing backings, such as barriers, membranes, or films. A barrier, membrane, or film can be supplied in a variety of standard sizes, which can be further cut and sized to the area being treated. The backing can be a conventional dressing material, such as a bandage or gauze to which a polymer or fiber is added or coated on, prior to application to the patient. Alternatively, the sNAG nanofibers can be formulated as a barrier, membrane, or film made out of strings, microbeads, microspheres, or microfibrils, or the composition can be formulated as a barrier-forming mat. In certain embodiments, at least 75%, at least 85%, at least 90%, or at least 95% of a dressing is composed of the sNAG nanofibers. In certain aspects, a dressing does not contain a conventional dressing material such as a gauze or bandage. In such embodiments, the sNAG nanofiber itself is formulated as a wound dressing.

A composition comprising the sNAG nanofibers may further comprise any suitable natural or synthetic polymers or fibers. Examples of suitable polymers or fibers include cellulose polymers, xanthan, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. Other suitable classes of polymers or fibers include polyvinyledene fluorides and polyacrylonitriles. Examples of these polymers or fibers include those described in U.S. Pat. Nos. RE 30,351; 4,705,540, 4,717,393; 4,717,394; 4,912,197; 4,838,900; 4,935,490; 4,851,505; 4,880,442; 4,863,496; 4,961,539; and European Patent Application 0 219 878, all of which are incorporated by reference. The polymers or fibers can include at least one of either of cellulose polymers, polyamides, polyaramides, polyamide/imides or polyimides. In certain embodiments, the polymers or fibers include polyaramides, polyester, urethan and polytetrafluoroethylene. In one embodiment, the compositions described herein comprise more than one type of polymer (e.g., the sNAG nanofiber and cellulose).

In certain aspects, the sNAG nanofiber is the only active ingredient in a composition.

In other embodiments, a composition comprises one or more additional active ingredients, e.g., to promote an anti-bacterial effect and/or healing (e.g., wound healing). In some embodiments, the additional active ingredient is one or more anti-bacterial agents (e.g., an antibiotic, a defensin peptide, a defensin-like peptide, or a Toll-receptor-like peptide), or a growth factor. In specific embodiments, the additional active ingredient is a growth factor such as one or more of PDGF-AA, PDGF-AB, PDGF-BB, PDGF-CC, PDGF-DD, FGF-1, FGF-2, FGF-5, FGF-7, FGF-10, EGF, TGF-α, (HB-EGF), amphiregulin, epiregulin, betacellulin, neuregulins, epigen, VEGF-A, VEGF-B, VEGF-C, VEGF-D, VEGF-E, placenta growth factor (PLGF), angiopoietin-1, angiopoietin-2, IGF-I, IGF-II, hepatocyte growth factor (HGF), and macrophage-stimulating protein (MSP). In other embodiments, the additional active ingredient is an agent that boost the immune system, a pain relief agent, or a fever relief agent.

In certain embodiments, the additional active ingredient is an antibiotic of one of the following classes of antibiotics: microlides (e.g., erythromycin, azithromycin), aminoglycosides (e.g., amikacin, gentamicin, neomycin, streptomycin), cephalosporins (e.g., cefadroxil, cefaclor, cefotaxime, cefepime), fluoroquinolones (e.g., ciprofloxacin, levofloxacin), penicillins (e.g., penicillin, ampicillin, amoxicillin), tetracyclines (e.g., tetracycline, doxycycline), and carbapenems (e.g., meropenem, imipenem). In some specific embodiments, the additional active ingredient is one or more of vancomycin, sulfa drug (e.g., co-trimoxazole/trimethoprim-sulfamethoxazole), tetracycline (e.g., doxycycline, minocycline), clindamycin, oxazolidinones (e.g., linezolid), daptomycin, teicoplanin, quinupristin/dalfopristin (synercid), tigecycline, allicin, bacitracin, nitrofurantoin, hydrogen peroxide, novobiocin, netilmicin, methylglyoxal, bee defensin-1, tobramycin, chlorhexidine digluconate, chlorhexidine gluconate, levofloxacin, zinc, and silver. In some embodiments, a composition comprises the sNAG nanofibers and an additional active ingredient effective to treat or prevent or commonly used to treat or prevent an *S. aures* infection, MRSA infection, a *Pseudomonas* infection, or a *C. difficile* infection (e.g., an antibiotic effective against or commonly used against such infections).

A sNAG nanofiber composition may contain collagen, although in certain aspects a sNAG nanofiber composition does not contain collagen.

In certain embodiments, a sNAG nanofiber composition does not comprise any additional therapy. In certain embodiments, a sNAG nanofiber composition does not comprise any additional anti-bacterial agent, a defensin peptide, a defensin-like peptide, a Toll-receptor-like peptide, or a growth factor. In some embodiments, a sNAG nanofiber composition does not comprise an antibiotic. In yet other embodiments, a sNAG nanofiber composition may comprise an additional therapy (e.g., an antibiotic). In one such embodiment, the additional therapy (e.g., an antibiotic) is not encapsulated, immobilized or formulated in the sNAG nanofibers.

In other aspects, a sNAG nanofiber composition does not comprise a significant amount of protein material. In specific embodiments, the protein content of a sNAG nanofiber composition is no greater than 0.1%, 0.5% or 1% by weight. In other embodiments, the protein content of the composition is undetectable by Coomassie staining.

In one embodiment, zinc is also included in a sNAG nanofiber composition. In addition to its antimicrobial properties, zinc also plays a role in wound healing (see Andrews et al., 1999, Adv Wound Care 12: 137-8). The zinc is preferably added in the form of a salt, such as zinc oxide, zinc sulphate, zinc acetate or zinc gluconate.

5.4 Anti-Bacterial Uses of sNAG Compositions

A wide variety of bacterial infections and diseases associated therewith may be treated and/or prevented by the administration of the sNAG nanofiber compositions described herein (see, e.g., Sections 5.4.1 and 5.4.2, infra). In one embodiment the compositions described herein are bacteriostatic. In another embodiment, the compositions described herein are bactericidal. In an embodiment, the compositions described herein may be used to treat and/or prevent infections by Gram-positive bacteria and/or any diseases associated therewith. In another embodiment, the compositions described herein may be used to treat and/or prevent infections by Gram-negative bacteria and/or any diseases associated therewith. In yet another embodiment, the compositions described herein may be used to treat and/or prevent infections by both Gram-negative bacteria and Gram-positive bacteria and/or any diseases associated therewith.

Bacterial infections that may be treated and/or prevented using compositions described herein include infections by bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, Edwardsiella, *Enterobacter aerogenes*, *Erwinia species*, *Escherichia coli*, *Hafnia species*, *Klebsiella species*, *Morganella species*, *Proteus vulgaris*, *Providencia*, *Salmonella* species, *Serratia marcescens*, and *Shigella flexneri*), Gardinella family, *Haemophilus influenzae*, Halobacteriaceae family, *Helicobacter* family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis*, *Streptococcus fasciae*, and *Streptococcus pneumoniae*), Vampirovibr *Helicobacter* family, and/or *Vampiro vibrio* family. In a specific embodiment, diseases caused by or associated with infections by such bacteria may also be prevented and/or treated using the compositions described herein.

Bacterial infections that may be treated and/or prevented using compositions described herein also include infections by bacteria of the following genuses: *Bordetella*, *Borrelia*, *Brucella*, *Campylobacter*, *Chlamydia* and *Clamidophylia*, *Clostridium*, *Corynebacterium*, *Enterococcus*, *Escherichia*, *Francisella*, *Haemophilus*, *Helicobacter*, *Legionella*, *Leptospira*, *Listeria*, *Mycobacterium*, *Mycoplasma*, *Neisseria*, *Pseudomonas*, *Rickettsia*, *Salmonella*, *Shigella*, *Staphylococcus*, *Streptococcus*, *Treponema*, *Vibria*, and/or *Yersinia*. In a specific embodiment, diseases caused by or associated with infections by such bacteria may also be prevented and/or treated using the compositions described herein.

Bacterial infections that may be treated and/or prevented using compositions described herein include infections by bacteria of the following species: *Bacillus anthracis*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumonia*, *Chlamydia trachomatis*, *Clamidophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitides*, *Pseudomonas aeruginosa*, *Proteus mirabilis*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumonia*, *Streptococcus pyogenes*, *Treponema pallidum*, *Vibria cholerae*, and/or *Yersinia pestis*. In a specific embodiment, diseases caused by or associated with infections by such bacteria may also be prevented and/or treated using the compositions described herein.

In some embodiments, the compositions described herein may be used to treat and/or prevent infections by aerobic bacteria and/or diseases associated therewith. In other embodiments, the compositions described herein may be used to treat and/or prevent infections by anaerobic bacteria and/or diseases associated therewith.

In certain embodiments, the compositions described herein are used to treat and/or prevent *Pseudomonas aeruginosa* infections. *Pseudomonas* is a gram-negative aerobic bacteria found in soil, water, other moist environments, plants and animals, clinical isolates of which produce the blue-green pigment pyocyanin and a characteristic sweet ordor. *Pseudomonas aeruginosa* is known to cause urinary tract infections, pneumonia, respiratory system infections, dermatitis, soft tissue infections, bacterimia, bone and joint infections, gastrointestinal infections and a variety of systemic infections. It is known to be an important cause of infections, particularly in patients with burns, patients with cystic fibrosis, patients who are immunosuppressed (e.g., AIDS and cancer patients), and in patients who have been hospitalized for longer than 1 week. It is a frequent cause of nosocomial infections such as but not limited to pneumonia, urinary tract infections and bacterimia. Any one or all of these infections may be prevented and/or treated by the compositions described herein.

In some embodiments, the compositions described herein are used to treat and/or prevent Staph infections, and particularly, *Staphylococcus aureus* infections. Use of a sNAG nanofiber composition in this embodiment and other embodiments described herein may preclude the generation of resistant organisms as well as allow for the antibiotic-independent clearance of a bacterial infection.

In certain embodiments, the compositions described herein may be used to combat bacteria that are resistant to one or more anti-bacterial agents. For example, the compositions described herein may be used to treat bacteria that are resistant to one or more antibiotics, for example resistant to conventional antibiotics such as MRSA (methicillin-resistant *Staphylococcus aureus*), VRSA (Vancomycin-resistant *S. aureus*), VRE (Vancomycin-resistant Enterococus), Penicillin-resistant *Enterococcus*, PRSP (Penicillin-resistant *Streptococcus pneumonia*), isoniazid/rifampin-resistant *Mycobacterium tuberculosis* and other antibiotic-resistant strains of bacteria (e.g., resistant strains of *E. coli, Salmonella, Campylobacter*, and Streptococci). In one embodiment, the compositions disclosed herein may be used to treat multiple drug resistant bacteria.

In some specific embodiments, the compositions described herein may be used to treat and/or prevent Methicillin-resistant *Staphylococcus aureus* ("MRSA"; it may also be called multidrug-resistant *Staphylococcus aureus* or oxacillin-resistant *Staphylococcus aureus* ("ORSA")). MRSA is any strain of *Staphylococcus aureus* that has developed resistance to beta-lactam antibiotics, which include but are not limited to the penicillins (penicillin, methicillin, dicloxacillin, nafcillin, oxacillin, etc.) and the cephasosporins. Some of the known strains of MRSA include EMRSA15 and EMRSA16 (also known as MRSA252), which are resistant to erythromycin and ciprofloxacin; CC8 (also known as ST8:USA300); ST1:USA400; ST8:USA500; ST59:USA1000; ST93 strains; ST80 strains; and ST59 strains. MRSA is responsible for a number of infections in humans. MRSA is a serious helath concern, causing approximately 50% of health-care associated staph infections. In the U.S., more than 94,000 people develop serious MRSA infection and about 19,000 die from infection each year. Especially prevalent MRSA is in hospitals; where risk factors for MRSA infection include prior antibiotic exposure (e.g., quinolone antibiotics), admission to an intensive care unit, surgery and exposure to an MRSA-colonized patient. Patients with open wounds, immunocompromised patients (due to, e.g., HIV/AIDS, cancer, transplant procedure, severe asthma), young children (e.g., human infant and human toddler), and the elderly (e.g., elderly human) are at high risk of developing an MRSA infection. Higher risk rates for MRSA infection are also observed in injection drug users, persons with diabetes, patients with dermatologic conditions, patients with invasive devices (e.g., intravascular catheters), and health care workers and other people who spend time in confined spaces (prison inmates, soldiers, patients in long-term healthcare facilities, such as nursing homes). *S. aureus* most commonly colonizes the anterior nares (the nostrils), although the rest of the respiratory tract, opened wounds, intravenous catheters and urinary tract are also potential sites for infection. Most of community-associated MRSA infections are localized to the skin and soft tissue. The initial symptoms of MRSA include red bumps that resemble pimples, spider bites or boils that may be accompanied by fever and rashes; the bumps may later develop into pus-filled boils. Common manifestations of community-associated MRSA are skin infections such as necrotizing fasciitis or pyomyositis, necrotizing pneumonia, infective endocarditis, bone or joint infections. Some MRSA leads to sepsis and toxic shock syndrome, which may be due to toxins carried by such strains (e.g., PVL, PSM). MRSA may cause cellulitis. Any of the above-listed or known in the art strains of MRSA, patients diagnosed with MRSA, symptoms of MRSA, patient populations at risk of MRSA and/or diseases associated with MRSA may be treated with the compositions described herein. In some embodiments, the compositions described herein prevent onset or development of one or more of the symptoms of MRSA, or reduce duration and/or severity of one or more of these symptoms (e.g., symptoms described herein).

The compositions described herein may be used as bactericidal agents to kill or damage unwanted bacteria. For example, the compositions described herein may be used to treat established bacterial infections, prophylactically for the prevention of bacterial infections, or administered topically to areas of a subject that are susceptible to infection or to areas of the body that are likely sites for bacterial growth (e.g., the gums, open wounds, bed sores, and vaginal or groin areas).

In certain embodiments, the compositions described herein reduce bacterial growth and/or bacterial survival by more than about 0.1 log, 0.2 log, 0.25 log, 0.3 log, 0.4 log, 0.5 log, 0.6 log, 0.7 log, 0.75 log, 0.8 log, 0.9 log, 1 log, 1.25 log, 1.5 log, 1.75 log, 2 log, 2.25 log, 2.5 log, 2.75 log, 3 log, 3.25 log, 3.5 log, 3.75 log, 4 log, 4.5 log, 5 log, 5.5 log, 6 log, 6.5 log, 7 log, 7.5 log, 8 log, 8.5 log, 9 log, 9.5 log, 10 log, 10.5 log, 11 log, 11.5 log, 12 log, 12.5 log, 13 log, 13.5 log, 14 log, 14.5 log, or 15 log of colony forming units (CFU)/mL. In certain embodiments, the compositions described herein reduce bacterial growth and/or bacterial survival by about 0.2 log to 15 log, 0.2 log to 10 log, 0.2 log to 5 log, 0.5 log to 15 log, 0.5 log to 10 log, 0.5 log to 5 log, 0.5 log to 3 log, 1 log to 15 log, 1 log to 12 log, 1 log to 10 log, 1 log to 7 log, 1 log to 5 log, 1 log to 3 log, 1.5 log to 5 log, 2 log to 15 log, 2 log to 10 log, 2 log to 5 log, 3 log to 15 log, 3 log to 10 log, 3 log to 5 log, 4 log to 10 log, 2 log to 8 log, 3 log to 8 log, 4 log to 8 log, 2 log to 7 log, 3 log to 7 log, 2 log to 6 log of colony forming units (CFU)/mL, and any value in between these values. In certain embodiments, the compositions described herein reduce bacterial growth and/or bacterial survival by equal to or more than $1 \times 10^{10}$, $0.5 \times 10^{11}$, $1 \times 10^{11}$, $1.5 \times 10^{11}$, $2 \times 10^{11}$, $2.5 \times 10^{11}$, $3 \times 10^{11}$, $4 \times 10^{11}$, $5 \times 10^{11}$, $7 \times 10^{11}$, $1 \times 10^{12}$, $1.5 \times 10^{12}$, $2 \times 10^{12}$, $3 \times 10^{12}$, $5 \times 10^{12}$, $7 \times 10^{12}$, $8 \times 10^{12}$, $1 \times 10^{13}$, $1.5 \times 10^{13}$, or $2 \times 10^{13}$ (CFU)/mL, or any range of values in between these values. In some embodiments, such reduction in bacterial growth and/or survival is achieved in less than about 30 minutes, 1 hour, 2 hours, 3 hours, 4 hours, 5 hours, 6 hours, 7 hours, 8 hours, 9 hours, 10 hours, 11 hours, 12 hours, 15 hours, 18 hours, 20 hours, 22 hours, 24 hours, 36 hours, 48 hours, 60 hours, 72 hours, one day, two days, three days, four days, five days, seven days, ten days, one week, two weeks, three weeks, four weeks, 1 month or 2 months after treatment of a bacterial infection with a single application/dose or multiple application/doses of a sNAG nanofiber composition.

In one embodiment, the infection to be treated with a sNAG nanofiber composition is not a viral infection, a fungal infection, a parasite infection, or an yeast infection.

A variety of diseases or disease conditions associated with bacterial infections may be treated and/or prevented with the sNAG nanofiber compositions described herein (see, e.g., Section 5.4.2, infra). In one embodiment, methods for treating an existing bacterial infection or a disease associated with a bacterial infection are contemplated.

In some embodiments, the compositions described herein may be used to treat wounds (see Section 5.4.1, infra). In specific embodiments, the compositions described herein are used to treat bacterially infected wounds. In other embodiments, the compositions described herein are used to prevent bacterial infection of wounds. In some embodiments, the compositions described herein are used to treat bacteria known to be associated with wound infections, and specifically used to treat *Staphylococcus aureus*/MRSA, *Streptococcus pyogenes, Enterococci* and/or *Pseudomonas aeruginosa* infections, and diseases associated with such infections.

In other embodiments, the compositions described herein are not used to treat wounds. In one embodiment, the compositions described herein are not used to treat chronic wounds. In another embodiment, the compositions described herein are not used to treat burn wounds. In yet another embodiment, the compositions described herein are not used to treat surgical wounds. In one embodiment, the compositions described herein are not used to treat chronic wounds, burn wounds and surgical wounds. In another embodiment, the compositions described herein are not used to treat a wound and/or a burn. In yet another embodiment, the compositions described herein are not used to treat un-infected wounds.

In some embodiments, the compositions described herein are not used to treat a bacterially infected wound. In another embodiment, the compositions described herein are not used to treat a bacterial infection associated with or caused by a wound. In some embodiments, the compositions described herein are not used to treat bacteria known to be associated with wound infections such as *Staphylococcus aureus*/ MRSA, *Streptococcus pyogenes, Enterococci* and/or *Pseudomonas aeuruginosa.*

In some embodiment, the compositions described herein may be used to treat or prevent a variety of bacterial infections and diseases caused by or associated with bacterial infections, which are not associated with a wound (see Section 5.4.2, infra).

In certain embodiments, treatment of a disease associated with a bacterial infection comprises administration of one of the compositions described herein to a subject or a population of subjects to treat the disease or to obtain a beneficial or therapeutic effect. In specific embodiments, such treatment achieves one, two, three, four, five or more of the following effects in a subject or a population of subjects: (i) reduction or amelioration of the severity of a disease or a symptom associated therewith; (ii) reduction of the duration of a disease or a symptom associated therewith; (iii) prevention of the progression of a disease or a symptom associated therewith; (iv) regression of a disease or a symptom associated therewith; (v) prevention of the development or onset of a symptom associated therewith; (vi) prevention of the recurrence of a symptom associated therewith; (vii) prevention or reduction of the spread of a disease from the subject or population of subjects to another subject or population of subjects; (viii) reduction in organ failure associated with a disease; (ix) reduction of the incidence of hospitalization; (x) reduction of the hospitalization length; (xi) an increase the survival; (xii) elimination of a disease; (xiii) enhancement or improvement of the prophylactic or therapeutic effect(s) of another therapy; (xiv) improvement in quality of life as assessed by methods well known in the art, e.g., a questionnaire; (xv) reduction of the number of symptoms of a disease; and/or (xvi) reduction in mortality. In some embodiments, treatment comprises any therapy using compositions described herein.

In some embodiments treatment of a bacterial infection comprises administration of one of the compositions described herein to a subject or a population of subjects to treat the bacterial infection or a symptom of a bacterial infection. In specific embodiments, such treatment achieves one, two, three, four, five or more of the following effects in a subject or a population of subjects: (i) the clearance of a bacterial infection; (ii) the eradication of one or more symptoms associated with a bacterial infection, (iii) the reduction of time required to clear a bacterial infection; (iv) the reduction or amelioration of the severity of a bacterial infection and/or one or more symptoms associated therewith; (v) the reduction in the duration of a bacterial infection and/or one or more symptoms associated therewith; (vi) the prevention or delay of the generation of a resistant strain or strains of bacteria or reduction of a number of resistant strains of bacteria generated; (vii) the prevention in the recurrence of one or more symptoms associated therewith; (viii) the reduction or elimination in the bacterial cell population (such as reduction in bacterial counts, e.g., in a biological sample of a patient, as measured by CFU/mL or a log reduction by one of the methods known in the art or described herein); (ix) the reduction in hospitalization of a subject; (x) the reduction in hospitalization length; (xi) the increase in the survival of a subject; (xii) the enhancement or improvement of the therapeutic effect of another therapy; (xiii) a reduction in mortality; (xiv) the reduction or elimination in the spread of the bacteria from one subject to another subject, or one organ or tissue to another organ or tissue; (xv) the prevention of an increase in the number of bacteria; (xvi) the prevention of the development or onset of one or more symptoms associated therewith; (xvii) the reduction in the number of symptoms associated with a bacterial infection; (xviii) the inhibition or reduction in production of a bacterial toxin or toxins associated with a bacterial infection; (xix) the stabilization or reduction of inflammation associated with a bacterial infection; (xx) the reduction in organ failure associated with a bacterial infection or a disease associated therewith; and/or (xxi) improvement in quality of life as assessed by methods well known in the art, e.g., a questionnaire.

In certain embodiments, administration of the compositions described herein to a subject results in one or more of the following: (i) the induction of the expression of one or more defensin proteins and/or defensin-like proteins; (ii) the induction of the expression of one or more Toll-like receptors; and/or (iii) the induction of the expression of one or more proteins that are beneficial for clearance or reduction of a bacterial infection or one or more symptoms associated therewith.

In certain embodiments, prevention of a bacterial infection comprises administration of one of the compositions described herein to a subject or a population of subjects to achieve one or more of the following effects: (i) the inhibition of the development or onset of a bacterial infection, or a symptom associated therewith; and/or (ii) the inhibition of the recurrence of a bacterial infection, or a symptom associated therewith.

In other embodiments, prevention of a bacterial infection comprises administration of one of the compositions described herein to a subject or a population of subjects to prevent a disease associated with a bacterial infection. In specific embodiments, such prevention achieves one or more of the following effects in a subject or a population of subjects: (i) the inhibition of the development or onset of a disease associated with a bacterial infection or a symptom thereof; and/or (ii) the inhibition of the recurrence of a disease associated with a bacterial infection or a symptom associated therewith.

5.4.1 Treatment or Prevention of Bacterial Infection in Wounds

In certain embodiments, the sNAG nanofiber compositions described herein may be useful for treating a wide variety of bacterially infected wounds affecting any tissue of the body or preventing infection of wounds at risk of becoming infected with bacteria.

There are two types of wounds, open and closed. Open wounds are classified according to the object that caused the wound. For example, incisions or incised wounds (including surgical wounds) are caused by a clean, sharp-edged object such as a knife, a razor or a glass splinter. Lacerations are irregular wounds caused by a blunt impact to soft tissue which lies over hard tissue (e.g., laceration of the skin covering the skull) or tearing of skin and other tissues such as caused by childbirth. Abrasions or grazes are superficial wounds in which the topmost layer of the skin (the epidermis) is scraped off. Puncture wounds are caused by an object puncturing the skin, such as a nail or needle. Penetration wounds are caused by an object such as a knife entering the body. Gunshot wounds are caused by a bullet or similar projectile driving into (e.g., entry wound) and/or through the body (e.g., exit wound). In a medical context, all stab wounds and gunshot wounds are considered open wounds. Open wounds also include burn wounds induced by thermal, chemical, or electrical injury. Closed wounds include contusions (more commonly known as a bruise, caused by blunt force trauma that damages tissue under the skin), hematoma (also called a blood tumor, caused by damage to a blood vessel that in turn causes blood to collect under the skin), and crushing injuries (caused by a great or extreme amount of force applied over a long period of time).

In certain embodiments, the compositions described herein are used to treat a bacterial infected open wound or prevent a bacterial infection in an open wound. In certain embodiments, the compositions described herein may be used to treat or prevent a bacterial infection of a gunshot wound, a puncture wound and/or a penetration wound. In certain embodiments, the compositions described herein may be used to treat or prevent a post-operative bacterial infection, a surgical site bacterial infection, a catheter-related bacterial infection or a hemodialysis-related bacterial infection. In yet another embodiment, the compositions described herein are not used to treat or prevent a bacterial infection in an open wound, a gunshot wound, a puncture wound and/or a penetration wound. In certain embodiments, the compositions described herein are not used to treat or prevent a post-operative bacterial infection, a surgical site bacterial infection, a catheter-related bacterial infection or hemodialysis-related bacterial infection.

In some embodiments, the wound is a chronic wound. Chronic wound can be any wound that fails to heal properly, including a surgical wound (e.g., a skin graft donor site), a cutaneous ulcer (e.g., a diabetic ulcer, a venous stasis ulcer, a leg ulcer, an arterial insufficiency ulcer, or a pressure ulcer), or a burn wound. In one embodiment, the compositions described herein are used to treat or prevent chronic wound infections (e.g. an infection associated with a diabetic ulcer, a venous stasis ulcer, a leg ulcer, an arterial insufficiency ulcer, a pressure ulcer, a surgical wound, or a burn). In yet another embodiment, the compositions described herein are not used to treat or prevent chronic wound bacterial infections (e.g. not used to prevent a bacterial infection associated with a diabetic ulcer, a venous stasis ulcer, a leg ulcer, an arterial insufficiency ulcer, a pressure ulcer, a surgical wound, or a burn).

In certain embodiments, the compositions described herein are used to treat or prevent nosocomial bacterial infections. Of the nosocomial bacterial infections, surgical wound bacterial infections predominate; with statistics showing up to 8% of all surgical patients. The direct cost of these types of infections is approximately 4.5 billion dollars per year. Many of hospital-contracted bacteria developed resistance against antibiotics, and thus non-antibiotic-based treatments are desired. Use of the sNAG compositions described herein in a hospital setting could defray much of the cost and markedly reduce the production of antibiotic resistant species. In yet another embodiment, the compositions described herein are not used to treat or prevent nosocomial bacterial infections, such as surgical bacterial infections.

In one embodiment, the compositions described herein may be used to treat or prevent bacterial infections in bleeding wounds (e.g., bleeding surface wounds). In one embodiment, the compositions described herein may be used to treat a gunshot wound, a puncture wound, a penetration wound or a surgical wound in order to treat or prevent bacterial infection in such wound. In yet another embodiment, the compositions described herein are not used to treat or prevent bacterial infections in bleeding wounds (e.g., bleeding surface wounds).

The compositions described herein may be useful for treating or preventing a bacterial infection in cutaneous wounds, such as wounds affecting the epidermal and dermal layers of the skin, as well as injuries to the cornea and epithelia-lined organs, in order to treat or prevent a bacterial infection in such wounds. The wounds may be caused by a wide variety of physical trauma, including cuts, abrasions, burns, chemical exposure, surgical procedures (e.g., surgical incisions, skin grafting). In one embodiment, the compositions described herein may be used for treating corneal and sclera wounds, including wounds which affect the epithelial layer, stromal layer and endothelial layers of the eye in order to treat or prevent a bacterial infection in such wounds. In yet another embodiment, the compositions described herein are not used to treat or prevent bacterial infections in cutaneous wounds.

In some embodiments, the compositions described herein may be used to treat a wound in a patient diagnosed with a bacterial infection. In certain embodiments, where the compositions described herein are used to treat a bacterial infected wound, a wound is determined to be bacterially infected by a test or an assay for the presence of a bacterial antigen. In one embodiment, a wound culture is performed to detect a bacterial infection in the wound of a patient. In yet other embodiments, a wound is determined to be infected due to the presence of one or more symptoms of bacterial infection.

In other embodiments, the compositions described herein may be used to treat a wound in a patient when a patient displays one or more of the symptoms of bacterial infection such as: a wound is slow to heal; heat, redness and/or swelling at the site of the wound; tenderness at the site of the wound; drainage of fluid or pus at the site of the wound; and/or fever. Symptoms of wound bacterial infection include but are not limited to localized erythema, localized pain, localized heat, cellulitis, oedema, abscess, discharge which may be viscous, discolored and purulent, delayed of wound healing, discoloration of tissues both within and/or at the wound margins, friable, bleeding granulation tissue, abnormal smell coming from the wound site, unexpected pain and/or tenderness at the site of dressing change, lymphangitis (i.e., a red line originating from the wound and leading to swollen tender lymph glands draining the affected area), and wound breakdown associated with wound pocketing/bridging at base of wound (i.e., a wound develops strips of granulation tissue in the base as opposed to a uniform spread of granulation tissue across the whole of the wound bed). In some embodiments, the compositions described herein prevent the onset or development of one or more of the above-listed symptoms, or reduce duration and/or severity of one or more of these symptoms.

In one embodiment, the compositions described herein may be used for wound healing and treatment of a wound bacterial infection, or for wound healing and prevention of a wound bacterial infection. In one embodiment, the compositions described herein are used to enhance wound healing while concurrently treating or preventing a wound bacterial infection. Effects of the sNAG nanofiber compositions on wound healing and some of the uses of the sNAG nanofibers in wound healing applications have been described in U.S. Patent Pub. No. 2009/0117175, which is incorporated by reference herein in its entirety (see, e.g., Example 2).

5.4.2 Treatment or Prevention of Other Bacterial Infections

In certain embodiments, the sNAG nanofiber compositions described herein may be used to treat and/or prevent bacterial infections of the skin, gastrointestinal tract, respiratory tract, urinary tract, reproductive tract, blood, throat, ears, eye, sinus or any other organ or tissue of the body. In another embodiment, the sNAG nanofiber compositions described herein may be used to treat and/or prevent skin conditions, gastrointestinal conditions, respiratory conditions and/or conditions of any other organ or tissue associated with a bacterial infection. In some embodiments, the sNAG nanofiber compositions described herein are applied topically on the skin, mouth, ear, eye, anus or groin areas of a patient to treat or prevent a bacterial infection. In some embodiments, the compositions described herein are used to treat and/or prevent a bacterial infection of an organ or tissue of the body that is not at the site of a wound, and/or is not associated with or caused by a wound.

In certain embodiments, the sNAG nanofiber compositions described herein are used to treat an existing bacterial infection. For example, such compositions may be used to treat a subject diagnosed with a bacterial infection by a test or an assay, such as one of the tests described herein or known in the art. Alternatively, such compositions may be used to treat a subject displaying one or more symptoms of a bacterial infection or a disease associated with a bacterial infection, such as one or more symptoms of a bacterial infection known to a skilled artisan (e.g., determined by a treating doctor/physician to be a symptom of a bacterial infection) and/or described herein.

In certain embodiments, the compositions described herein are used to treat a condition associated with an imbalance in bacterial microbiota, or a condition associated with an abnormal or altered bacterial microbiota. For example, such compositions may be used to treat a skin condition in a patient whose skin bacterial microbiota differs from that in control subjects (e.g., subjects with no symptoms of the skin condition). In other examples, such compositions may be used to treat an intestinal condition (or a condition of any other tissue or organ) in a patient whose intestinal bacterial microbiota (or microbiota of the other tissue or organ) differs from that in control subjects (e.g., subjects with no symptoms of the intestinal condition).

In other embodiments, the compositions described herein may be used to treat any disease known to be associated with or exacerbated by a bacterial infection (e.g., acne). In one embodiment, the compositions described herein may be used to treat a cystic fibrosis patient infected by *P. aeruginosa*.

In some embodiments, the compositions described herein are effective against toxins secreted or excreted by bacteria. In one embodiment, the compositions described herein may be used to inhibit/reduce a bacterial toxin (and/or a condition or symptom caused by a bacterial toxin), for example toxins produced by *Bacillus anthracis, Clostridium difficile, Corynebacterium diphtheria, Pseudomonas aeruginosa*; endotoxins, and/or the cytolysins. Some defensins are able to inhibit bacterial toxins, including those produced by *Bacillus anthracis, Clostridium difficile, Corynebacterium diphtheria, Pseudomonas aeruginosa*, and the cytolysins (endotoxins produced by Gram-positive bacteria that lyse red blood cells). Given these functions of defensins, activation of pathways resulting in defensin expression and secretion may allow for the antibiotic-independent clearance of bacterial infection, and thus avoid the generation of bacterial resistance.

In certain embodiments, the compositions described herein may be used to treat and/or prevent one or more bacterial infections of the skin, or diseases of the skin associated with a bacterial infection. In some embodiments, the compositions described herein are used to treat localized skin infections and/or diffuse skin infections. In some embodiments, the compositions described herein are used to treat or prevent skin infections or diseases of the skin associated with bacterial infections affecting the epidermis, dermis, and/or subcutaneous (hypodermis) tissues of the skin. In some of these embodiments, the affected layers of the skin include one or more layers of the epidermis (i.e., stratum basale, stratum spinosum, stratum granulosum, stratum licidum, and stratum corneum), one or more types of tissues of the dermis (i.e., collagen, elastic tissue, and reticular fibers), one or more layers of the dermis (i.e., the upper, papillary layer and the lower reticular layer); and/or one or more types of tissue of the hypodermis (i.e., fat, elastin and connective tissue). In an embodiment, the compositions described herein are used to treat or prevent bacterial infections on the skin surface. In another embodiment, the compositions described herein are used to treat or prevent a *Staphylococcus* ("Staph") infection of the skin and/or a *Streptococcus* ("Strep") infection of the skin. In yet another embodiment, the compositions described herein are used to treat *Staphylococcus albus* and/or *Staphylococcus aureus* infection of the skin. In some embodiments, the compositions described herein are used to treat or prevent cellulitis, impetigo, folliculitis, erythrasma, carbuncles, furuncles, abscesses, erysipelas, and/or a cutaneous anthrax. In another embodiment, the compositions described herein are used to treat or prevent cellulitis. Cellulitis affects the deeper dermis and subcutaneous tissues, and usually affects the face, arms, and legs, and almost always occurs due to a break in the skin that leads to a bacterial infection. The symptoms of cellulitis include one or more of: swelling of the skin around the break in the skin, pain, tenderness, outward signs of blistering, red lines between the lymph nodes, fever, and chills. In another embodiment, the composition described herein are used to treat or prevent a bacterial infection of the skin at the hair follicles (e.g., folliculitis). The symptoms of folliculitis include swelling, pustules surrounding the hair, hard nodules, and pain. In another embodiment, the compositions described herein may be used to treat or prevent acne. Appearance of acne is frequently a symptom of a bacterial infection. In one embodiment, the compositions described herein are used to treat or prevent dermatitis associated with or caused by a bacterial infection. In some embodiments, the compositions described herein prevent the onset or development of one or more of the above-listed symptoms, or reduce duration and/or severity of one or more of these symptoms.

In certain embodiments, the compositions described herein may be used to treat and/or prevent one or more intestinal/digestive bacterial infections or gastrointestinal diseases associated with bacterial infections. The common forms of intestinal bacterial infection include *salmonella, shigella, E. coli, Clostridium, Staphylococcus, Listeria*, and *Yersinia*. These bacteria cause diarrhea and inflammation of the stomach and intestines, also known as gastroeneteritus. Symptoms of an intestinal bacterial infection include but are not limited to abdominal cramps and pain, bloody feces, loss of appetite, nausea sometimes accompanied by vomiting, fever, and diarrhea. In some embodiments, the compositions described herein are used to treat a patient displaying one or more symptoms of food poisoning, which is often associated with a bacterial infection.

In certain embodiments, the compositions described herein may be used to treat a disease associated with a Staph infection (e.g., a *Staphylococcus aureus* infection). In some of these embodiments, the disease is a Staph infection of the skin, nose, mouth, and/or genital area. In some embodiments, the disease is pneumonia, meningitis, endocarditis, toxic shock syndrome, and/or septicemia. In an embodiment, the compositions described herein may be used to treat Staph bacteria resistant to one or more antibiotics, for example, methicillin resistant Staph *aureus* ("MRSA"). In certain embodiments, the compositions described herein are administered to a subject diagnosed with a Staph infection, or to a subject displaying one or more symptoms of a Staph infection (e.g., presence of one or more of: small red bumps, crusty red bumps, pus filled bumps or abscess, boils, styes in the eyes, blisters and/or red scabby skin, such as red scabby skin around the nose and mouth, or symptom/s of a Toxic Shock Syndrome). In some embodiments, the compositions described herein prevent the onset or development of one or more of the above-listed symptoms, or reduce duration and/or severity of one or more of these symptoms.

In certain embodiments, the compositions described herein may be used to treat or prevent a cold associated with a bacterial infection. For example, the compositions described herein may be used to treat or prevent a cold that persists despite the use of standard pain relief medications. In one embodiment, the compositions described herein are used to treat or prevent a bacterial infection of sinus, ear or throat. The symptoms of such bacterial infections include localized pain and swelling. Bacterial infection in the sinus may lead to nasal discharge and acute pain in parts of the face or forehead. In one embodiment, the compositions described herein are used to treat strep throat (*Streptococcus pyogenes*). In some embodiments, the compositions described herein prevent the onset or development of one or more of the above-listed symptoms, or reduce duration and/or severity of one or more of these symptoms.

In some embodiments, the compositions described herein may be used to treat or prevent a genital, urinary tract or anal bacterial infection, or a disease of urinary or reproductive tract associated with a bacterial infection. In some of these embodiments, the compositions described herein may be used to treat a sexually transmitted disease associated with a bacterial infection. Symptoms of such infections include but are not limited to painful urination, cloudy discharge, and/or pain during intercourse. In some of these embodiments, the compositions described herein are used to treat or prevent one or more of syphilis, gonorrhea, clamydia, and trichomonaisis. In one embodiment, the compositions described herein are used to treat Chlamidya. In another embodiment, the described herein are used to treat gonorrhea. Symptoms of gonorrhea include localized pelvic pain, itching and irritation, painful urination, a thick yellow or green discharge, bleeding between menstrual periods. In one embodiment, the compositions described herein are used to treat or prevent a bacterial vaginosis infection. Symptoms of bacterial vaginosis include vaginal discharge, odor, vaginal itching, and abdominal pain. In some embodiments, the compositions described herein prevent the onset or development of one or more of the above-listed symptoms, or reduce duration and/or severity of one or more of these symptoms.

In other embodiments, the compositions described herein may be used to treat or prevent a respiratory tract infection (e.g., a bacterial infection of the lungs), or a respiratory disease associated with a bacterial infection. In some embodiments, such compositions are used to treat or prevent upper respiratory tract infections. In one embodiment, such compositions are used to treat or prevent tuberculosis. Tuberculosis is caused by mucobacterium tuberculosis, and it is a highly infectious disease that is spread from person to person by sneezing or saliva. Thus, the compositions described herein may be used to treat not only subjects diagnosed with tuberculosis or displaying symptoms of tuberculosis, but also individuals in contact with such subjects (e.g, family members, caretakers or medical personnel). Symptoms of tuberculosis include coughing blood, excessive weight loss, fatigue, loss of appetite and persistent fever. In some embodiments, the compositions described herein prevent the onset or development of one or more of the above-listed symptoms, or reduce duration and/or severity of one or more of these symptoms. In one embodiment, the compositions described herein are used to treat pneumonia and/or a *Streptococcus pneumoniae* infection. In another embodiment, such compositions are used to treat bronchitis. In one embodiment, the compositions described herein are used to treat *Moraxella catarrhalis, Streptococcus pneumonia* and/or *Haemophilus influenza*.

In some embodiments, the compositions described herein are used to treat or prevent bacterial infections of a mucosal surface (e.g., oral mucosa), or a disease/condition of mucosal surface associated with a bacterial infection. In one embodiment, the compositions described herein are used to treat or prevent bacterial infections of the oral cavity. For example, such compositions may be used to treat or prevent conditions associated with bacterial infections in the mouth such as gingivitis, caries, and/or tooth decay. In one embodiment, the compositions described herein may be used in oral hygiene products.

In one embodiment, the compositions described herein are used to treat a bacterial infection of the ear, such as middle ear infection, or a disease associated with such infection. In one embodiment, a composition described herein is used to treat otitis media caused by a bacterial infection.

In some embodiments, the compositions described herein are used to treat or prevent bacterial infections of implanted prosthesis, such as hearts valves and catheters. In some embodiments, the compositions described herein are used to treat animal bites, for example cat or dog bite, in order to prevent a bacterial infection.

The compositions described herein may be used to treat or prevent a variety of diseases associated with a bacterial infection including but not limited to leprosy (Hansen's disease), cholera, anthrax (e.g., cutaneous antrhax, pulmonary anthrax, gastrointestinal anthrax), pertussis, granuloma inguinale, bacterial vaginosis, gonorrhea, ophthalmia neonatorum, septic arthritis, syphilis, congenital syphilis, whooping cough, mycobacterium avium complex, meliodosis, leptospirosis, tetanus, scarlet fever, strep infections, invasive group A Streptococcal disease, Streptococcal Toxic shock syndrome, meningococcal disease, bacterimia, strep throat, Typhoid fever type salmonellosis, dysentery, colitis, salmonellosis with gastroenteritis and enterocolitis, bacillary dysentery, amebic dysentery, shigellosis, diphtheria, cutaneous diphtheria, respiratory diphtheria, Legionnaires' disease, tuberculosis, latent tuberculosis, hemophilus influenzae B, typhoid fever, vibrio parahaemolyticus, vibrio vulnificus, vibrio, yersiniosis, Whipple's disease, acute appendicitis, meningitis, encephalitis, impetigo, cellulitis, carbuncle, boil, acne, sepsis, septicemia, pneumonia, mycoplasma pneumonia, meningococcal disease, meningitis, Waterhouse-Friderichsen syndrome, ptomaine food poisoning, Staph food poisoning, Toxic shock syndrome, necrotizing pneumonia, septicemia, acute infective endocarditis, an infection of sweat glands (e.g., Hidradenitis suppurativa), a bacterial disease transmitted by a tick (e.g., Rocky Mountain Spotted Fever, Lyme disease), botulism, plague (e.g., bubonic plague, pneumonic plague), tularemia, brucellosis, acute enteritis, nongonococcal urethritis, lymphogranuloma venerium, trachoma, inclusion conjunctivitis of the newborn, psittacosis, pseudomembranous colitis, gas gangrene, acute food poisoning, diarrhea, traveller's diarrhea, diarrhea in infants, hemorrhagic colitis, hemolytic-uremic syndrome, bronchitis, listeriosis, anaerobic cellulitis, peptic ulcer, Pontiac fever, cystitis, endometritis, otitis media, sinusitis, streptococcal pharyngitis, rheumatic fever, erysipelas, puerperal fever, necrotizing fasciitis, nosocomial infections, pseudomonas infection, and/or cat scratch disease.

5.5 Patient Populations

In certain embodiments, a sNAG nanofiber composition described herein may be administered to a naïve subject, i.e., a subject that does not have a bacterial infection. In one embodiment, a composition described herein is administered to a naïve subject that is at risk of acquiring a bacterial infection.

In one embodiment, a sNAG nanofiber composition described herein may be administered to a patient who has been diagnosed with a bacterial infection. In another embodiment, a composition described herein may be administered to a patient who displays one or more symptoms of a bacterial infection.

In certain embodiments, the compositions described herein are administered to patients diagnosed with a bacterial infection. In certain embodiments, a patient is diagnosed with a bacterial infection prior to administration of a composition described herein. For example, the compositions described herein may be administered to a patient when a bacterial antigen is detected in a biological sample taken from the patient. In one embodiment, a biological sample is obtained from the site or area to be treated by the compositions described herein or an area to which the compositions described herein are to be administered. In one embodiment, a swab is used to collect cells or pus from the site of the suspected infection to detect a bacterial infection. In another embodiment, a fluid is aspirated from the suspected site of an infection (e.g., a wound) to detect a bacterial infection. In yet another embodiment, a tissue biopsy is performed to detect a bacterial infection. In an embodiment where the suspected site of an infection is a wound, a wound culture may be performed to detect a bacterial infection. In another embodiment, the biological sample is obtained from blood, urine, sputum or feces of the patient. In some embodiments, a blood or a urine test may be performed to detect a bacterial infection (e.g., when a bacterial infection is suspected to have spread into the blood or other tissues/organs). In some embodiments, the collected sample (e.g., cells, tissues or fluid) is tested using DNA detection methods such as PCR for presence of one or more types of bacteria. In other embodiments, immunofluorescence analysis, serology, culture (e.g., blood agar culture), or any other test known and/or practiced in the art may be used for laboratory diagnosis of bacterial infection.

In other specific embodiments, the compositions described herein may be administered to a patient diagnosed with or displaying one or more symptoms of a disease associated with a bacterial infection. In certain embodiments, a patient is diagnosed with a disease associated with a bacterial infection or displays one or more symptoms of a disease associated with a bacterial infection prior to administration of a composition described herein. A disease associated with a bacterial infection may be diagnosed by any method known to a skilled artisan, including evaluation of the patient's symptoms and/or detection of a bacterial antigen in a biological sample of the patient (e.g., as described above). In one example, the compositions described herein may be administered to a patient diagnosed with a disease associated with a bacterial infection by a treating physician or another medical professional. In another example, a patient may use the compositions described herein upon detection of one or more symptoms of a disease associated with a bacterial infection.

In certain embodiments, a composition described herein is administered to a patient who has been diagnosed with an infection, e.g., the bacterial infection by *Bacillus anthracis, Bordetella pertussis, Borrelia burgdorferi, Brucella abortus, Brucella canis, Brucella melitensis, Brucella suis, Campylobacter jejuni, Chlamydia psittaci, Chlamydia pneumonia, Chlamydia trachomatis, Clamidophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira pneumophila, Leptospira interrogans, Listeria monocytogenes, Moraxella catarrhalis, Mycobacterium leprae, Mycobacterium tuberculosis, Mycoplasma pneumoniae, Neisseria gonorrhoeae, Neisseria meningitides, Pseudomonas aeruginosa, Proteus mirabilis, Pneumocystis jiroveci, Rickettsia*

*rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Vibria cholerae, Yersinia pestis* and/or any other bacterial infection described herein or known in the art. In one embodiment, a composition described herein is administered to a patient who has been diagnosed with the bacterial infection by MRSA or *Pseudomonas aeruginosa*.

In certain embodiments, a composition described herein is administered to a patient who has been diagnosed with a disease associated with bacterial infection, e.g., leprosy (Hansen's disease), cholera, anthrax (e.g., cutaneous antrhax, pulmonary anthrax, gastrointestinal anthrax), pertussis, granuloma inguinale, bacterial vaginosis, gonorrhea, ophthalmia neonatorum, septic arthritis, syphilis, congenital syphilis, whooping cough, mycobacterium avium complex, meliodosis, leptospirosis, tetanus, scarlet fever, strep infections, invasive group A Streptococcal disease, Streptococcal Toxic shock syndrome, meningococcal disease, bacterimia, strep throat, Typhoid fever type salmonellosis, dysentery, colitis, salmonellosis with gastroenteritis and enterocolitis, bacillary dysentery, amebic dysentery, shigellosis, diphtheria, cutaneous diphtheria, respiratory diphtheria, Legionnaires' disease, tuberculosis, latent tuberculosis, hemophilus influenzae B, typhoid fever, vibrio parahaemolyticus, vibrio vulnificus, vibrio, yersiniosis, Whipple's disease, acute appendicitis, meningitis, encephalitis, impetigo, cellulitis, carbuncle, boil, acne, sepsis, septicemia, pneumonia, mycoplasma pneumonia, meningococcal disease, meningitis, Waterhouse-Friderichsen syndrome, ptomaine food poisoning, Staph food poisoning, Toxic shock syndrome, necrotizing pneumonia, septicemia, acute infective endocarditis, an infection of sweat glands (e.g., Hidradenitis suppurativa), a bacterial disease transmitted by a tick (e.g., Rocky Mountain Spotted Fever, Lyme disease), botulism, plague (e.g., bubonic plague, pneumonic plague), tularemia, brucellosis, acute enteritis, nongonococcal urethritis, lymphogranuloma venerium, trachoma, inclusion conjunctivitis of the newborn, psittacosis, pseudomembranous colitis, gas gangrene, acute food poisoning, diarrhea, traveller's diarrhea, diarrhea in infants, hemorrhagic colitis, hemolytic-uremic syndrome, bronchitis, listeriosis, anaerobic cellulitis, peptic ulcer, Pontiac fever, cystitis, endometritis, otitis media, sinusitis, streptococcal pharyngitis, rheumatic fever, erysipelas, puerperal fever, necrotizing fasciitis, nosocomial infections, pseudomonas infection, and/or cat scratch disease.

In some embodiments, a composition described herein is administered to a patient with a bacterial infection before symptoms of the infection manifest or before symptoms of the infection become severe (e.g., before the patient requires treatment or hospitalization). In some embodiments, a composition described herein is administered to a patient with a disease after symptoms of the disease manifest or after symptoms of the disease become severe (e.g., after the patient requires treatment or hospitalization).

In some embodiments, a subject to be administered a composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human. In some embodiments, the animal is a pet or a farm animal.

In certain embodiments, a subject to be administered a composition described herein is a human adult. In certain embodiments, a subject to be administered a composition described herein is a human adult more than 50 years old. In certain embodiments, a subject to be administered a composition described herein is an elderly human subject.

In certain embodiments, a subject to be administered a composition described herein is a premature human infant. In certain embodiments, a subject to be administered a composition described herein is a human toddler. In certain embodiments, a subject to be administered a composition described herein is a human child. In certain embodiments, a subject to be administered a composition described herein is a human infant. In certain embodiments, a subject to whom a composition described herein is administered is not an infant of less than 6 months old. In a specific embodiment, a subject to be administered described herein is 2 years old or younger.

In yet other embodiments, a composition described herein may be administered to a patient who is at risk (e.g., at high risk) of developing a bacterial infection. Patients that are at high risk of developing a bacterial infection include but are not limited to the elderly (e.g., human elderly) and immunocompromised. In some embodiments, a composition described herein is administered to a patient at risk of developing a bacterial infection, such as but not limited to an immunosuppressed patient, (e.g., as a result of cancer treatment or a transplantation procedure), a human child, a premature human infant, an elderly human, a person with diabetes, a person diagnosed with cancer, a patient who has been treated with a course of traditional antibiotics, a patient who has undergone a surgery, and or a patient with a wound. In some embodiments, the compositions described herein may be administered prophylactically to patients who are at risk for developing a bacterial infection, e.g., those with compromised immune systems due to, for example, age, malnourishment, disease, chemotherapy, those who have been treated with a course of traditional antibiotics, or those who have a wound (e.g., an open wound). In other embodiments, a patient at risk of developing a bacterial infection is an HIV/AIDS patient, a cancer patient, a patient who has undergone a transplant procedure, a patient with asthma (e.g., severe asthma), a drug user, a patient with a dermatologic conditions, a patients with an invasive device (e.g., an intravascular catheter), a health care workers or a patient who spends time in a confined facility (e.g., a prison inmate, a soldier, a patient in a long-term healthcare facility such as a nursing home, etc.). A patient to be administered a composition described herein may also be a patient with a chronic obstructive pulmonary disorder (COPD), emphysema, rhinitis, bronchitis, larynghitis, tonsillitis, and/or cystic fibrosis.

In certain embodiments, a composition described herein is administered to a patient who has not been diagnosed with a viral infection (e.g., HIV/AIDS), a fungal infection, or an yeast infection. In certain embodiments, a composition described herein is administered to a patient who does not belong to one or more of the following patient groups: an immunocompromised patient, a cancer patient, an HIV/AIDS patient, a patient with asthma, a patient who has undergone a transplant procedure, a patient who has undergone a surgery, and or a patient with a wound. In one embodiment, the patient to be administered a composition described herein does not have a wound (e.g., a chronic wound, or an open wound due, e.g., to a surgery or battlefield trauma).

In certain embodiments, a subject to be administered a composition described herein is a subject with no or low level of expression of one or more defensin peptides or a mutation/deletion in a gene or genes encoding one or more defensin peptides. In some embodiments, a subject to be administered a composition described herein is a subject with no or low or altered level of expression of one or more α-defensins (e.g., DEFA1, DEFAIB, DEFA3, DEFA4, DEFA5, DEFA6), one or more β-defensins (e.g., DEFB1, DEFB2, DEFB4, DEFB103A, DEFB104A, DEFB105B, DEFB107B, DEFB108B, DEFB110, DEFB112, DEFB114, DEFB118, DEFB119, DEFB123, DEFB124, DEFB125, DEFB126, DEFB127, DEFB128, DEFB129, DEFB131, DEFB136), and/or one or more θ-defensins (e.g., DEFT1P). In some embodiment, a subject to be administered a composition described herein is a subject with no or low or altered level of expression of one or more of DEFA1, DEFA3, DEFA4, DEFA5, DEFB1, DEFB3, DEFB103A, DEFB104A, DEFB108B, DEFB112, DEFB114, DEFB118, DEFB119, DEFB123, DEFB124, DEFB125, DEFB126, DEFB128, DEFB129 and DEFB131. In certain embodiments, a subject to be administered a composition described herein is a subject with no or low or altered level of expression of one or more Toll receptors (e.g., TLR1, TLR2, TLR3, TLR4, TLR5, TLR6, TLR7, TLR8, TLR9, TLR10, TLR11, and/or TLR12). In yet other embodiments, a subject to be administered a composition described herein is a subject with no or low or altered level of expression of one or more of IL-1, CEACAM3, SPAG11, SIGIRR (IL1-like receptor), IRAK1, IRAK2, IRAK4, TBK1, TRAF6 and IKKi. In some embodiments, a subject to be administered a composition described herein is a subject with no or low or altered level of expression of one or more of IRAK2, SIGIRR, TLR1, TLR2, TLR4, TLR7, TLR8, TLR10 and TRAF6. A low level of expression of a gene is a level that is lower (e.g., more than 1.25 fold, 1.5 fold, 2 fold, 2.5 fold, 3 fold, 3.5 fold, 4 fold, 4.5 fold, 5 fold, 6 fold, 7 fold, 8 fold, 9 fold, 10 fold lower) than the normal level of expression, wherein the normal level of expression is the level of expression is considered normal in the species to which the subject belongs by a skilled artisan and/or the level of expression in the majority of the subjects of the same species. An altered level of expression of a gene is a level that differs (e.g., by more than 20%, 25%, 30%, 50%, 75%, 100%, 150%, 200%, 250%, 300%) from the normal level of expression, wherein the normal level of expression is the level of expression is considered normal in the species to which the subject belongs by a skilled artisan and/or the level of expression in the majority of the subjects of the same species. Wherein the "normal" expression of one or more defensin genes is: (i) the average expression level known to be found in subjects not displaying symptoms or not diagnosed with the disease or infection to be treated; (ii) the average expression level detected in three, five, ten, twenty, twenty-five, fifty or more subjects not displaying symptoms or not diagnosed with the disease or infection to be treated; and/or (iii) the level of expression detected in a patient to be administered a composition described herein before the onset of the disease or infection.

5.6 Modes of Administration of sNAG Nanofiber Compositions

In certain embodiments, methods are described herein for treating or preventing a bacterial infection or a disease associated with a bacterial infection, wherein a composition comprising the sNAG nanofibers is topically administered to a patient in need of such treatment. In some embodiments, a sNAG nanofiber composition is applied topically to tissue or organ which has an increased risk of a bacterial infection or disease.

In some embodiments, an effective amount of the sNAG nanofibers and/or a sNAG nanofiber composition is administered to a subject.

In some embodiments, a composition comprising the sNAG nanofibers is administered topically to the site of the bacterial infection in a patient or to the site affected by a disease associated with bacterial infection. In yet other embodiments, a composition comprising the sNAG nanofibers is administered topically to the site and around the site of the bacterial infection in a patient or to the site affected by a disease associated with bacterial infection. In yet other embodiments, a composition comprising sNAG nanofibers is applied in proximity to the site of the bacterial infection in a patient or in proximity to the site affected by a disease associated with bacterial infection. In yet another embodiment, a composition comprising the sNAG nanofibers is administered topically to the site at high risk of a bacterial infection.

The sNAG nanofiber compositions described herein may be administered by any of the many suitable means of topical administration which are well known to those skilled in the art, including but not limited to topically to the skin, topically to any other surface of the body (e.g., mucosal surface), by inhalation, intranasally, vaginally, rectally, buccally, or sublingually. The mode of topical administration may vary depending upon the disease to be treated or prevented. The sNAG nanofiber compositions can be formulated for the various types of topical administration.

In one embodiment, a composition comprising sNAG nanofibers is applied to the skin of a patient. For example, such composition may be applied topically to the skin of a patient for treating and/or preventing a bacterial infection of the skin or a disease of the skin that is associated with a bacterial infection.

In another embodiment, a composition described herein may be applied topically to a mucosal surface of a patient. For example, such composition may be applied topically to oral mucosa for treating and/or preventing a bacterial infection of the mouth or gums or a disease of the mouth or gums that is associated with a bacterial infection.

In some embodiments, a composition comprising sNAG nanofibers is applied to the wound in a patient. For example, such composition may be applied topically directly to site of the wound or in proximity to the site of the wound of a patient for treating and/or preventing a bacterial infection of the wound or a disease associated with a bacterial infection of the wound. In one such embodiment, the wound is a bacterially infected wounds, for example, as diagnosed by one of the methods described herein. The wound may be any one of the types of wounds described herein. In yet other embodiments, a composition comprising sNAG nanofibers is not applied to a wound in a patient, or is not applied to a bacterially infected wound in a patient.

In some embodiments, a composition described herein may be applied topically to a genital, urinal or anal surface/area of a patient. For example, such composition may be applied topically to genital, urinal or anal surface/area for treating and/or preventing genital, urinal or anal bacterial infections or a disease of such tissues that is associated with a bacterial infection.

The above-listed methods for topical administration may include administration of the sNAG nanofiber in the form of a cream, an ointment, a gel, a liquid solution, a membrane, a film, a spray, a paste, a powder or any other formulation described herein or known in the art. The sNAG nanofiber may also be applied in a dressing or a bandage, for example to treat localized infections/conditions on the skin of a patient.

In some embodiments, a composition described herein may be applied as a spray into the oral cavity and/or respiratory system of a patient. For example, such composition may be applied as a spray for treating and/or preventing bacterial infection of the mouth, nose, gums, throat or lungs or a disease/condition of the mouth, nose, gums, throat or lungs that is associated with a bacterial infection. In one such embodiment, the composition may be formulated to be administered as an inhaler.

In some embodiments, a composition described herein may be applied as a suppository in the rectum, vagina or urethra of a patient. For example, such composition may be applied as a suppository for treating and/or preventing bacterial infection of the digestive tract, urinary tract or reproductive tract or a disease of such tissues that is associated with a bacterial infection.

In another embodiment, a composition described herein may be applied at the site of a surgical procedure. For example, such composition may be sprayed, applied as a cream, ointment, gel, membrane, or powder, or coated on the surface of the tissue or organ to be subjected to a surgical procedure or that has been subjected to the surgical procedure. In one embodiment, a composition described herein is applied at the site of the surgical incision, at the site of the excised tissue, or at the site of surgical stitches or sutures. Such administration of a composition described herein may prevent a post-surgical infection. For example, a composition described herein may be used during or after a surgical procedure which is known to pose high risk of a bacterial infection. Surgical procedures that are known to pose high risk of a bacterial infection include bowel resection, gastrointestinal surgical procedures, kidney surgery, etc. A composition described herein may be applied at the site of any of the above-listed or other surgical procedures.

In yet other embodiments, a composition described herein may be coated on a device, for example an oral hygiene product, a catheter, a surgical instrument or another product, to be used in or inserted into a patient, in order to prevent a bacterial infection in a patient.

In some embodiments, methods contemplated herein include a step that includes detection/diagnosis of a bacterial infection in a patient. In some embodiments, detection/diagnosis involves a test or assay for one or more bacteria or bacterial antigens in a biological sample of the patient. In other embodiments, diagnosis involves assessing whether the patient has one or more symptoms of a bacterial infection or a disease associated with a bacterial infection.

The compositions described herein may exhibit sustained release properties and/or may be administered in a formulation resulting in a sustained release of such compositions. In some embodiments, the sNAG nanofibers biodegrade over time as described in Section 5.1, supra, and these properties of sNAG nanofibers may lead to or contribute to sustained release of the compositions described herein. In yet other embodiments, the compositions described herein are formulated to display sustained release capabilities using any methods known in the art. The compositions described herein may exhibit sustained release over a time period equal to or more than about 6 hours, 12 hours, 18 hours, 24 hours (1 day), 2 days, 3 days, 5 days, 7 days (1 week), 10 days, 14 days (2 weeks), 3 weeks or 4 weeks after administration of the composition to the patient.

Contemplated treatment regimes include a single dose or a single application of a sNAG nanofiber composition (e.g., of a cream, a membrane or a dressing), or a regiment of multiple doses or multiple applications of a sNAG nanofiber composition. A dose or an application may be administered hourly, daily, weekly or monthly. For example, a dose of a sNAG nanofiber composition may be administered once a day, twice a day, three times a day, four times a day, five times a day, every 3 hours, every 6 hours, every 12 hours, every 24 hours, every 48 hours, every 72 hours, once a week, 2 times a week, 3 times a week, every other day, once in 2 weeks, once in 3 weeks, once in 4 weeks, or once a month.

A sNAG nanofiber composition may be administered for a duration equal to or greater than 1 week, 2 weeks, 3 weeks, 1 month, 2 months, 3 months, 4 months, 5 months, 6 months, 9 months, 1 year, 1.5 years, 2 years, 2.5 years, 3 years, 4 years, 5 years, 7 years, 10 years or more. In one such embodiment, a sNAG nanofiber composition does not cause any side effects or causes only mild side effects during the duration of the treatment. In one such embodiment, a sNAG nanofiber composition does not lose its effectiveness or does not cause generation of resistant strains of bacteria in response to the treatment. In another embodiment, a sNAG nanofiber composition does not cause irritation (e.g., moderate or severe irritation) or allergy (e.g., moderate or severe allergy).

Concentration of the sNAG nanofiber in a composition may vary. In general, an effective amount of the sNAG nanofiber is used. A effective amount may be an amount sufficient to achieve one or more of the effects described herein, for example an amount effective to reduce or eradicate a bacterial infection, or reduce or eradicate one or more symptoms of a bacterial infection. For example, a composition may comprise about 0.2 to 20 mg/cm$^2$ of the sNAG nanofibers per dose/application of the composition in a form suitable for topical delivery to a patient. In certain embodiments, a composition described herein comprises about 0.25 to 20 mg/cm$^2$, about 0.5 to 20 mg/cm$^2$, about 1 to 20 mg/cm$^2$, about 1 to 15 mg/cm$^2$, about 1 to 12 mg/cm$^2$, about 1 to 10 mg/cm$^2$, about 1 to 8 mg/cm$^2$, about 1 to 5 mg/cm$^2$, about 2 to 8 mg/cm$^2$, or about 2 to 6 mg/cm$^2$ of the sNAG nanofibers per dose/application of the composition in a form suitable for topical delivery to a patient.

5.7 Combination Therapy

The sNAG nanofiber compositions may be administered in conjunction with other therapies such as substances that boost the immune system, antibacterial agents (e.g., an antibiotic), defensin peptides, defensin-like peptides, pain relief therapy (e.g., an analgesic), fever relief therapy, and/or other agents or drugs known to be effective against or commonly used for treatment and/or prevention of bacterial infections or diseases associated with bacterial infections.

In some embodiments, a composition described herein is administered in conjunction with an additional anti-bacterial agent, for example an antibiotic. In one such embodiment, a composition described herein may be used to treat a bacterial infection or a disease associated with a bacterial infection in conjunction with a standard therapy commonly used to treat such bacterial infection or such disease. In one embodiment, a composition described herein may be administered to a patient diagnosed with or displaying symptoms of a bacterial infection or a disease associated with a bacterial infection in conjunction with a standard anti-bacterial agent (e.g., an antibiotic) known to be effective against such bacterial infection or such disease.

In certain embodiments, a composition described herein is administered in conjunction with an antibiotic of one of the following classes of antibiotics: microlides (e.g., erythromycin, azithromycin), aminoglycosides (e.g., amikacin, gentamicin, neomycin, streptomycin), cephalosporins (e.g., cefadroxil, cefaclor, cefotaxime, cefepime), fluoroquinolones (e.g., ciprofloxacin, levofloxacin), penicillins (e.g., penicillin, ampicillin, amoxicillin), tetracyclines (e.g., tetracycline, doxycycline), and carbapenems (e.g., meropenem, imipenem). In some embodiments, a composition described herein is administered in conjunction with an agent (e.g., an antibiotic) effective to treat or prevent or commonly used to treat or prevent an *S. aures* infection, MRSA infection, a *Pseudomonas* infection, or a *C. difficile* infection.

In a specific embodiment, a composition described herein is administered in conjunction with one or more of vancomycin, sulfa drug (e.g., co-trimoxazole/trimethoprim-sulfamethoxazole), tetracycline (e.g., doxycycline, minocycline), clindamycin, oxazolidinones (e.g., linezolid), daptomycin, teicoplanin, quinupristin/dalfopristin (synercid), tigecycline, allicin, bacitracin, nitrofurantoin, hydrogen peroxide, novobiocin, netilmicin, methylglyoxal, and bee defensin-1. A composition described herein may also be administered in conjunction with a dressing comprising one or more of hydrogen peroxide, tobramycin, chlorhexidine digluconate, chlorhexidine gluconate, levofloxacin, and silver. In one embodiment, a composition described herein is administered with one or more of the listed agents to treat or prevent a *S. aureus* infection, and particularly, an MRSA infection.

In some embodiments, the compositions described herein are administered before (e.g., 1 minute, 15 minutes, 30 minutes, 1 hour, 2 hours, 3 hours, 6 hours, 12 hours, 24 hours or more before, or any time period in between), simultaneously with, or after (e.g., 1 minute, 15 minutes, 30 minutes, 1 hour, 2 hours, 3 hours, 6 hours, 12 hours, 24 hours or more after, or any time period in between) administration of another therapy. For a example, such compositions maybe administered before, simultaneously with or after administration of an anti-bacterial agent (e.g., an antibiotic).

In some of these embodiments, the compositions described herein may be administered to a patient to treat or prevent a bacterial infection or a disease associated with bacterial infection after the patient has undergone a course of treatment of the bacterial infection with another antibacterial agent (e.g., an antibiotic). In some embodiments, the compositions described herein may be administered to a patient who has developed resistance to one or more antibacterial agents (e.g., an antibiotic). In one embodiment, the compositions described herein may be administered to a patient who has undergone a course of treatment with an antibiotic (e.g., an antibiotic standardly used for the treatment of such bacterial infection) and developed resistance to such antibiotic.

However, in certain embodiments, a sNAG nanofiber composition is administered alone. In one such embodiment, a sNAG nanofiber composition is not administered with any other therapies, for example, it is not administered with an immunomodulator, an antibacterial agent (e.g., an antibiotic), a defensin peptide, a defensin-like peptide, a pain relief therapy (e.g., an analgesic), or a fever relief therapy. In one embodiment, a sNAG nanofiber composition is not administered in conjunction with an antibiotic. In certain embodiments, sNAG nanofiber compositions are not administered in conjunction with an anti-viral agent, an anti-fungal agent or an anti-yeast agent.

5.8 Kits

A pharmaceutical pack or kit which comprises any of the above-described sNAG compositions is also contemplated. The pack or kit may comprise one or more containers filled with one or more ingredients comprising the compositions described herein. The composition is preferably contained within a sealed, water proof, sterile package which facilitates removal of the composition without contamination. Materials from which containers may be made include aluminum foil, plastic, or another conventional material that is easily sterilized. The kit can contain material for a single administration or multiple administrations of the composition, preferably wherein the material for each administration is provided in a separate, waterproof, sterile package.

In another embodiment, a container having dual compartments is provided. A first compartment contains any of the above-described sNAG compositions, while the second compartment contains another active agent such as another anti-bacterial agent. In the field or the clinic, the composition in the first compartment can be readily combined with the agent in the second compartment for subsequent administration to a patient.

Additionally, a kit designed for emergency or military use can also contain disposable pre-sterilized instruments, such as scissors, scalpel, clamp, tourniquet, elastic or inelastic bandages, or the like.

Optionally associated with such kit or pack can be a notice in the form prescribed by a governmental agency regulating the manufacture, use or sale of pharmaceuticals or biological products, which notice reflects approval by the agency of manufacture, use or sale for human administration. For example, a kit can comprise a notice regarding FDA approval and/or instructions for use.

The kits encompassed herein can be used in the above applications and methods.

6. EXAMPLES 6.1 Example 1: sNAG Nanofibers from a Marine Diatom Promote Wound Healing and Defensin Expression Via an Akt1/Ets1-Dependent Pathway This example demonstrates that sNAG nanofibers promote cutaneous wound healing and expression of defensins, and that the Akt1→Ets1 pathway plays a central role in the regulation of cutaneous wound healing by sNAG nanofibers.

6.1.1 Materials and Methods sNAG/Taliderm nanofibers are produced and supplied by Marine Polymer Technologies and formed into suitable patches for wound treatment. Wildtype C57 Black and Akt1 null mice were housed at the Medical University of South Carolina animal facilities. Wildtype and Akt1 null mice, ages ranging from eight to 12 weeks, were anesthetized with 50% pure oxygen and 50% isoflurane gas. Immediately before wounding, Nair Hair Removal Lotion was applied to their dorsum to remove any unwanted hair. A dorsal 4 mm circular area of skin was removed using an excision biopsy punch. Taliderm was placed onto each wound at day 0 or wounds were left untreated. At days 1, 3, 5, and 7 the wounds were photographed, measured, and excised using an 8 mm biopsy punch to ensure complete removal of the wound and surrounding skin. Wildtype and Akt1 null wounds with and without Taliderm treatment were embedded in paraffin in preparation for H&E and immunofluorescent staining.

Paraffin-embedded sections were sectioned and placed on microscope slides for staining. Slides were washed with xylenes to remove paraffin and rehydrated through a series of graded alcohols. The sections were then incubated in 0.1% Triton×100 for permeabilization. Sections were incubated in a boiling Antigen Retrieval solution. 1% Animal serum was used for blocking before incubating in the primary goat antibody, β-defensin 3 1:400 dilution. The sections were then incubated in the primary antibody overnight at 4° in a humidity chamber. An immunofluorescent secondary Donkey α-goat 488 antibody 1:200 dilution was used, followed by nuclear staining with TOPRO-3. Images were captured using confocal microscopy.

Hematoxylin and eosin staining was used to visualize basic structures such as the epidermis, dermis, muscle, and blood vessels and to determine the orientation and approximate location in the wound. H&E staining was also used to begin to identify which cell types are stimulated by Taliderm in an Akt1-independent manner.

Other materials and methods are described in figure descriptions and in the results section below, and performed in accordance with the methods known in the art.

6.1.2 Results sNAG Nanofibers Stimulate Akt 1 Activation, an Upstream Regulator of Ets1. FIG. 1A shows a Western blot analysis of phospho-Akt in response to NAG and sNAG stimulation of serum starved EC. FIG. 1B shows RT-PCR analysis of EC infected either with scrambled control or Akt1 shRNA lentiviruses and assessed for expression of Ets1 and S26 as a loading control. FIG. 1C illustrates a signal transduction pathway transducing a signal from sNAG nanofibers to Akt1, Ets1 and Defensins.

Delayed Wound Healing in Akt1 Null Animals is Partially Rescued by Taliderm (sNAG) Treatment. FIG. 2A shows representative images of wounded WT and AKT1 null mice with and without treatment of Taliderm. FIG. 2B shows H&E staining of representative mouse skin sections from day 3 wounds. H&E staining of wildtype and Akt1 wound exicisons indicate a Taliderm depdendent increase in keratinocyte proliferation and migration. The dashed lines indicate the area of keratinocyte proliferation across the wound margin. In both the wildtype and Akt1 treated wounds there is an evident increase in reepithelization across the wound margin compared to the wildytpe and Akt1 control. This indicates that Taliderm increases kertainoctye recruitment indepdent of the Akt1 pathway. Although Taliderm induces a complete reepithlization of the epidermis across the wound margin, there is still substanial lack of revascularization in the underlying tissue compared to the wildtype. This is evident by substantial hemorrhaging and infiltration of red blood cells in the Akt1 aminals.

sNAG Nanofibers Stimulate Cytokine and Defensin Expression in Primary Endothelial Cells. FIG. 3A shows immunohistochemisty of EC treated with or without sNAG using an antibody directed against α-defensin. FIG. 3B presents ELISA showing that nanofiber treatment of EC results in the secretion of α-defensins 1-3.

sNAG Nanofibers Stimulate Defensin Expression in Primary Endothelial Cells in an Akt1 Dependent Manner. FIGS. 4A and 4B show quantitative RT-PCR analyses of serum starved EC treated with or without sNAG, with or without PD98059 (MAPK inhibitor), Wortmannin (PI3K inhibitor) or infected with a scrambled control or Akt1 shRNA lentiviruses and assessed for expression of the genes indicated.

sNAG Nanofibers Stimulate β-defensin 3 Expression in Mouse Keratinocytes. FIG. 5A shows immunofluorescent staining with β-defensin 3 and Involucrin antibodies of paraffin embedded mouse cutaneous wound sections from WT and Akt1 null animals on Day 3. A cutaneous wound healing model was developed in both WT and Akt1 null mice to assess the effects of Taliderm in vivo. These findings show that β-defensin 3 expression increases in Taliderm treated animals in an Akt1-dependent manner. The ability of Taliderm to increase defensin expression in a healing wound has important implications for treating and controlling wound infection. FIG. 5B shows quantification of β-defensin 3 immunofluorescent staining using NIHImageJ software. FIG. 5C shows immunofluorescent staining of WT and Akt1 null treated and untreated keratinocytes with β-Defensin 3 and TOPRO-3. Notice the increase in green β-Defensin 3 staining in WT and Akt1 Taliderm treated wounds. The immunofluorescent labeling of wound sections illustrates that Taliderm treated wounds show an increase in β-defensin 3 expression in an Akt1 dependent manner. Although the Akt1 treated wounds show a reasonable increase in β-defensin 3, the wildtype treated wounds illustrate a more remarkable increase. This indicates that β-defensin 3 expression is not only increased by application of the nanofiber, but is at least partially dependent on the Akt1 pathway. β-defensin 3 expression seems limited to the keratinocytes indicating this expression is keratinocyte specific.

Akt1 dependent transcription factor binding sites. FIG. 6 shows schematic of Akt1 dependent transcription factor binding sites. Using Genomatix software, 500 bp upstream of the transcription start site was analyzed for conserved sites on the mRNA of DEF1, 4, and 5.

6.1.3 Conclusions

The provided data show that sNAG nanofiber stimulation of Ets1 results from the activation of Akt1 by these nanofibers. Nanofiber treatment resulted in marked increases in the expression of genes involved in cellular recruitment, such as IL-1 (a known Ets1 target), VEGF and several defensins (β3, α1, α4, and α5), small anti-microbial peptides recently shown to act as chemoattractants. Both pharmacological inhibition of the PI3K/Akt1 pathway and Akt1 knockdown using shRNAs resulted in decreased expression of these chemotactic factors. Akt1 null mice exhibited a delayed wound healing phenotype that is partially rescued by Taliderm nanofibers. Taliderm treated wounds also showed an increase in defensin expression that is Akt1 dependent.

The increase of β-defensin 3 expression and keratinocyte proliferation in Taliderm treated wounds demonstrates the beneficial use of Taliderm as an effective wound healing product. Taliderm acts to increase anti-microbial peptide expression in keratinocytes in an Akt1 dependent manner suggesting the essential role of Akt1 in the function of sNAG nanofibers. This correlates with the results from other studies in the laboratory (Buff, Muise-Helmericks, unpublished) that inhibition of the PI3K/Akt1 pathway and Akt1 knockdown using shRNAs results in decreased expression of these chemotactic factors.

Although the increased expression of β-defensin 3 is Akt1-dependent, H&E staining of 8 mm wound excisions (FIG. 2B) indicated that Taliderm acts independent of Akt1 in wound reepithelization. Even though the new keratinocytes span the entire wound margin, the underlying tissue did not demonstrate the same stimulation in vascular growth. This indicates the that absence of Akt1 is responsible for leaky blood vessels and the large amount of floating red blood cells in the dermis. This suggests that Taliderm is dependent on the Akt1 pathway for an increase in vascularization.

In summary, (i) sNAG nanofibers (Taliderm) increase wound healing in part by stimulating angiogenesis; (ii) sNAG nanofibers treatment of endothelial cells activate an Akt1/Ets1 dependent pathway leading to changes in cell motility and cytokine secretion; (iii) Taliderm treated wounds show increased expression of β-defensin 3 in an AKT1 dependent manner; (iv) treatment of Akt1 null animals with Taliderm partially rescues the phenotype, leading to markedly increased keratinocyte proliferation/migration; and (v) bioinformatics analysis indicates that ETS 1 is likely involved in the sNAG activated pathway leading to increased wound healing and cytokine secretion.

Taken together these findings suggest a central role of the Akt1→Ets1 pathway in the regulation of cutaneous wound healing by sNAG nanofibers and support the use of these nanofibers as a novel and effective method for enhancing wound healing.

6.2 Example 2: sNAG Nanofibers Increase Defensin Expression, Increase Kinetics of Wound Closure, and have an Indirect Defensin-Dependent Anti-Bacterial Effect This example demonstrates that sNAG nanofibers have a potent anti-bacterial effect against *Staphylococcus aureus* in vivo, which is indirect and defensin-dependent. This example also shows that sNAG nanofibers induce expression of defensins in vitro in keratinocytes and endothelial cells and in vivo in cutaneous wounds, in an Akt-1 dependent manner, and increase the kinetics of wound closure.

6.2.1 Materials and Methods

Tissue Culture, Pharmacological Inhibition, ELISA: Human umbilical cord vein EC (Lonza) were maintained at 37° with 5% CO2 in endothelial basal medium 2 (Lonza). Endothelial basal medium 2 (EBM2) was supplemented with EC growth medium 2 SingleQuots as described by Lonza procedures and 1% penicillin/streptomycin (Invitrogen). Serum starvation was performed at 80-90% confluency in EBM2 supplemented with 0.1% fetal calf serum (Valley Biomedical) for 24 hours followed by stimulation with highly purified pGlcNAc (50 µg/ml) nanofibers (sNAG) in sterile water (provided by Marine Polymer Technologies, Inc., Danvers, Mass., USA). The pGlcNAc diatom-derived nanofibers used in this study are short biodegradable fibers derived from a longer form (NAG), and have an average length of 4-7 µm and a polymer molecular weight of approximately 60,000 Da. For inhibition using PD098059 (50 µM) or wortmannin (100 nM), cells were pre-treated for 45 minutes prior to 3 hour stimulation with sNAG (50 µg/ml).

Statistical Analysis: Each quantitative experiment was performed at least in triplicate at least three independent times. All statistical analyses were performed using Microsoft Excell to calculate means, standard deviations and student t-test Lentiviral Infection: Mission shRNA lentiviral constructs directed against Akt1 were purchased from Sigma/Aldrich. A scrambled pLKO.1 shRNA vector was purchased from Addgene. Lentiviruses were propagated in 293T cells, maintained in DMEM supplemented as above. Lentiviral production was performed using psPAX2 and pMD2.G packaging vectors purchased from Addgene using the protocol for producing lentiviral particles from Addgene. For infection of target cells, $7.5 \times 10^5$ cells were plated on 100 mm2 plates and allowed to incubate overnight. The next day, cells were transduced using a final concentration of 1 µg/ml polybrene and either scrambled control or Akt1 shRNA lentiviruses. After transduction, endothelial cells were serum starved overnight and stimulated with sNAG (50 g/ml) for 3 hours. All infections were monitored for appropriate knockdown by RT-PCR.

RT-PCR: For semi-quantitative RT-PCR, RNA was extracted with RNAsol (Teltest, Inc.) following manufacturer's instructions. cDNA was synthesized from 2 µg total RNA with a Superscript First Strand Synthesis Kit (Invitrogen), using Oligo(dT) following the manufacturer's instructions. PCR reactions contained equal amounts of cDNA and 1.25 µM of the appropriate primer pair (Sigma—Proligo, St. Louis, Mo., USA). All primer sequences used in these analyses are as follows:

```
Akt1 F
                                  (SEQ ID NO: 1)
5' GAGGCCGTCAGCCACAGTCTG 3'

Akt1 R
                                  (SEQ ID NO: 2)
5' ATGAGCGACGTGGCTATTGTG 3'

β-Defensin3 F
                                  (SEQ ID NO: 3)
5' GTGGGGTGAAGCCTAGCAG 3'

β-Defensin 3 R
                                  (SEQ ID NO: 4)
5' TTTCTTTCTTCGGCAGCATT 3'

α-Defensin1 F
                                  (SEQ ID NO: 5)
5' CACTCCAGGCAAGAGCTGAT 3'

α-Defensin1 R
                                  (SEQ ID NO: 6)
5' TCCCTGGTAGATGCAGGTTC 3'

S26 F
                                  (SEQ ID NO: 7)
5' CTCCGGTCCGTGCCTCCAAG 3'

S26 R
                                  (SEQ ID NO: 8)
5' CAGAGAATAGCCTGTCTTCAG 3'
```

Cycling conditions were: 94° C. for 5 min; 30-35 cycles of 94° C. for 1 min, 55-65° C. (based on primer $T_m$) for 1 min, 72° C. for 1 min; 72° C. for 7 min and cooled to 4° C. Cycle number was empirically determined to be within the linear range of the assay for each primer pair used. All semi-quantitative RT-PCR was performed with the ribosomal protein subunit S26 primers as internal controls. Products were visualized on a BioRad Molecular Imaging System (Hercules, Calif., USA). Real time PCR was performed using a Brilliant CYBR green QPCR kit in combination with an Mx3000P Real-Time PCR system both purchased from Stratagene. Primers detecting the ribosomal subunit S26 were used as internal controls.

Excisional Wound Healing Model: Wild Type C57Bl/6 and Akt1−/−[43] were used in all experiments. The Akt1 null animals were created using an insertional mutagenesis strategy at the translational start site that blocks expression of the entire protein. Wounding was performed on anesthetized adult male mice between 8-12 weeks old. Two full thickness cutaneous wounds were created using a 4 mm biopsy punch (Miltex), to create two identical wounds on each flank. Mice were anesthetized using an $O_2$/Isoflurane vaporizing anesthesia machine (VetEquip, Inc.). Isoflurane was used at 4% for induction; 2% for surgery. Prior to surgery hair was removed by depilation and the area was washed and sterilized using 70% ethanol. Wounds were either treated with sNAG membrane moistened with distilled water or left untreated. On days 3 and 5 animals were euthanized and entire wounds were harvested including the surrounding skin using an 8 mm biopsy punch (Miltex). Wounds were fixed in 4% paraformaldehyde overnight at 4°, embedded in paraffin, and sectioned for analysis.

Hematoxylin and Eosin Staining (H&E): All H&E staining was performed in the Histology Core Facility at the Medical University of South Carolina, Department of Regenerative Medicine and Cell Biology. Briefly, sections were cleared in xylene, rehydrated through a series of graded alcohols, placed in Hematoxylin followed by acid alcohol. Samples were then placed in ammonia water, rinsed in ethanol and exposed to Eosin before dehydrating through graded alcohols and clearing in xylene. Sections were mounted using Cytoseal-XYL (Richard-Allan Scientific). H&E sections were visualized using an Olympus BX40 microscope (4× objective lens, 0.13) and captured using an Olympus Camera (Model DP25) and DP2-BSW acquisition software.

Bacterial Inoculation, Tissue Gram Staining, Colony Forming Unit Quantitation: Male mice between 8-12 weeks were wounded as described above. Single colonies of Staphylococcus aureus (ATCC 25923) were picked and cultured overnight at 37° and adjusted to an absorbance of $OD_{600}$=0.53. One mL of S. aureus was spun at 10,000 rpm, re-suspended in sterile PBS, and 15 μl was used to innoculate each wound. sNAG membranes were applied to the treated group thirty minutes post inoculation. Mice were euthanized on day 3 and 5 post wounding and wounds were harvested using an 8 mm biopsy punch. One wound per animal was fixed overnight in 4% paraformaldehyde at 4° C. and the other wound was cultured and plated on LB media without antibiotic for bacterial quantitation (see below). Wounds for tissue gram staining were embedded in paraffin and sectioned. Sections were cleared in xylene and rehydrated through a series of alcohol and were stained using a tissue gram stain (Sigma-Aldrich) by procedures described by the manufacturer.

For culturing, wound sections were placed in 0.5 ml bacterial media an incubated for 30 min at 37° C. while shaking. Colony forming units (CFU) were quantitated using a dilution series plated overnight at 37° C. Number of colonies per plate/per dilution were counted and CFU/ml were calculated.

To determine CFU/ml from sNAG treated bacterial cultures, S. aureus cultures in solution were treated with varying concentrations of sNAG (10 μl and 20 μl of 10.8 mg/ml sNAG) for three hours. Cultures were then plated overnight at 37° and CFU/ml were determined.

β-defensin 3 Peptide Application: Three test concentrations (1.0 μM, 2.5 μM, 5.0 μM) of biologically active human β-defensin 3 peptide (Peptide Institute, Inc.) were tested for their effect on bacterial growth in the infected wound healing model described above. Each concentration negatively affected bacterial growth so the lowest concentration was chosen for analyses. After each wound was infected with S. aureus, 10 μl of peptide was applied. After three days, wounds were harvested, embedded for sectioning and gram staining, or cultured for CFU/ml quantitation as described above.

β-defensin 3 Antibody Blockade: Wild Type male mice were wounded and infected with 15 ul of S. aureus as described above. After inoculation, one wound was treated with 0.2 ug/mL of β-defensin 3 antibody (Santa Cruz) while the other was treated with 0.2 ug/mL of normal goat IgG control antibody (Santz Cruz). sNAG membranes were applied to all mice after antibody treatment on day 0. Antibody was applied every 24 hours. Mice were euthanized on day 3 and wounds were harvested using an 8 mm biopsy punch. Wounds were fixed overnight in 4% paraformaldehyde at 4° C., embedded in paraffin, sectioned, and analyzed using tissue gram stain. CFU/ml quantitation was performed from wounds harvested on day 3 as described above.

Immunofluoresence, Microscopy: Paraffin embedded tissue sections were re-hydrated through xylene and a series of graded alcohols. Sections were treated with 0.01% Triton-X100 and subjected to antigen retrieval using antigen unmasking solution (Vector Laboratories) in a pressure cooker for 5 min and allowed to cool. Skin sections were labeled with β-defensin 3 goat polyclonal antibody (Santa Cruz), involucrin rabbit polyclonal antibody (Santa Cruz), and TO-PRO 3-iodide (Molecular Probes). Sections were incubated in primary antibody overnight at 4° and appropriate secondary immunofluorescent antibodies (Invitrogen) for 1 hour at room temperature. Control sections for each antibody were stained without primary antibody. Tissue sections were visualized using an Olympus FluroView laser scanning confocal microscope (Model IX70) and captured at ambient temperature using an Olympus camera (Model FV5-ZM) and Fluoview 5.0 acquisition software. All tissue sections were imaged using 60× oil immersion lens (Olympus Immersion Oil)

HUVECs were either serum starved or treated with sNAG for 5 hours in culture and stained with antibodies directed against α-defensin 5 (FITC), β-defensin 3 (Texas Red), or TOPRO 3 (Blue). Images were taken using immunofluorescent microscopy. Cell culture defensin expression was visualized using a Zeiss Axiovert 100M confocal microscope and was captured at ambient temperature, using water as the medium, using LSM 510 camera (Zeiss Fluor 63xW/1.2A objective).

Western Blot Analysis: Endothelial cells were serum starved prior to stimulation with sNAG (50 μl/ml) for a given time course. Cells were then lysed and subjected to Western blot analysis. The antibodies used for Western blot analysis are as follows: anti-p85 subunit of PI3K and phosphospecific Akt antibody (Cell Signaling Technologies).

6.2.2 Results 6.2.2.1. Keratinocytes and Endothelial Cells Express and Secrete Defensins when Stimulated with sNAG This example demonstrates that sNAG treatment modulates the expression of defensins, small anti-microbial peptides that are part of the innate immune response.

To investigate the affect of sNAG treatment on defensin expression in vitro, primary human umbilical vein endothelial cells in culture were used. Endothelial cells express both α-type and β-type defensins when stimulated with sNAG. As shown in FIG. 7A endothelial cells treated with sNAG show an up-regulation of β-defensin 3 and α-defensin 1 mRNA expression within 1 hour of stimulation. Similar up-regulation of α-defensin 4 and 5 by sNAG treatment was also observed (data not shown). Custom gene arrays containing over 25 different defensin genes were used to confirm the expression of the α-type defensins in primary endothelial cells and the β-type defensins in keratinocytes. sNAG stimulation of endothelial cells was shown to increase the expression specifically of α-defensins 1, 4 and 5 and β-defensin 3. Additionally, sNAG stimulation of human keratinocytes increased expression of β-defensin like genes, several of which are listed in Table 1. These findings suggest that at least three α-defensin genes and β-defensin 3 are expressed in primary endothelial cells and multiple β-defensin genes are expressed in primary keratinocytes in response to sNAG stimulation.

TABLE I

Gene array analysis reveals numerous defensin genes upregulated by sNAG

| HUVEC Gene Name | Fold Change | Keratinocyte Gene Name | Fold Change |
| --- | --- | --- | --- |
| α-defensin 1 | +1.36 | β-defensin 1 | +1.4 |
| α-defensin 4 | +2.74 | β-defensin 126 | +1.73 |
| α-defensin 5 | +2.46 | β-defensin 105B | +2.55 |
| β-defensin 1 | +2.19 | β-defensin 123 | +1.65 |
| β-defensin 4 | +3.06 | β-defensin 129 | +1.46 |

To test whether the sNAG-dependent defensin expression also occurred on the protein level, sNAG stimulated endothelial cells were subjected to immunofluorescence using antibodies directed against both α and β defensins. As shown in FIG. 7B, both β-defensin 3 and α-defensin 5 are up-regulated upon sNAG stimulation in this cell type. However, stimulation of primary human keratinocytes (HaCat) with sNAG did not cause increased expression of α-defensin but does cause an increase in the expression of β-defensin 3 (FIG. 7C). Taken together, these experiments suggest that sNAG stimulation results in an up-regulation of defensin peptides in both primary keratinocytes and primary endothelial cells.

6.2.2.2. sNAG-Dependent Defensin Expression Requires Akt1

Previously published data show that sNAG stimulation of primary endothelial cells results in increased integrin activation, Ets1 expression and MAP kinase activation. (Vournakis, J. N., et al., 2008, J Vasc Res. 45(3):222-32.) Findings position Akt1 upstream of Ets1 in endothelial cells and in *Drosophila*. (Lavenburg, K. R., et al., 2003, FASEB J. 17(15): 2278-80.) To begin to determine the signaling pathway responsible for the expression of defensins, endothelial cells were serum starved and pre-treated with pharmacological inhibitors directed against PI3K (wortmannin) or MAP kinase (PD098059) prior to sNAG stimulation. Quantitative real time PCR analysis shows that α-defensin 1 mRNA levels are greatly diminished after inhibition of either the PI3K/Akt pathway or the MAP kinase pathway (FIG. 8A). RT-PCR analysis of β-defensin 3 also shows that levels are decreased by the inhibition of these pathways as well (FIG. 8B). sNAG treatment of endothelial cells for a short time course leads to phosphorylation of Akt1, a standard indicator of its activation (FIG. 8C). To confirm that Akt1 is indeed required for defensin expression, lentiviral delivery of shRNA directed against Akt1 was used. Quantitative RT-PCR of serum starved endothelial cells infected with scrambled (SCR) control or Akt1 shRNA followed with sNAG treatment confirms that Akt1 expression is required for sNAG-dependent α-defensin expression (FIG. 8D). Since β-defensins are known to be expressed in epithelial cells, lentiviral delivery of shRNA directed against Akt1 was used in human keratinocytes (HaCat). sNAG treatment of serum starved keratinocytes infected with scrambled (SCR) control leads to a significant increase in β-defensin 3 expression that is abrogated by Akt1 knockdown (FIG. 8E). These results illustrate that sNAG treatment activates Akt1 in endothelial cells and strongly suggest that sNAG-dependent defensin expression requires Akt1 in both endothelial cells and keratinocytes.

6.2.2.3. sNAG Treatment of Cutaneous Wounds Increase Defensin Expression In Vivo To confirm the dependence of Akt1 for the expression of defensins in vivo, wild type and Akt1 null animals were used in an excisional wound healing model. Although most mammalian leukocytes express α-defensins (human, rabbit, rat, and hamster), mouse leukocytes do not express α-defensins. Therefore, β-defensin expression in these mouse models was focused on. Treatment of cutaneous wounds with a dried form of sNAG, a thin biodegradable membrane, for three days results in a statistically significant increase in β-defensin 3 expression in keratinocytes of wild type animals (FIG. 9A). Involucrin (Watt, F. M., 1983, J Invest Dermatol. 81(1 Suppl):100s-3s) staining (red) was used to mark the keratinocyte cell layers and show that the expression of β-defensin 3 is confined to the epidermal layer. To assess if sNAG-dependent defensin expression is dependent on Akt1, a similar assay was performed using an Akt1 null animal model. Wounds from Akt1 null mice treated with sNAG membranes show a markedly reduced induction of β-defensin 3 expression (FIG. 9A). To better visualize the epidermal layers that are expressing β-defensin 3, FIG. 9B shows a representative image of a sNAG treated wild type wound harvested on day 3. sNAG treatment of cutaneous wounds induced β-defensin 3 expression mainly in the suprabasal layers of skin (FIG. 9B). Quantitative analyses shown in FIG. 9C shows an approximate 5-fold increase in β-defensin 3 expression in sNAG treated wild type animals and that Akt1 is required for this increase.

6.2.2.4. sNAG Treatment Increases the Kinetics of Wound Closure in WT Animals

Previous results have shown an increased kinetics of wound closure in diabetic mouse models in response to sNAG treatment. sNAGs were tested for a similar affect in wild type animals. Excisional wounds were created in wild type animals which were either treated with the membrane form of sNAG or left untreated. Tissue sections were taken at 1, 3 and 5 days post wounding and subjected to H&E staining. As shown in FIG. 10, sNAG treatment of wild type wounds results in complete closure, as visualized by the solid line, at day 3 post wounding. This occurs two days earlier than in the control wounds. Akt1 null animals display a delay in wound closure; these animals do not fully close the wound until 7 days post wounding. The delay in wound closure in the Akt1 null animals is not rescued by sNAG treatment (data not shown). These findings suggest that sNAG not only induces defensin expression but also increases wound healing kinetics in wild type mice and may be a novel and effective therapeutic.

6.2.2.5. sNAG is an Effective Antimicrobial Against *S. Aureus*

Defensin peptides are known to possess antimicrobial properties that are active against gram-positive and gram-negative bacteria. Since treatment of endothelial cells with sNAG increases defensin expression (both α- and β-type) and treatment of cutaneous wounds with sNAG dramatically increases β-defensin 3 expression in vivo, the antimicrobial efficacy of sNAG treatment in bacterially infected wounds was assessed.

To determine if sNAG decreases bacterial load in cutaneous wounds, wild type and Akt1 null animals were subjected to cutaneous wound healing, followed by infection with *Staphylococcus aureus*. Infected wounds were either treated with sNAG or left untreated for 3 and 5 days post infection. As shown by the tissue gram staining in FIGS. 11A and 11B, wild type animals treated with sNAG show a significant reduction in gram positive staining by day 5 post wounding as compared with untreated wounds. In contrast, gram stained tissue derived from untreated wounds in Akt1 null animals at 5 days post wounding show an accumulation of neutrophils which stain gram positive (FIG. 11B), indicating a potential lack of bacterial clearance in these animals that is not rescued by sNAG treatment. These findings suggest that Akt1 null animals have a defect in immune clearance mechanisms which is not rescued by sNAG treatment.

To quantitate sNAG-specific bacterial changes in colony forming units (CFU), infected wounds from both wild type and Akt1 null mice either sNAG treated or untreated were harvested and cultured. As shown in FIG. 11C, at 5 days post wounding bacterial number is markedly reduced (10-fold) in wild type animals treated with sNAG. However, although the number of bacteria detected in the Akt1 null animals is reduced in comparison to wild type, sNAG treatment had a little effect on absolute bacterial number in the Akt1 null animals. At 3 days post-infection (FIG. 11D), there is a similar 10-fold decrease in CFU in sNAG treated wild type mice as compared to untreated controls. The sNAG treated Akt1 null animals show a 2-fold decrease in CFU as compared to untreated Akt1 null animals. In general, the Akt1 null animals have a lower bacterial load per wound which may be reflective of an Akt1-dependent effect on other processes in addition to defensin expression. These findings suggest that sNAG treatment results in a marked reduction in bacterial load in infected cutaneous wounds in wild type mice but not in Akt1 null mice, suggesting the possibility that defensins are mediating the anti-bacterial response.

To show that the antibacterial effect of sNAG treatment is not due to a direct effect of the nanofibers on bacterial growth or on their survival, S. aureus bacterial cultures were treated in solution with different amounts of sNAG, for 3 hours and colony forming units were determined. As shown in FIG. 11E, sNAG treatment had no direct effect on the growth of S. aureus, indicating that sNAG is not directly inhibiting bacterial growth and may then be working via the up-regulation of defensins.

6.2.2.6. Application of Defensin Peptide Mimics the sNAG Antibacterial Effect

To determine whether addition of defensin peptide can block bacterial infection similarly to that shown for sNAG treatment, wild type mice were wounded and inoculated with S. aureus as described above and then treated with biologically active human β-defensin 3 peptide (1.0 m) for three days. Tissue biopsies were stained using a tissue gram stain and CFU was quantitated. FIG. 11 F-G shows the results of these experiments. Infected mice treated with β-defensin 3 peptide have a decreased bacterial load, an approximate 7.5 fold decrease in viable bacteria (FIG. 11G), similar to that shown in wild type mice treated with sNAG.

One of the mechanisms by which defensin expression is induced is through stimulation by bacterial LPS, possibly through the activation of Toll like receptors. (Selsted, M. E. and A. J. Ouellette, 2005, Nat Immunol. 6(6):551-7.) To test whether bacterial infection alone is able to induce β-defensin expression within the time periods tested, expression of β-defensin was assessed in infected wounds from wild type animals after three days post wounding. As shown in FIG. 12A, bacterial infection alone does not induce the expression of β-defensin within 3 days of infection, as is shown with sNAG treatment. However, in wild type animals, sNAG treatment of infected wounds causes approximate 3- to 5-fold increase in the expression of β-defensin within a similar time period (FIG. 12B). These findings suggest that sNAG treatment rapidly induces the expression of defensin expression resulting in marked bacterial clearance in S. aureus infected wounds.

6.2.2.7. Antibodies Directed Against β-Defensin 3 Block the Antibacterial Effect of sNAG Since defensins are secreted proteins, the inventors hypothesized that antibodies directed against β-defensin 3 may be able to block the antibacterial activities. To test this hypothesis, wounds were created, infected with S. aureus and treated with sNAG as described above. The wounds were either treated with a β-defensin 3 antibody or an isotype control; one application each day for three days. Wound sections were obtained and stained for gram positive bacteria. As shown in FIG. 13A, sections derived from wounds treated with β-defensin antibody have more gram positive bacteria than those treated with isotype control antibodies. Each section shown was derived from the wound area directly under the scab. Quantitation of CFU in these wounds shows that neutralization of β-defensin 3 prior to sNAG treatment in S. aureus infected wounds results in a significant increase in bacteria. Animals that were treated with an IgG isotype control show an approximate 5-fold reduction in viable bacteria (FIG. 13B). Taken together, these results suggest that sNAG treatment not only results in the increased kinetics of wound healing but also promotes an endogenous anti-bacterial response and supports the use of this nanofiber as novel therapy to enhance wound healing while concurrently decreasing wound infection.

6.2.3 Conclusions

The findings presented here demonstrate that a marine diatom derived nanofiber, sNAG, may be used as a novel and effective method to enhance wound healing while concurrently decreasing wound infection. The data demonstrates that this FDA approved material, which is presently used for hemostasis, stimulates the expression of both α-type and β-type defensins in primary endothelial cells and an up-regulation of the β-type in primary keratinocytes.

Defensins are an essential component of the innate immune system. These peptides possess anti-microbial properties that are active against gram-positive and negative bacteria, fungi, and many viruses. Defensins are small (3-4 kDa), cysteine-rich cationic peptides found in mammals, insects, and plants that are classified into different families (α, β, and θ) based on their pattern of disulfide bonding. α-defensins are thought to be specific to neutrophils, are found in very high concentrations (comprising approximately 5-7% of the total cellular protein) (Ganz, T. and R. I. Lehrer, 1994, Curr Opin Immunol. 6(4):584-9), and are secreted during anti-microbial responses (Ganz, T., 1987, Infect Immun. 55(3):568-71). It has also been shown that rabbit alveolar macrophages possess α-defensins in levels comparable to rabbit neutrophils. (Ganz, T., et al., 1989, J Immunol. 143(4):1358-65.) β-defensins are found in epithelial cell types such as keratinocytes, mucosal epithelial cells (Harder, J., et al., 1997, Nature 387(6636):861; and Harder, J., et al., 2001, J Biol Chem. 276(8):5707-13), oral cavity tissues and salivary secretions (Mathews, M., et al., 1999, Infect Immun. 67(6):2740-5), and kidney where they can be up-regulated in response to infectious or inflammatory stimuli (Ganz, T. and R. I. Lehrer, 1994, Curr Opin Immunol. 6(4):584-9). Human β-defensin 1 (hDEFB1) is one of the most important antimicrobial peptides in epithelial tissues. Defensin expression and secretion could be extremely important for creating wound therapeutics. The anti-microbial action by defensins is considered part of innate immunity and is non-specific and broad spectrum. Therefore acquired bacterial resistance, as seen wih the overuse of antibiotics, is not an issue.

The data presented here also demonstrate that both in vitro and in vivo Akt1 is required for defensin expression. sNAG treatment decreases Staph *aureus* infection of cutaneous wounds in wild type control animals but not in similarly treated Akt1 null animals. It is also important to note that sNAG stimulation of wild type cutaneous wounds results in an increased kinetics of wound closure. Antibody blockade of β-defensin results in a reduction in the sNAG-antibacterial activity. Taken together these findings suggest a central role for Akt1 in the regulation of defensin expression that is responsible for the clearance of bacterial infection and that sNAG treatment activates these pathways in wild type animals.

The data that suggests that sNAG treatment of infected wounds could drastically decrease bacterial load in patients, at least in part, by the induction of defensin expression. *Staphylococcus aureus* is a bacterium frequently found colonizing the skin and in the nose. It is still a common cause of nosocomial infections, often causing postsurgical wound infections. *S. aureus* infections in hospitals have plagued healthcare workers for years and the widespread usage of antibiotics for treatment has lead to antibiotic resistant strains. The data presented herein shows that treatment of Staph infected wounds with sNAG dramatically decreased the bacterial load. For example, the lack of dark purple gram staining in the treated WT mice in FIGS. 11A and 11B indicates that the *S. aureus* infection has been cleared from these wounds. Both the in vitro and in vivo data provides strong evidence for the use of Taliderm/sNAG in the treatment of wounds to decrease bacterial infection and therefore enhance wound healing.

Control experiments indicate that the antibacterial effect of sNAG is not due to a direct interaction of the material with the bacteria but is due to downstream affects such as the regulation of defensins by Akt1 activation. It is widely accepted that defensins are important players in innate immunity and function in antimicrobial activities. Most of the evidence for their function is the direct killing of bacteria by in vitro mixing experiments with purified defensin peptides (Selsted, M. E. and A. J. Ouellette, 2005, Nat Immunol. 6(6):551-7) or in similar experiments as shown in FIGS. 11A-G with direct application of the purified active peptide. The data here show that an induction of defensin expression in wild type animals using a topical application of sNAG results in an antibacterial response. It has recently been shown that transgenic mouse models expressing the human defensin 5 gene are resistant to *S. typhimurium*, an infection that results in death of wild-type animals (Salzman, N. H., et al., 2003, Nature 422(6931):522-6) again suggesting the importance of defensins in the regulation of the antimicrobial response.

It has been accepted that the α-subtype of defensins are specifically expressed in neutrophils, whereas the β-type defensins are epithelial in origin. β-type defensin expression induced in response to sNAG in human keratinocytes both in culture and in the cutaneous wound healing model was detected. The in vivo data illustrates that β-defensin 3 is mainly expressed in the suprabasal layers after treatment with sNAG. This is consistent with previous data which localized human β-defensin 2 to the spinous and granular layers of the skin. (Oren, A., et al., 2003, Exp Mol Pathol. 74(2):180-2.) The skin is in constant contact with injury and infection and functions not only as a mechanical barrier but also maintains the ability to mount an active defense against infection. The expression of β-defensin in the outer layers of skin supports their role in cutaneous innate immunity. However, the data show that sNAG specifically stimulates the expression of three different α-defensins (1, 4 and 5) in endothelial cells. This is shown by RT-PCR, gene array analysis, immunofluorescence and ELISA (data not shown). The interaction between endothelial cells and leukocytes in tissue repair is one of the initial and most important steps in wound healing. The process of extravasation of leukocytes from the vasculature is initiated by chemotactic factors, therefore; it is interesting that α-defensins are induced by sNAG and may contribute to the necessary neutrophil/endothelial cellular interactions. More recently, it has come to light that defensins exhibit biological activities beyond the inhibition of microbial cells, including their contribution to the adaptive immune response by exhibiting chemotactic activity on dendritic (Hubert, P., et al., 2007, FASEB J. 21(11):2765-75) and T cells, monocytes, and macrophages (Garcia, J. R., et al., 2001, Cell Tissue Res. 306(2):257-64) and keratinocytes (Niyonsaba, F., et al., 2007, J Invest Dermatol. 127(3):594-604). Previous work shows that human beta defensins 1 and 2 have the ability to chemoattract immature dendritic cells and T cells through the CC-chemokine receptor 6 (CCR6) (Yang, D., et al., 1999, Science 286(5439):525-8), and that human beta defensin 2 can chemoattract TNFα treated neutrophils via the CCR6 receptor (Niyonsaba, F., H. Ogawa, and I. Nagaoka, 2004, Immunology 111(3):273-81). Human β-defensin 2 and 3 have also been shown to induce chemotaxis by interacting with CCR2, a receptor expressed on macrophages, monocytes, and neutrophils. (Rohrl, J., et al., 2010, J Immunol, 2010.) Interestingly, the data show that sNAG treatment induces both α and β-defensin expression in endothelial cells. Taken together, the recent data suggest that defensins may mediate wound healing not only by their antimicrobial properties, but also by being chemotactic for other cell types necessary for proper healing. However, application of β-defensin 3 alone did not result in an increase in wound closure (data not shown) implying that topical application of a single defensin does not sustain the cellular interactions required for increased chemo attraction, cellular recruitment and wound closure.

The in vivo data using both wild type and Akt1 knockout animals confirms the requirement for Akt1 in sNAG-induced β-defensin 3 expression. Since mouse leukocytes do not express α-defensins like most other mammalian leukocytes (Ganz, T., 2004, C R Biol. 327(6):539-49) in vivo α-defensin staining of infiltrating immune cells was not possible. Treatment of airway epithelial cells in vitro with alpha defensins 1-3 causes a dose and time-dependent increased cell migration that requires activation of PI3K and MAPK pathways. (Aarbiou, J., et al., 2004, Am J Respir Cell Mol Biol. 30(2):193-201.) sNAG stimulation of endothelial cells has been shown to result in the activation of MAPK (Vournakis, J. N., et al., 2008, J Vasc Res. 45(3):222-32) and in data presented here, pharmacological inhibition of MEK also inhibits the expression of the defensins in vitro. These findings suggest that both pathways impinge on the regulation of defensin expression by sNAG, however, Akt1 ablation results in a marked reduction of its expression both in vitro and in vivo. In myeloid cells, β-defensin 1 expression is controlled at the level of transcription, in part, by the Ets-family member PU. 1. (Yaneva, M., et al., 2006, J Immunol. 176(11):6906-17; and Ma, Y., Q. Su, and P. Tempst, 1998, J Biol Chem. 273(15):8727-40.) PU.1 is a downstream target of Akt1 in the B-cell lineage. (Rieske, P. and J. M. Pongubala, 2001, J Biol Chem. 276(11):8460-8.)

In primary endothelial cells it has been shown that Akt1 is upstream of Ets1 both in vitro and in vivo during *Drosophila* tracheal development. (Lavenburg, K. R., et al., 2003, FASEB J. 17(15):2278-80.) sNAG stimulation of endothelial cells results in increased expression of Ets1 (probably through Akt1) which is required for the migration of endothelial cells. (Vournakis, J. N., et al., 2008, J Vasc Res. 45(3):222-32.)

Thus far, sNAG treatment has resulted in a series of downstream activities; hemostasis, cell migration, cell proliferation, increased wound closure, and as described here, stimulation of the innate immune response resulting in anti-bacterial functions.

Given the dramatic increase of diabetic patients within the population who present with chronic wounds and complications due to wound infection, new clinical treatments are in high demand. Here, marine derived pGlcNAc nanofibers are described that not only increase the kinetics of wound healing but act to stimulate innate immunity thus providing anti-bacterial activity. The obvious importance of these observations is the application to nosocomial infections. Of the nosocomial infections, surgical wound infections predominate; with statistics showing up to 8% of all surgical patients. The direct cost of these types of infections is approximately 4.5 billion dollars per year. Given that defensins are part of the innate immune system, activation of these pathways will preclude the generation of resistant organisms as well as allow for the antibiotic-independent clearance of bacterial infection. Use of sNAG in a hospital setting would defray much of the cost and markedly reduce the production of antibiotic resistant species. Taken together, these findings suggest that these marine derived pGlcNAc nanofibers will be highly beneficial in the clinical arena.

6.3 Example 3: sNAG is an Effective Antimicrobial Against *Pseudomonas aeruginosa*

This example demonstrates that sNAG nanofibers have an anti-bacterial effect against *Pseudomonas aeruginosa* in vivo.

Materials and Methods: Wild Type C57Bl/6 male mice between 8-12 weeks old were wounded created using a 4 mm biopsy punch (Miltex), to create two identical wounds on each flank. Mice were anesthetized using an $O_2$/Isoflurane vaporizing anesthesia machine (VetEquip, Inc.). Isoflurane was used at 4% for induction; 2% for surgery. Prior to surgery hair was removed by *Pseudomonas aeruginosa* were picked and cultured overnight at 37° and adjusted to an absorbance of $OD_{600}$=0.53. Each wound was inoculated with $1.5 \times 10^9$ cfu/wound of *P. aeruginosa*. After 30 minutes post inoculation, wounds were either treated with sNAG membrane moistened with distilled water (test group, n=6) or left untreated (control group, n=6). On day 3 animals were euthanized and entire wounds were harvested including the surrounding skin using an 8 mm biopsy punch (Miltex). One wound per animal was fixed overnight in 4% paraformaldehyde at 4° C., embedded in paraffin, and sectioned for analysis, and the other wound was cultured and plated on LB media without antibiotic for bacterial quantitation. For culturing, wound sections were placed in 0.5 ml bacterial media an incubated for 30 min at 37° C. while shaking. Colony forming units (CFU) were quantitated using a dilution series plated overnight at 37° C. Number of colonies per plate/per dilution were counted and CFU/ml were calculated.

Results: The efficacy of sNAG treatment of wounds infected with gram negative bacteria was assessed. As shown in FIG. 14, at 3 days post infection bacterial number is markedly reduced (more than 2 fold) in animals treated with sNAG in comparison to untreated animals. These findings suggest that sNAG treatment results in a marked reduction in bacterial load of gram negative bacteria, and specifically *P. aeuruginosa*, in infected cutaneous wounds (in addition to reduction in bacterial load of gram positive bacteria shown in Example 2).

6.4 Example 4: sNAG Nanofibers Upregulate Expression of a Number of Defensins and Toll Receptor Genes This example demonstrates that a number of defensins and Toll-like receptors are up-regulated by sNAG treatment of human endothelial cells.

Materials and Methods: Human Chip probes were printed on epoxy slides. HUVEC cells were cultured as described in section 6.2, and treated with sNAG nanofibers ("sNAG") for 5 hours. RNA was extracted with RNAsol (Teltest, Inc.) following manufacturer's instructions, amplified using Amino Allyl MessageAMP™ II aRNA amplification kit (Applied Biosystems), and labeled. The slides were prepared for hybridization with aRNA by soaking in blocking solution (Sigma Tris-buffered saline pH8.0, in 1000 ml $dH_2O$, 1% BSAw/v, NaN3 to 0.05%) at RT O/N, then rinsed and dryed. Samples containing labeled target aRNA from sNAG-treated cells were hybridized with the slides (65 ul/slide; denatured at 95° C. for 5 min; hybridized for 48 hours at 37° C. in 0.1% SDS and 5×SSC and 1% BSA), rinsed and dryed. The slides were scanned and hybridization detected using Perkin-Elmer Scan Array equipment and ScanArray Express software V3.0, updated. To identify up-regulated genes, microarray data was analyzed using Agilent GeneSpring GX v.11 Bioinformation Data Analysis.

Genes of interest analyzed: IL-1, CEACAM3, SPAG11, defensins ("DEFA"=α-defensin, and "DEFB"=(β-defensin); Toll-like receptors ("TLR"), SIGIRR (Single IG IL-1-related receptor), and TRAF6 (TNF receptor associated factor 6). Positive controls: 1433Z (Tyrosine-3-monohydrogenase/ tryptophan 5 monohydrogenase action protein); GAPD (glyceraldehydes-3-phosphate dehydrogenase); RPL13A (Ribosomal protein L13a); UBC (Ubiquitin C); ACTB (Actin B).

Results: Results of the microarray gene chip analyses and Q-PCR validation of microarray results are presented in Tables II-VI below. Using a custom gene chip it was determined that a number of defensins and Toll-like receptors are up-regulated by sNAG treatment of human endothelial cells.

Toll-like receptors (TLRs) are highly conserved receptors that recognize specific molecular patterns of bacterial components leading to activation of innate immunity. Interestingly, *Drosophila* lack an adaptive immune system but are still resistant to microbial infections. (Imler, J. L. and J. A. Hoffmann, 2000, Curr Opin Microbiol, 3(1):16-22.) This host defense is the result of an innate immune system that provides protection by synthesizing the antimicrobial peptides dToll and 18-wheeler which are induced by TLRs. (Lemaitre, B., et al., 1996, Cell 86(6):973-83; and Williams, M. J., et al., 1997, EMBO J. 16(20):6120-30.) Recent work has also linked human defensin expression to TLR activation. Human (β-defensin 2 was shown to be induced in airway epithelial cells in a TLR-2 dependent manner. (Hertz, C. J., et al., 2003, J Immunol. 171(12): p. 6820-6.) Toll-like receptor 4 has been shown to mediate human β-defensin 2 inductions in response to *Chlamydia pneumonia* in monocytes. (Romano Carratelli, C., et al., 2009, FEMS Immunol Med Microbiol. 57(2): 116-24.) Importantly, the PI3K/Akt pathway is a key component in TLR signal transduction, controlling cellular responses to pathogens. (Weichhart, T. and M. D. Saemann, 2008, Ann Rheum Dis. 67 Suppl 3: iii70-4.) Since it is known that stimulation of TLRs can lead to increased defensin synthesis, this work suggests the potential for sNAG as a stimulator of innate immunity and bacterial clearance via the activation of Akt1.

TABLE II

List of some genes up-regulated in response to sNAG stimulation

| Gene | Function |
|---|---|
| IL-1 | Pro-inflammatory cytokine involved in immune defence |
| CEACAM3 | Cell adhesion molecule which directs phagocytosis of several bacterial species |
| SPAG11 | β-defensin-3 like molecule that exhibits antimicrobial properties |
| Defensins | A series of defensins that exhibit antimicrobial activity |
| TLRs | Toll-like receptors: important for stimulation of cellular responses toward infection |

| GENE | LIGAND/FUNCTION | FOLD INDUCTION |
|---|---|---|
| TLR1 | Triacyl lipopeptides from bacteria and mycobacteria | 7.6 |
| TLR4 | LPS, viral proteins, Hsp60 (Chlamydia) | 5.064 |
| TLR7 | synthetic compounds | 3.271 |
| TLR8 | synthetic compounds | 2.067 |
| TRAF6 | Downstream signalling modulator | 6.167 |
| SIGRR | IL-1 receptor related TLR modulator | 5.895 |

TABLE III

Defensin Microarray Gene Expression
(HUVEC Response to sNAG 10 ug/ml 5 hours)

| Gene Name [Oligo ID] | HUVEC_10s_48h37C normalized (Fold) |
|---|---|
| D107A_HUMAN [H300005354] | 4.2 (2.6 to 5.2) |
| DEFA4 [H200000646] | 4.2 (3.243 to 4.946) |
| DEFA5 [H200005803] | 4.8 (3.664 to 6.123) |
| DEFB1 [H200004191] | 2.7 (1.7 to 3.7) |
| DEFB103A [H300008014] | 9.8 (7.4 to 12.5) |
| DEFB118 [H200017001] | 2.7 (1.502 to 4.779) |
| DEFB119 [H300002796] | 6.2 (4.68 to 8.04) |
| DEFB123 [H300009262] | 8.9 (7.791 to 11.1) |
| DEFB124 [H300001942] | 3.8 (1.6 to 5.1) |
| DEFB126 [H200012496] | 9.2 (8.286 to 10) |
| DEFB129 [H300005026] | 5.2 (4.338 to 6.277) |
| ACTB_HUMAN [H300006234] | 6.8 (6.603 to 7.284) |
| GAPD [H200007830] | 16.9 (12.81 to 21.13) |
| RPL13A [opHsV04TC000041] | 9.4 (7.311 to 12.01) |
| UBC [H200014214] | 7.2 (5.789 to 9.979) |
| 1433Z_HUMAN [opHsV04TC000038] | 0.6 (0.4 to 0.844) |

TABLE IV

DEFCB3 Microarray Gene Validation
(AB Prism 7000; sNAG (10 ug/ml), HUVEC for 5 h)
TaqMan Relative qPCR Fold Change Calculations (ABI method)

| Sample | DEFB3 | 1433z | $\Delta Ct$ = DEFB3 − 1433z | $\Delta \Delta Ct$ = $\Delta Ct$treated − $\Delta Ct$ untreated | Fold difference in DEFB3 relative to untreated |
|---|---|---|---|---|---|
| untreated | 37.41 ± 0.74 | 14.71 ± 0.26 | 22.7 ± 0.78 | 0.00 ± 0.78 | 1.4 (1.22-1.7) |
| treated | 40.30 ± 1.0 | 17.84 ± 0.07 | 22.46 ± 1.0 | −0.24 ± 1.0 | 1.8 (1.24-2.36) |

TABLE V

Toll-Like Receptors Microarray Gene Expression

| Gene Name [Oligo ID] | Fold Change |
|---|---|
| SIGIRR [opHsV0400002471] | 5.895 (3.916 to 7.926) |
| TLR1 [H300000701] | 7.612 (3.796 to 11.33) |
| TLR4 [H200007406] | 5.064 (1.085 to 10.66) |
| TLR7 [H200008345] | 3.271 (1.938 to 3.938) |
| TLR7 [H300006695] | 2.2 (1.5 to 2.7) |
| TLR8 [H200016915] | 2.067 (1.8 to 2.2) |
| TRAF6 [H200010465] | 6.167 (5.2 to 7) |
| 1433Z_HUMAN [opHsV04TC000038] | 0.573 (0.4 to 0.844) |

TABLE VI

Real Time Q-PCR Gene Validation of TLR1 & 4
(HUVEC, 10 ug/ml sNAG for 5 h)

| Sample | Target $C_T$ ave | Target $C_T$ sd | Reference (1433z) $C_T$ ave | Reference (1433z) $C_T$ sd | $\Delta C_T$ = Target$C_T$ − 1433z$C_T$ | $\Delta C_T$ sd = $(S_{target}^2 + S_{reference}^2)^{1/2}$ | $\Delta \Delta Ct$ = $\Delta Ct_{test\ sample(treated)}$ − $\Delta Ct_{Calibrator(untreated)}$ | $\Delta \Delta Ct$ sd = $\Delta Ct$ sd | Fold up $2^{-(\Delta \Delta Ct + sd)}$ | Fold down $2^{-(\Delta \Delta Ct - sd)}$ | Fold ave |
|---|---|---|---|---|---|---|---|---|---|---|---|
| TLR1 | | | | | | | | | | | |
| untreated | 31.12 | 1.2 | 17.84 | 0.34 | 13.28 | 1.25 | 0 | 1.25 | 0.42 | 2.37 | 0.83 |
| treated | 28.54 | 0.37 | 17.53 | 0.2 | 11.01 | 0.42 | −2.27 | 0.42 | 3.60 | 6.46 | 5.03 |

TABLE VI-continued

Real Time Q-PCR Gene Validation of TLR1 & 4
(HUVEC, 10 ug/ml sNAG for 5 h)

| Sample | Target $C_T$ ave | Target $C_T$ sd | Reference (1433z) $C_T$ ave | Reference (1433z) $C_T$ sd | $\Delta C_T =$ Target$C_T$ − 1433z$C_T$ | $\Delta C_T$ sd = $(S_{target}^2 + S_{reference}^2)^{1/2}$ | $\Delta\Delta Ct =$ $\Delta Ct_{test\ sample(treated)} - \Delta Ct_{Calibrator(untreated)}$ | $\Delta\Delta Ct$ sd = $\Delta Ct$ sd | Fold up $2^{-(\Delta\Delta Ct+sd)}$ | Fold down $2^{-(\Delta\Delta Ct-sd)}$ | Fold ave |
|---|---|---|---|---|---|---|---|---|---|---|---|
| TLR4 | | | | | | | | | | | |
| untreated | 26.97 | 0.44 | 17.84 | 0.34 | 9.13 | 0.56 | 0 | 0.56 | 0.68 | 1.47 | 0.62 |
| treated | 25.04 | 0.38 | 17.53 | 0.2 | 7.51 | 0.43 | −1.62 | 0.43 | 2.28 | 4.14 | 3.21 |

6.5 Example 5: sNAG and Long Fiber NAG Differ in their Gene Expression Profiles

This example demonstrates that sNAG nanofibers differ from long p-GlcNAc fibers in their effect on gene expression, and specifically in their effect on expression of some of the defensins and Toll-like receptors.

Materials and Methods: Human Defensin Chip probes (concentration: 20 uM, quantity 18-20, solvent: SSC based spotting buffer) were printed on epoxy slides using standard techniques. HUVEC and HaCat cells were cultured as described in section 6.2, and treated with either long fibers ("LNAG") or sNAG nanofibers ("sNAG"), for 2 hours or 20 hours. RNA was extracted with RNAsol (Teltest, Inc.) following manufacturer's instructions, and amplified using Amino Allyl MessageAMP™ II aRNA amplification kit (Applied Biosystems). During RNA amplification, aRNA from cells treated with LNAG and aRNA from cells treated with sNAG was differentially labeled with Cy3 or Cy5 fluorescent dyes. The slides were prepared for hybridization with aRNA by soaking in blocking solution (Sigma Tris-buffered saline pH8.0, in 1000 ml dH$_2$O, 1% BSAw/v, NaN3 to 0.05%) at RT O/N, then rinsed and dryed. Samples containing equal amounts of differentially labeled target aRNA from LNAG and sNAG-treated cells were mixed, hybridized with the slides (65 ul/slide; denatured at 95° C. for 5 min; hybridized for 48 hours at 37° C. in 0.1% SDS and 5×SSC and 1% BSA), rinsed and dryed. The following exemplary graphs in Table VII illustrate experimental set up:

The slides were scanned and hybridization detected using Perkin-Elmer ScanArray equipment and ScanArray Express software V3.0, updated. For each slide, Cy5, Cy3 and composite fluorescence was visualized. To identify up-regulated and down-regulated genes microarray data was analyzed using Agilent GeneSpring GX v.11 Bioinformation Data Analysis. Genes of interest analyzed: DEFA1, DEFA3, DEFA4, DEFA5, DEFA6, DEFB1, DEFB013A, DEFB104A, DEFB105B, DEFB108B, DEFB112, DEFB114, DEFB118, DEFB119, DEFB123, DEFB124, DEFB125, DEFB126, DEFB127, DEFB128, DEFB129, DEFB131, and DEFB4 ("DEFA"=α-defensin, and "DEFB"=(β-defensin); TLR1, TLR10, TL2, TLR3, TLR4, TLR5, TLR6, TLR7 and TLR8 ("TLR"=Toll receptor); SIGIRR (Single IG IL-1-related receptor); IRAK2 (IL-1 receptor-associated kinase 1); TRAF6 (TNF receptor associated factor 6); D106A (β-defensin 106), D107A (β-defensin 107). Negative controls: three random sequences (1, 2, 3). Positive controls: 1433Z (Tyrosine-3-monohydrogenase/tryptophan 5 monohydrogenase acttion protein); GAPD (glyceraldehydes-3-phosphate dehydrogenase); RPL13A (Ribosomal protein L13a); UBC (Ubiquitin C); ACTB (Actin B).

Results: Results of the microarray gene chip analyses are presented in Tables VIII and IX below. Table VIII shows gene expression in human umbilical vein endothelial cells

TABLE VII

Labeling of aRNA

| Name | aRNA ng/ul (100 ul) | 260/280 nm | 20 ug for label (ul) | dye used | labeled conc. Pmol/ul | 260/280 | total labeled aRNA (20 ul) | |
|---|---|---|---|---|---|---|---|---|
| HaCat_e14d3_ctr | 897.42 | 2.09 | 22.29 | cy3 | 851.58 | 1.34 | 17031.6 | |
| HaCat_e14d3_LNAG100 | 1339.08 | 2.07 | 14.94 | cy5 | 687.01 | 1.87 | 13740.2 | |
| HaCat_e14d3_sNAG100 | 1515.62 | 2.05 | 13.20 | cy5 | 519.15 | 1.93 | 10383 | |
| HUVEC_e18d4_ctr | 1656.37 | 2.05 | 12.07 | cy3 | 529.11 | 1.88 | 19577.07 | 37 ul |
| HUVEC_e18d4_LNAG100 | 1078.63 | 2.07 | 18.54 | cy5 | 760.26 | 1.9 | 15205.2 | |
| HUVEC_e18d4_sNAG100 | 1447.87 | 2.06 | 13.81 | cy5 | 617.57 | 1.84 | 12351.4 | |

Labeled aRNA Hybridization

| | Sample ID | Total aRNA/slide (ng) | aRNA conc. (ng/ul) | Total vol. (μl) | 10% SDS (μl) | 20xSSC (μl) | D H$_2$O (μl) | Total Vol (ml) | chip ID 37° C. 48 h | Chip ID 37 C. 48 h |
|---|---|---|---|---|---|---|---|---|---|---|
| HaCat | Actr | 800 | 851.58 | 0.9 | 2 | 50 | 125.9 | 200 | D1038 | D1034 |
| | ALNAG100 (Mix 1) | 800 | 687.01 | 1.2 | 0 | 0 | | | | |
| | Actr | 800 | 851.58 | 0.9 | 2 | 50 | 125.5 | 200 | D1037 | D1033 |
| | AsNAG100 (Mix 2) | 800 | 519.15 | 1.5 | 0 | 0 | | | | |
| HUVEC | VCtr | 800 | 529.11 | 1.5 | 2 | 50 | 125.4 | 200 | D1036 | D1032 |
| | VLNAG100 (Mix 3) | 800 | 760.26 | 1.1 | | | | | | |
| | Vctr | 800 | 529.11 | 1.5 | 2 | 50 | 125.2 | 200 | D1035 | D1031 |
| | VsNAG100 (Mix4) | 800 | 617.57 | 1.3 | | | | | | |

("HUVEC") after 2 h or 24 h exposure to either LNAG fibers or sNAG nanofibers. Table IX shows gene expression in human keratinocyte cell line (HaCat) after 2 h or 24 h exposure to either LNAG fibers or sNAG nanofibers. The results demonstrate that gene expression profile induced by long poly-N-acetylglucosamine fibers ("LNAG") differs from the gene expression profile induced by sNAG nanofibers ("sNAG"). Specifically, LNAG and sNAG differ in their effect on expression of defensin genes and Toll receptor genes.

TABLE VIII

Microarray Defensin Gene Expression in Human Umbilical Vein Endothelial Cells (HUVEC), Fold Change

| Name | [2 h, LNAG] | [2 h, sNAG] |
|---|---|---|
| 1433Z_HUMAN | 0.039 | 0.329 |
| ACTB_HUMAN | −0.140 | 0.032 |
| D106A_HUMAN | −1.376 | −0.195 |
| D107A_HUMAN | 1.825 | 1.431 |
| DEFA1 | 0.407 | −1.107 |
| DEFA3 | 0.000 | 0.528 |
| DEFA4 | −1.007 | −0.123 |
| DEFA5 | −0.863 | 0.451 |
| DEFA6 | 1.969 | 0.805 |
| DEFB1 | 0.315 | 1.441 |
| DEFB103A | 1.426 | 1.486 |
| DEFB104A | 1.296 | 2.260 |
| DEFB105B | 0.616 | 0.667 |
| DEFB108B | 2.210 | 0.441 |
| DEFB112 | 0.000 | −0.528 |
| DEFB114 | 0.000 | 0.667 |
| DEFB118 | −0.142 | 0.631 |
| DEFB119 | 0.137 | 1.472 |
| DEFB123 | 1.664 | 1.814 |
| DEFB124 | 1.242 | 1.533 |
| DEFB125 | 1.169 | 1.969 |
| DEFB126 | −0.064 | 0.801 |
| DEFB127 | 1.723 | 0.000 |
| DEFB128 | 1.602 | −0.528 |
| DEFB129 | 1.528 | 0.407 |
| DEFB131 | −0.333 | 0.636 |
| DEFB4 | 0.406 | 0.567 |
| GAPD | 0.420 | 0.602 |
| IRAK2 | −0.035 | 1.106 |
| RPL13A | 0.671 | 1.329 |
| SIGIRR | 0.358 | 1.481 |
| TLR1 | −0.194 | 1.089 |
| TLR10 | 0.000 | −0.333 |
| TLR2 | 0.653 | 2.078 |
| TLR3 | −0.528 | −0.333 |
| TLR4 | 0.613 | 2.073 |
| TLR5 | 1.723 | 1.181 |
| TLR6 | 1.333 | 0.528 |
| TLR7 | 1.839 | 1.274 |
| TLR8 | −0.033 | 0.843 |
| TRAF6 | 1.569 | 0.472 |
| UBC | −0.285 | 0.072 |

| Name | [20 h, LNAG] | [20 h, sNAG] |
|---|---|---|
| 1433Z_HUMAN | −0.046 | −0.180 |
| ACTB_HUMAN | 0.874 | −0.413 |
| D106A_HUMAN | 1.107 | 0.522 |
| D107A_HUMAN | −1.007 | 0.372 |
| DEFA1 | −0.333 | 0.384 |
| DEFA3 | 1.195 | −2.335 |
| DEFA4 | 0.496 | 2.636 |
| DEFA5 | −0.287 | −0.476 |
| DEFA6 | 0.333 | −1.402 |
| DEFB1 | 1.933 | 0.413 |
| DEFB103A | 0.628 | 1.348 |
| DEFB104A | 1.543 | 0.344 |
| DEFB105B | 0.723 | −0.162 |
| DEFB108B | 0.351 | 1.895 |
| DEFB112 | −0.862 | 1.107 |
| DEFB114 | −0.862 | 1.799 |
| DEFB118 | 0.456 | 0.577 |
| DEFB119 | 0.808 | −1.530 |
| DEFB123 | 0.390 | −0.375 |
| DEFB124 | 1.113 | 1.357 |
| DEFB125 | 1.269 | −2.053 |
| DEFB126 | 1.818 | 0.385 |
| DEFB127 | 0.000 | 1.085 |
| DEFB128 | 0.805 | 2.238 |
| DEFB129 | 1.936 | −0.005 |
| DEFB131 | −0.723 | −0.608 |
| DEFB4 | 0.401 | −0.190 |
| GAPD | 0.616 | 0.324 |
| IRAK2 | 1.084 | 0.984 |
| RPL13A | 0.789 | 0.208 |
| SIGIRR | 1.870 | −0.050 |
| TLR1 | 0.196 | −0.631 |
| TLR10 | −0.528 | 0.644 |
| TLR2 | 1.848 | 4.494 |
| TLR3 | −1.484 | −1.361 |
| TLR4 | 2.616 | 0.634 |
| TLR5 | 0.723 | −0.417 |
| TLR6 | 0.246 | −0.482 |
| TLR7 | −0.160 | 0.199 |
| TLR8 | −0.371 | 1.219 |
| TRAF6 | 0.731 | 3.266 |
| UBC | −0.009 | −0.265 |

TABLE IX

Microarray Defensin Gene Expression in Human Keratinocyte Cell Line (HaCat), Fold Change

| Name | 2 h, LNAG | 2 h, sNAG |
|---|---|---|
| 1433Z | 0.255 | −0.282 |
| GAPD | 0.041 | −0.191 |
| RPL13A | −0.532 | 0.698 |
| UBC | 0.136 | −0.065 |
| ACTB | 0.130 | 0.447 |
| Negative Control | 0.000 | 0.000 |
| Negative Control | 0.000 | 0.000 |
| Negative Control | 0.000 | 0.000 |
| DEFB1 | −0.647 | 1.390 |
| DEFB126 | 0.348 | 1.737 |
| DEFB129 | 0.382 | 1.464 |

| Name | 20 h, LNAG | 20 h, sNAG |
|---|---|---|
| 1433Z | 0.000 | 0.205 |
| GAPD | 0.000 | 0.378 |
| RPL13A | 0.000 | −1.187 |
| UBC | 0.834 | −0.023 |
| ACTB | 0.333 | 0.988 |
| Negative Control | 0.000 | 0.000 |
| Negative Control | 0.000 | 0.000 |
| Negative Control | 0.000 | 0.000 |
| DEFB1 | −0.333 | −0.426 |
| DEFB126 | 1.000 | 0.744 |
| DEFB129 | −0.528 | −0.931 |

6.6 Example 6: Effect of Irradiation on sNAG Membranes Method of Preparation of sNAG Membrane. The sNAG membrane is derived form microalgal pGlcNAc fibers produced as previously described (see Vournakis et al. U.S. Pat. Nos. 5,623,064; and 5,624,679, the content of each of which is incorporated herein by reference in its entirety). Briefly, microalgae were cultured in unique bioreactor conditions using a defined growth media. Following the harvest of microalgae from high-density cultures, fibers were isolated via a stepwise separation and purification process resulting in batches of pure fibers suspended in water for injections (wfi). Fibers were formulated into patches by concentration and oven drying, and were packaged and sterilized by gamma-irradiation. Fiber dimensions average 20-50 nm×1-2 nm×~100 μm. Batches of fibers were individually quality controlled using chemical and physical test parameters, and each batch met strict purity criteria prior to release. Final batches were required to be substantially free of proteins, metal ions, and other components. The fibers were then shortened by irradiation to produce sNAG membranes. Briefly, the starting material contained 60 g of pGlcNAc slurry at a concentration of 1 mg/mL. The concentration of the pGlcNAc slurry was confirmed by filtering 5 mL into a 0.2 um filter. 15 L of pGlcNAc slurry containing 15 g pGlcNAc was filtered until formation of a wet cake. The wake cake was then transferred into a foil pouch, which is a gamma radiation compatible container, and subjected to 200 kGy gamma radiation. Other irradiation conditions were tested for their effects on pGlcNAc compositions, as reflected in FIG. 15A.

Figure 15A:
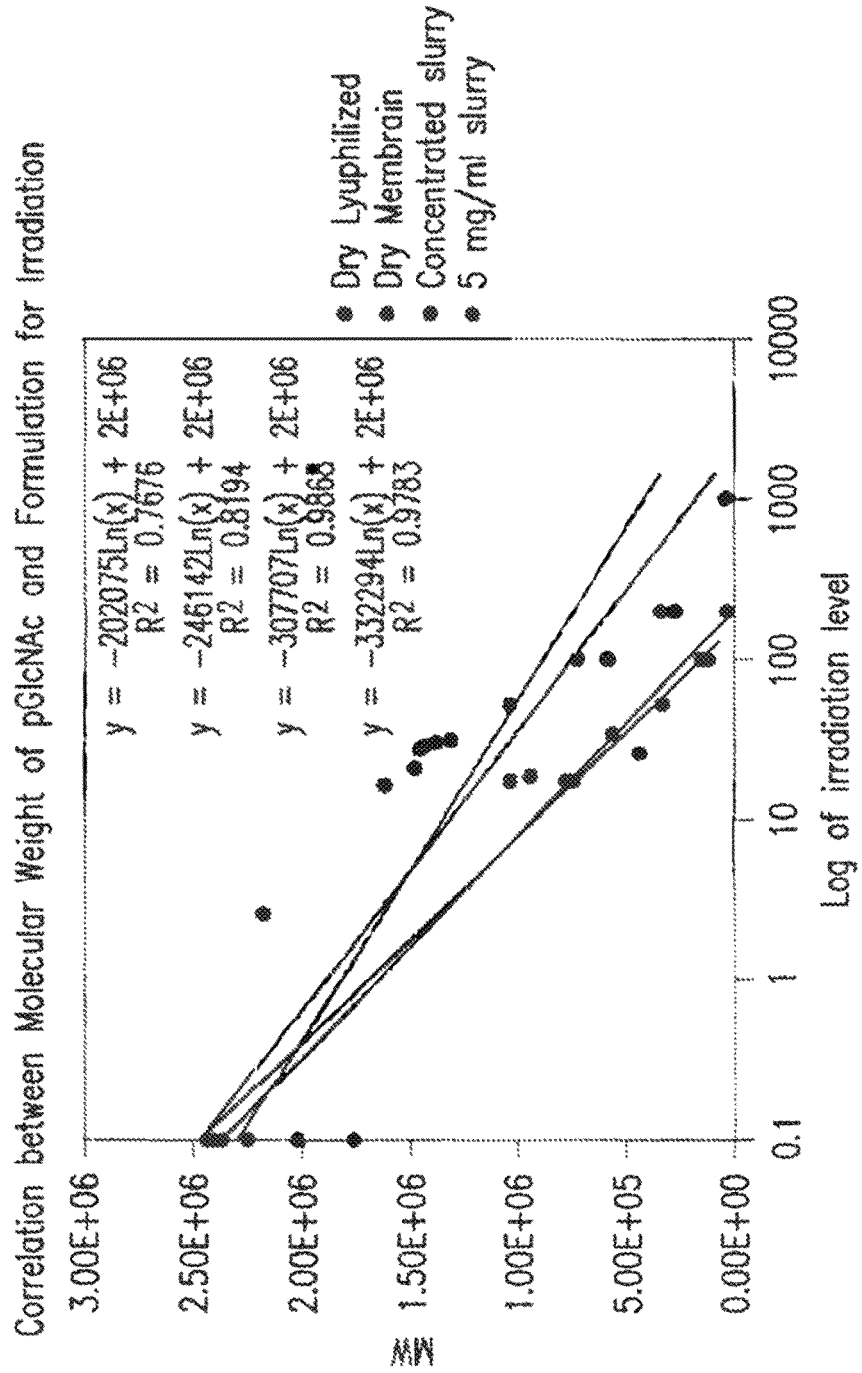
Figure 15B:
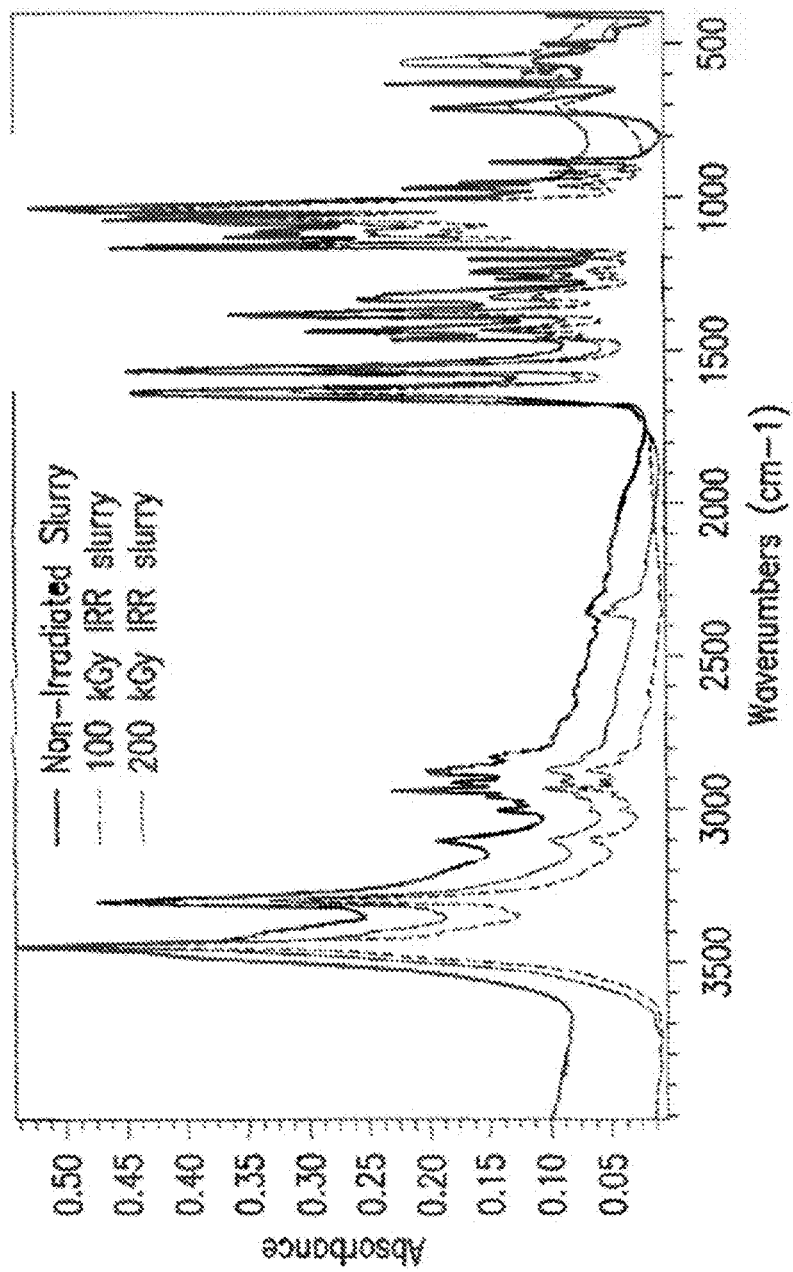

Effect of Irradiation on pGlcNAc Membranes. While irradiation reduces the molecular weight of pGlcNAc, irradiation did not disturb the microstructure of the fibers. pGlcNAc was irradiated under different conditions: as a dry, lyophilized material; as a dry membrane; as a concentrated slurry (30:70 weight by volume); and as a dilute slurry (5 mg/ml). A suitable molecular weight reduction (to a molecular weight of 500,000-1,000,000 daltons) was achieved at an irradiation dose of 1,000 kgy for dry polymer, and 200 kgy for wet polymer (FIG. 15A).

Figure 15C:
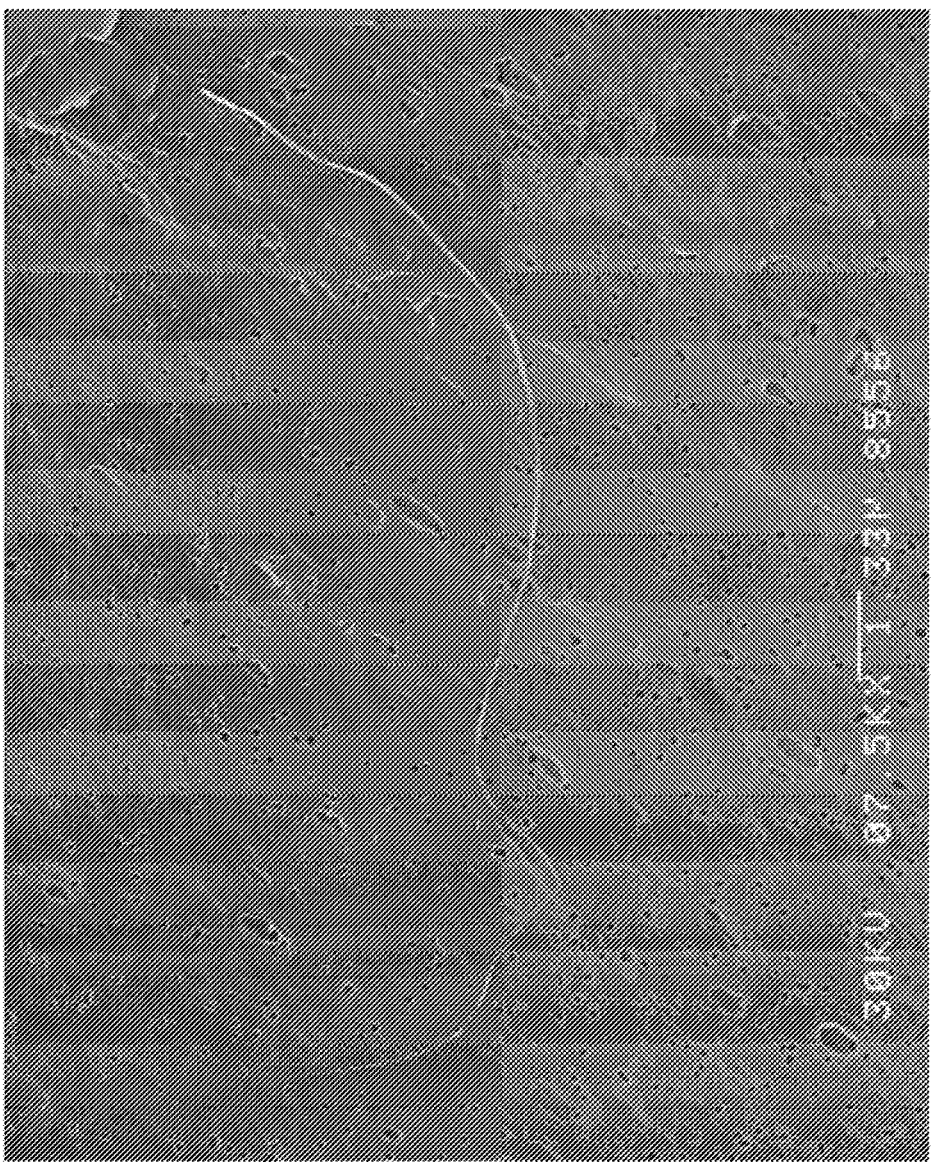
Figure 15D:
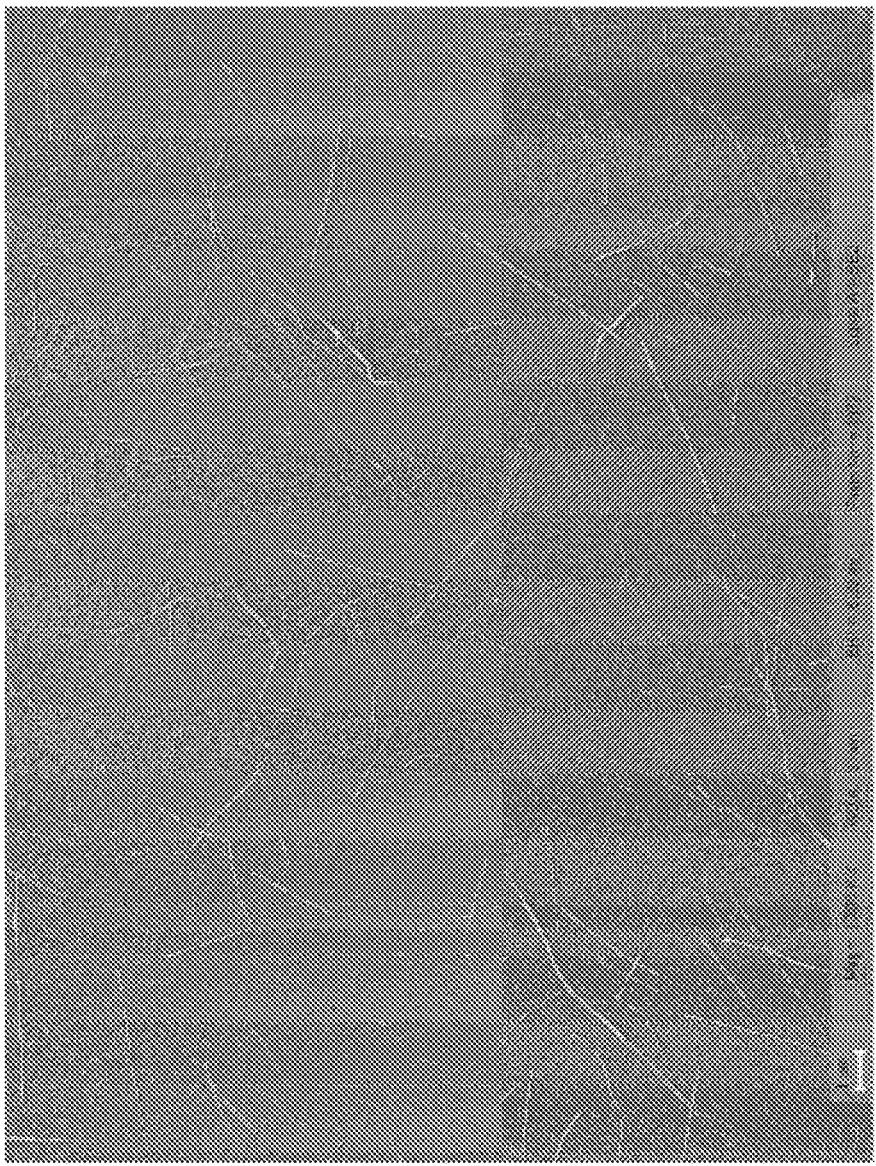

The chemical and physical structure of the fibers was maintained throughout irradiation as verified by infrared (IR) spectrum (FIG. 15B), elemental assay, and scanning electron microscopes (SEMs) analysis. Microscopic observation of irradiated fibers showed a decrease in the particle length (FIGS. 15C and 15D). The majority of the fibers are less than about 15 μm in length, with an average length of about 4 um.

6.7 Example 7: sNAG Nanofibers and Long Form p-GlcNAc Fibers Differ in their Effects on Metabolic Rate and Serum Deprivation of Umbilical Cord Vein Endothelial Cells Materials and Methods. Pooled, multiple-donor human umbilical cord vein endothelial cells (EC) (Cambrex) were maintained at 37° C. with 5% CO2 in endothelial basal medium 2 (Cambrex) supplemented with EC growth medium 2 SingleQuots as described by Cambrex procedures. Serum starvation was performed at 80-90% confluency in RPMI-1640 supplemented with 0.1% fetal calf serum (Gibco BRL) for 24 h followed by stimulation with VEGF 165 (20 ng/ml, R&D Systems) or with highly purified pGlcNAc nanofibers or sNAG nanofibers in sterile water (provided by Marine Polymer Technologies, Inc., Danvers, Mass., USA) with the amounts indicated in the figure descriptions. For cellular proliferation/viability assessment, 2 different assays were used: trypan blue exclusion by direct cell counts using a hemacytometer and an MTT [3-(4,5-dimethylthiazol-2yl)-2,5-diphenyltetrazolium bromide]assay in procedures described by the manufacturer (Promega).

Results—pGlcNAc: pGlcNAc did not affect metabolic rate. As shown in FIG. 16, pGlcNAc did not result in a higher metabolic rate as measured by MTT assays, indicating that this polymeric material was not causing marked increases in cellular proliferation.

pGlcNAc Protected EC from Cell Death Induced by Serum Starvation. To test if pGlcNAc fibers had a direct effect on EC, serum-starved EC cells were treated with VEGF or with different concentrations of pGlcNAc fibers. As shown in FIG. 17 at 48 h and 72 h after serum starvation, as compared with the total number of cells plated (control), there was about 2-fold reduction in the number of cells after 48 h or 72 h. At 48 h, this decrease in cell number was rescued by the addition of VEGF or by the addition of pGlcNAc fibers at either 50 or 100 μg/ml. At 72 h, the decrease in cell number was rescued by the addition of VEGF or largely rescued by the addition of pGlcNAc fibers at 100 jag/ml. These results indicated that like VEGF, pGlcNAc fiber treatment prevented cell death induced by serum deprivation.

Results—sNAG: sNAG Induced Marked Increase in Metabolic Rate. As measured by MTT assays, sNAG at 50, 100 or 200 μg/ml resulted in a higher metabolic rate of EC than VEGF (FIG. 18).

sNAG Did not Protect EC from Cell Death Induced by Serum Deprivation. To test if sNAG fibers had a direct effect on EC, serum-starved EC cells were treated with VEGF or with different concentrations of sNAG fibers. As shown in FIG. 19, at 48 h after serum starvation, as compared with the total number of cells plated (control), there was about 2-fold reduction in the number of cells. This decrease in cell number was rescued by the addition of VEGF but not by the addition of sNAG fibers at 50, 100 or 200 μg/ml. These results indicated that not like VEGF, sNAG fiber treatment did not prevent cell death induced by serum deprivation.

Conclusion: The above results demonstrate that sNAG, unlike long form pGlcNAc, increases the metabolic rate of serum-starved EC in a MTT assay and does not rescue apoptosis of serum-starved EC in a trypan blue exclusion test.

6.8 Example 8. Preclinical Testing of sNAG 6.8.1 Test Article

A test article comprising sNAG produced as previously described in Section 6.2.1 supra. was utilized. The test article was supplied sterile by Marine Polymer Technologies, Inc.

6.8.2 Biocompatibility Testing—L929 MEM Elusion Test—ISO 10993-5

Biocompatibility of the test article was tested in mouse fibroblast L929 mammalian cells. No biological reactivity (Grade 0) was observed in the L929 cells at 48 hours, post exposure to the test article. The observed cellular response obtained from the positive control article (Grade 4) and negative control article (Grade 0) confirmed the suitability of the test system. Based on the criteria of the protocol, the test article is considered non-toxic and meets the requirements of the Elution Test, International Organization for Standardization (ISO) 10993-5 guidelines. See Table X below.

TABLE X

REACTIVITY GRADES

| | Test Article | | | Controls | | | | | | | | |
| | | | | Medium | | | Ne2ative | | | Positive | | |
| Time | A | B | C | A | B | C | A | B | C | A | B | C |
|---|---|---|---|---|---|---|---|---|---|---|---|---|
| 0 Hours | 0 | 0 | 0 | 0 | 0 | 0 | 0 | 0 | 0 | 0 | 0 | 0 |
| 24 Hours | 0 | 0 | 0 | 0 | 0 | 0 | 0 | 0 | 0 | 3 | 3 | 3 |
| 48 Hours | 0 | 0 | 0 | 0 | 0 | 0 | 0 | 0 | 0 | 4 | 4 | 4 |

TABLE X-continued

REACTIVITY GRADES

| Grade | Reactivity | Description of Reactivity Zone |
|---|---|---|
| 0 | None | Discrete intracytoplasmic granules; no cell lysis |
| 1 | Slight | Not more than 20% of the cells are round, loosely attached, and without intracytoplasmic granules; occasional lysed cells are present |
| 2 | Mild | Not more than 50% of the cells are round and devoid of intracytoplasmic granules; no extensive cell lysis and empty areas between cells |
| 3 | Moderate | Not more than 70% of the cell layers contain rounded cells or are lysed |
| 4 | Severe | Nearly complete destruction of the cell layers |

6.8.3 Intramuscular Implantation Test—ISO—4 Week Implantation 6.8.3.1. Materials and Methods To evaluate the potential of the test article to induce local toxic effects, the Intramuscular Implantation Test—ISO—4 Week Implantation ("Intramuscular Implantation Test") was used. Briefly, the test article was implanted in the paravertebral muscle tissue of New Zealand White rabbits for a period of 4 weeks. The test article was then evaluated separately using two control articles: positive control Surgicel (Johnson and Johnson, NJ) and negative control High Density Polyethylene (Negative Control Plastic).

Preparation of Test and Control Articles. The test article measured approximately 1 mm to in width and 10 mm in length. The two control articles were prepared. The positive control, Surgicel (C1), measured approximately 1 mm in width by 10 mm in length and was received sterile. Negative Control Plastic (C2), measured approximately 1 mm in width by 10 mm in length and was sterilized by dipping in 70% ethanol.

Pre-Dose Procedure. Each animal was weighed prior to implantation. On the day of the test, the dorsal sides of the animals were clipped free of fur and loose hair was removed by means of a vacuum. Each animal was appropriately anesthetized. Prior to implantation, the area was swabbed with a surgical preparation solution.

Dose Administration. Four test article strips were surgically implanted into each of the paravertebral muscles of each rabbit, approximately 2.5 cm from the midline and parallel to the spinal column and approximately 2.5 cm from each other. The test article strips were implanted on one side of the spine. In a similar fashion, positive control article strips (Surgicel) were implanted in the contralateral muscle of each animal. Two negative control strips (Negative Control Plastic) were implanted caudal (toward the tail) to the test article and to C1 control implant sites on either side of the spine (total of four strips). A total of at least eight test article strips and eight of each control article strips are required for evaluation.

Post-Dose Procedures. The animals were maintained for a period of 4 weeks. The animals were observed daily for this period to ensure proper healing of the implant sites and for clinical signs of toxicity. Observations included all clinical manifestations. At the end of the observation period, the animals were weighed. Each animal was sacrificed by an injectable barbiturate. Sufficient time was allowed to elapse for the tissue to be cut without bleeding.

Gross Observations. The paravertebral muscles in which the test or control articles were implanted were excised in toto from each animal. The muscle tissue was removed by carefully slicing around the implant sites with a scalpel and lifting out the tissue. The excised implant tissues were examined grossly, but without using excessive invasive procedures that might have disrupted the integrity of this tissue for histopathological evaluation. The tissues were placed in properly labeled containers containing 10% neutral buffered formalin.

Histopathology. Following fixation in formalin, each of the implant sites was excised from the larger mass of tissue. The implant site, containing the implanted material, was examined macroscopically. Each site was examined for signs of inflammation, encapsulation, hemorrhaging, necrosis, and discoloration using the following scale:

0=Normal
1=Mild
2=Moderate
3=Marked

After macroscopic observation, the implant material was left in-situ and a slice of tissue containing the implant site was processed. Histologic slides of hematoxylin and eosin stained sections were prepared by Toxikon. The slides were evaluated and graded by light microscopic examination.

Pathological Assessment of the Effects of the Implant. The following categories of biological reaction were assessed by microscopic observation for each implant site:

1. Inflammatory Responses:
   a. Polymorphonuclear leukocytes
   b. Lymphocytes
   c. Eosinophils
   d. Plasma cells
   e. Macrophages
   f. Giant cells
   g. Necrosis
   h. Degeneration
2. Healing Responses:
   a. Fibrosis
   b. Fatty Infiltrate Each category of response was graded using the following scale:

0=Normal
0.5=Very Slight
1=Mild
2=Moderate
3=Marked

The relative size of the involved area was scored by assessing the width of the area from the implant/tissue interface to unaffected areas which have the characteristics of normal tissue and normal vascularity. Relative size of the involved area was scored using the following scale:

0=0 mm, No site
0.5=up to 0.5 mm, Very slight
1=0.6-1.0 mm, Mild
2=1.1-2.0 mm, Moderate
3=>2.0 mm, Marked The Intramuscular Implantation Test was conducted based upon the following references:

1. ISO 10993-6, 1994, Biological Evaluation of Medical Devices—Part 6: Tests for Local Effects After Implantation.

2. ISO 10993-12, 2002, Biological Evaluation of Medical Devices—Part 12: Sample Preparation and Reference Materials.

3. ASTM F981-04, 2004, Standard Practice for Assessment of Compatibility of Biomaterials for Surgical Implants with Respect to Effect of Materials on Muscle and Bone.

4. ASTM F763-04, 2004, Standard Practice for Short Term Screening of Implant Materials.

5. ISO/IEC 17025, 2005, General Requirements for the Competence of Testing and Calibration Laboratories.

The results of the Intramuscular Implantation Test were evaluated based upon the following criteria:

1. Calculated Rating: For each implanted site, a total score is determined. The average score of the test sites for each animal is compared to the average score of the control sites for that animal. The average difference between test and control sites for all animals is calculated and the initial Bioreactivity Rating is assigned as follows:

0-1.5 No Reaction*
>1.5-3.5 Mild Reaction
>3.5-6.0 Moderate Reaction
>6.0 Marked Reaction
*A negative calculation is reported as zero (0).

2. Modification of the Rating: The pathology observer reviews the calculated level of bioreactivity. Based on the observation of all factors (e.g., relative size, pattern of response, inflammatory vs. resolution), the pathology observer may revise the Bioreactivity Rating. Justification for the modification to the rating is presented in the narrative report (A descriptive narrative report regarding the biocompatibility of the test material is provided by the pathology observer).

6.8.3.2. Results

The results indicated that the test article was non-reactive when implanted for 4 weeks (Bioreactivity Rating of 0.2) when compared to positive control Surgicel; and non-reactive (Bioreactivity Rating of 0.0) when compared to negative control High Density Polyethylene (Negative Control Plastic).

Clinical Observation. Table XI below shows results of the macroscopic evaluation of the test article and control implant sites indicated no significant signs of inflammation, encapsulation, hemorrhage, necrosis, or discoloration at the 4 week time period. Some test sites and the majority of the positive control, Surgicel, were not seen macroscopically and serial sections were submitted for microscopic evaluation.

TABLE XI

Macroscopic Observations
4 Week Implantation

| Tissue Size: | T1 | T2 | T3 | T4 | Test Ave. | C1-1 | C1-2 | C1-3 | C1-4 | Control C1 Ave. | C2-1 | C2-2 | C2-3 | C2-4 | Control C2 Ave. |
|---|---|---|---|---|---|---|---|---|---|---|---|---|---|---|---|
| Animal No. 60959 ||||||||||||||||
| Inflammation | 0 | NSF | 0 | NSF | 0 | NSF | NSF | NSF | NSF | N/A | 0 | 0 | 0 | 0 | 0 |
| Encapsulation | 0 | NSF | 0 | NSF | 0 | NSF | NSF | NSF | NSF | N/A | 0 | 0 | 0 | 0 | 0 |
| Hemorrhage | 0 | NSF | 0 | NSF | 0 | NSF | NSF | NSF | NSF | N/A | 0 | 0 | 0 | 0 | 0 |
| Necrosis | 0 | NSF | 0 | NSF | 0 | NSF | NSF | NSF | NSF | N/A | 0 | 0 | 0 | 0 | 0 |
| Discoloration | 0 | NSF | 0 | NSF | 0 | NSF | NSF | NSF | NSF | N/A | 0 | 0 | 0 | 0 | 0 |
| Total | 0 | N/A | 0 | N/A | | N/A | N/A | N/A | N/A | | 0 | 0 | 0 | 0 | |
| Animal No. 60961 ||||||||||||||||
| Inflammation | NSF | NSF | NSF | NSF | N/A | NSF | NSF | NSF | NSF | N/A | 0 | 0 | NSF | 0 | 0 |
| Encapsulation | NSF | NSF | NSF | NSF | N/A | NSF | NSF | NSF | NSF | N/A | 0 | 0 | NSF | 0 | 0 |
| Hemorrhage | NSF | NSF | NSF | NSF | N/A | NSF | NSF | NSF | NSF | N/A | 0 | 0 | NSF | 0 | 0 |
| Necrosis | NSF | NSF | NSF | NSF | N/A | NSF | NSF | NSF | NSF | N/A | 0 | 0 | NSF | 0 | 0 |
| Discoloration | NSF | NSF | NSF | NSF | N/A | NSF | NSF | NSF | NSF | N/A | 0 | 0 | NSF | 0 | 0 |
| Total | N/A | N/A | N/A | N/A | | N/A | N/A | N/A | N/A | | 0 | 0 | N/A | 0 | |
| Animal No. 60968 ||||||||||||||||
| Inflammation | NSF | NSF | NSF | NSF | N/A | NSF | NSF | NSF | NSF | N/A | 0 | 0 | 0 | 0 | 0 |
| Encapsulation | NSF | NSF | NSF | NSF | N/A | NSF | NSF | NSF | NSF | N/A | 0 | 0 | 0 | 0 | 0 |
| Hemorrhage | NSF | NSF | NSF | NSF | N/A | NSF | NSF | NSF | NSF | N/A | 0 | 0 | 0 | 0 | 0 |
| Necrosis | NSF | NSF | NSF | NSF | N/A | NSF | NSF | NSF | NSF | N/A | 0 | 0 | 0 | 0 | 0 |
| Discoloration | NSF | NSF | NSF | NSF | N/A | NSF | NSF | NSF | NSF | N/A | 0 | 0 | 0 | 0 | 0 |
| Total | N/A | N/A | N/A | N/A | | N/A | N/A | N/A | N/A | | 0 | 0 | 0 | 0 | |

T = test site (representative sections were submitted for microscopic assessment)
C1 = Surgicel (Due to the nature of the material, representative sections were submitted for microscopic assessment)
C2 = Negative Control High Density Polyethylene (Negative Control Plastic)
Grading Scale
0 = no reaction
1 = mild reaction
2 = moderate reaction
3 = marked reaction
NSF = No Site Found
N/A = Not Application Implantation Site Observations (Microscopic). Table XII below shows results of the microscopic evaluation of the test article implant sites indicated no significant signs of inflammation, fibrosis, hemorrhage, necrosis, or degeneration as compared to each of the control article sites. The Bioreactivity Rating for the 4 week time period (average of three animals) was 0.2, (C1—Surgicel) and 0.0 (C2—Negative Control Plastic) indicating no reaction as compared to either of the control implant sites. The pathologist noted there was a moderate polymorphic and histiocytic (macrophages) infiltrate around the in situ test article that was not unexpected given the nature of the test material.

TABLE XII

Microscopic Observations
4 Week Implantation

Animal No. 60959

| | Categories | | | | | | | | | | |
|---|---|---|---|---|---|---|---|---|---|---|---|
| | Test Sites** | | | Control Sites | | | | | | | |
| Reaction | T1 | T2 | T3 | C1-1 | C1-2 | C1-3 | C1-4 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| *Polymorphs | 0.0 | 0.5 | 0.5 | 0.0 | 0.0 | 0.0 | 0.0 | 0.0 | 0.0 | 0.0 | 0.0 |
| *Lymphocytes | 0.0 | 0.0 | 0.0 | 0.0 | 0.0 | 0.0 | 0.0 | 0.0 | 0.0 | 0.0 | 0.0 |
| *Eosinophils | 0.0 | 0.0 | 0.0 | 0.0 | 0.0 | 0.0 | 0.0 | 0.0 | 0.0 | 0.0 | 0.0 |
| *Plasma Cells | 0.0 | 0.0 | 0.0 | 0.0 | 0.0 | 0.0 | 0.0 | 0.0 | 0.0 | 0.0 | 0.0 |
| *Macrophages | 0.5 | 0.5 | 0.5 | 0.5 | 0.5 | 0.5 | 0.5 | 0.5 | 0.5 | 0.5 | 0.5 |
| *Giant Cells | 0.0 | 0.0 | 0.0 | 0.0 | 0.0 | 0.0 | 0.0 | 0.0 | 0.0 | 0.0 | 0.0 |
| *Degeneration | 0.5 | 0.5 | 0.5 | 0.5 | 0.0 | 0.5 | 0.0 | 0.0 | 0.0 | 0.0 | 0.0 |
| *Necrosis | 0.0 | 0.0 | 0.0 | 0.0 | 0.0 | 0.0 | 0.0 | 0.0 | 0.0 | 0.0 | 0.0 |
| *Fibrosis | 0.5 | 0.5 | 0.5 | 0.5 | 0.5 | 0.5 | 0.5 | 0.5 | 0.5 | 0.5 | 0.5 |
| *Fatty Infiltrate | 0.0 | 0.0 | 0.5 | 0.0 | 0.5 | 0.0 | 0.5 | 0.5 | 0.5 | 0.0 | 0.5 |
| Total | 1.5 | 2.0 | 2.5 | 1.5 | 1.5 | 1.5 | 1.5 | 1.5 | 1.5 | 1.0 | 1.5 |

T = Test Site
C1 = Surgicel
C2 = Negative Control High Density Polyethylene (Negative Control Plastic)
Animal Test Score (Average*) = 2.0
Animal C1 Score (Average*) = 1.5
Animal C2 Score (Average*) = 1.4
Animal Score (Average Test Score − Average C1 Score) = 0.5
Animal Score (Average Test Score − Average C2 Score) = 0.6
*Used in calculation of Bioreactivity Rating.
**No site found in T4.

Animal No. 60961

| | Categories | | | | | | | | |
|---|---|---|---|---|---|---|---|---|---|
| | Test Sites** | | | Control Sites** | | | | | |
| Reaction | T1 | T3 | T4 | C1-1 | C1-3 | C1-4 | C2-1 | C2-2 | C2-3 |
| Foreign Debris | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 |
| *Polymorphs | 0.0 | 0.0 | 0.5 | 0.5 | 0.0 | 0.5 | 0.5 | 0.5 | 0.5 |
| *Lymphocytes | 0.0 | 0.0 | 0.0 | 0.0 | 0.0 | 0.0 | 0.0 | 0.0 | 0.0 |
| *Eosinophils | 0.0 | 0.0 | 0.0 | 0.0 | 0.0 | 0.0 | 0.0 | 0.0 | 0.0 |
| *Plasma Cells | 0.0 | 0.0 | 0.0 | 0.0 | 0.0 | 0.0 | 0.0 | 0.0 | 0.0 |
| *Macrophages | 0.5 | 0.5 | 0.5 | 0.5 | 0.5 | 0.5 | 0.5 | 0.5 | 0.5 |
| *Giant Cells | 0.0 | 0.0 | 0.0 | 0.0 | 0.0 | 0.0 | 0.0 | 0.0 | 0.0 |
| *Degeneration | 0.5 | 0.5 | 0.5 | 0.5 | 0.5 | 0.5 | 0.5 | 0.5 | 0.5 |
| *Necrosis | 0.0 | 0.0 | 0.0 | 0.0 | 0.0 | 0.0 | 0.0 | 0.0 | 0.0 |
| *Fibrosis | 0.5 | 0.5 | 0.5 | 0.5 | 0.5 | 0.5 | 0.5 | 0.5 | 0.5 |
| *Fatty Infiltrate | 0.0 | 0.5 | 0.0 | 0.5 | 0.0 | 0.5 | 0.5 | 0.5 | 0.5 |
| Total | 1.5 | 2.0 | 2.0 | 2.5 | 1.5 | 2.5 | 2.5 | 2.5 | 2.5 |

T = Test Site
C1 = Surgical
C2 = Negative Control High Density Polyethylene (Negative Control Plastic)
Animal Test Score (Average*) 1.8
Animal C1 Score (Average*) 2.2
Animal C2 Score (Average*) 2.5
Animal Score (Average Test Score − Average C1 Score) = −0.4
Animal Score (Average Test Score − Average C2 Score) = −0.7
*Used in calculation of Bioreactivity Rating.
**No site found in T2, C1-2, and C2-4.

TABLE XII-continued

Microscopic Observations
4 Week Implantation

Animal No. 60968

| | Categories | | | | | | | | | | |
|---|---|---|---|---|---|---|---|---|---|---|---|
| | Test Sites | | | | Control Sites** | | | | | | |
| Reaction | T1 | T2 | T3 | T4 | C1-1 | C1-2 | C1-3 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| *Polymorphs | 0.0 | 0.5 | 0.0 | 0.5 | 0.0 | 0.0 | 0.0 | 0.5 | 0.5 | 0.0 | 0.5 |
| *Lymphocytes | 0.0 | 0.0 | 0.0 | 0.0 | 0.0 | 0.0 | 0.0 | 0.0 | 0.0 | 0.0 | 0.0 |
| *Eosinophils | 0.0 | 0.0 | 0.0 | 0.0 | 0.0 | 0.0 | 0.0 | 0.0 | 0.0 | 0.0 | 0.0 |
| *Plasma Cells | 0.0 | 0.0 | 0.0 | 0.0 | 0.0 | 0.0 | 0.0 | 0.0 | 0.0 | 0.0 | 0.0 |
| *Macrophages | 0.5 | 0.5 | 0.5 | 0.5 | 0.5 | 0.5 | 0.5 | 0.5 | 0.5 | 0.5 | 0.5 |
| *Giant Cells | 0.0 | 0.0 | 0.0 | 0.0 | 0.0 | 0.0 | 0.0 | 0.0 | 0.0 | 0.0 | 0.0 |
| *Degeneration | 0.5 | 0.5 | 0.5 | 0.5 | 0.5 | 0.5 | 0.5 | 0.5 | 0.5 | 0.5 | 0.5 |
| *Necrosis | 0.0 | 0.0 | 0.0 | 0.0 | 0.0 | 0.0 | 0.0 | 0.0 | 0.0 | 0.0 | 0.0 |
| *Fibrosis | 0.5 | 0.5 | 0.5 | 0.5 | 0.5 | 0.5 | 0.5 | 0.5 | 0.5 | 0.5 | 0.5 |
| *Fatty Infiltrate | 0.5 | 0.5 | 0.5 | 0.5 | 0.5 | 0.0 | 0.5 | 0.5 | 0.5 | 0.5 | 0.5 |
| Total | 2.0 | 2.5 | 2.0 | 2.5 | 2.0 | 1.5 | 2.0 | 2.5 | 2.5 | 2.0 | 2.5 |

T = Test Site
C1 = Surgicel
C2 = Negative Control High Density Polyethylene (Negative Control Plastic)
Animal Test Score (Average*) = 2.3
Animal C1 Score (Average*) = 1.8
Animal C2 Score (Average*) = 2.4
Animal Score (Average Test Score − Average C1 Score) = 0.5
Animal Score (Average Test Score − Average C2 Score) = 0.1
*Used in calculation of Bioreactivity Rating.
**No site found in C1-4.

| | C1 | C2 |
|---|---|---|
| Animal Score 60759 = | 0.5 | 0.6 |
| Animal Score 60961 = | −0.4 | −0.7 |
| Animal Score 60968 = | 0.5 | −0.1 |

Bioreactivity Rating = 0.2 = No Reaction
Bioreactivity Rating = −0.1 = No Reaction 6.8.4 Intracutaneous Injection Test—ISO 10993-10

USP 0.9% Sodium Chloride for Injection (NaCl) and Cottonseed Oil (CSO) extracts of the test article were evaluated for their potential to produce irritation after intracutaneous injection in New Zealand White rabbits. The test article sites did not show a significantly greater biological reaction than the sites injected with the control article. Based on the criteria of the protocol, the test article is considered a negligible irritant and meets the requirements of the ISO 10993-10 guidelines. Results are shown below in Table XIII.

TABLE XIII

Intracutaneous Test Skin Reaction Scores

| | | | Site Numbers Scoring (ER/ED) | | | | | | | | |
|---|---|---|---|---|---|---|---|---|---|---|---|
| Animal # | Vehicle | Time | T-1 | T-2 | T-3 | T-4 | T-5 | C-1 | C-2 | C-3 | C-4 | C-5 |
| | | | NaCl Extract | | | | | | | | | |
| 61917 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| 61919 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | | Total | | | 0.0 | | | | | 0.0 | | |
| | | | CSO Extract | | | | | | | | | |
| 61917 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |

TABLE XIII-continued

Intracutaneous Test Skin Reaction Scores

| Animal # | Vehicle | Time | Site Numbers Scoring (ER/ED) | | | | | | | | | |
|---|---|---|---|---|---|---|---|---|---|---|---|---|
| | | | T-1 | T-2 | T-3 | T-4 | T-5 | C-1 | C-2 | C-3 | C-4 | C-5 |
| 61919 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | Total | | | | 0.0 | | | | | 0.0 | | |

† = Immediately after injection, not used for the evaluation criteria.
Overall Mean Score* for Test Article = 0.0
Overall Mean Score* for Control Article = 0.0
Difference between Test Article and Control Article Overall Mean Score = 0.0 − 0.0 = 0.0
ER = Erythema;
ED = Edema;
T = Test Sites;
C = Control Sites
*Overall Mean Score = Total erythema plus edema scores divided by 12 (2 animals × 3 scoring periods × 2 scoring categories)

6.8.5 Kligman Maximization Test—ISO 10993-10

UPS 0.9% Sodium Chloride for Injection (NaCl) and Cottonseed Oil (CSO) extracts of the test article elicited no intradermal reaction in Hartley guinea pigs at the challenge (0% sensitization), following an induction phase. Therefore, as defined by the scoring system of Kligman, this is a Grade I reaction and the test article is classified as having weak allergenic potential. Based on the criteria of the protocol, a Grade I sensitization rate is not considered significant and the test article meets the requirements of the ISO 10993-10 guidelines. Results are shown below in Table XIV.

TABLE XIV

Skin Examination Data

| Group | Animal # | Sex | Scores | | | Percent Animals Sensitized | Allergenic Potential |
|---|---|---|---|---|---|---|---|
| | | | Day 25 | Day 26 | Day 27 | | |
| Test Article (NaCl Extract) | 1 | Male | 0 | 0 | 0 | 0% | Weak |
| | 2 | Male | 0 | 0 | 0 | | |
| | 3 | Male | 0 | 0 | 0 | | |
| | 4 | Male | 0 | 0 | 0 | | |
| | 5 | Male | 0 | 0 | 0 | | |
| | 6 | Female | 0 | 0 | 0 | | |
| | 7 | Female | 0 | 0 | 0 | | |
| | 8 | Female | 0 | 0 | 0 | | |
| | 9 | Female | 0 | 0 | 0 | | |
| | 10 | Female | 0 | 0 | 0 | | |
| Test Article (CSO Extract) | 11 | Male | 0 | 0 | 0 | 0% | Weak |
| | 12 | Male | 0 | 0 | 0 | | |
| | 13 | Male | 0 | 0 | 0 | | |
| | 14 | Male | 0 | 0 | 0 | | |
| | 15 | Male | 0 | 0 | 0 | | |
| | 16 | Female | 0 | 0 | 0 | | |
| | 17 | Female | 0 | 0 | 0 | | |
| | 18 | Female | 0 | 0 | 0 | | |
| | 19 | Female | 0 | 0 | 0 | | |
| | 20 | Female | 0 | 0 | 0 | | |
| Negative Control (NaCl) | 21 | Male | 0 | 0 | 0 | 0% | Weak |
| | 22 | Male | 0 | 0 | 0 | | |
| | 23 | Female | 0 | 0 | 0 | | |
| | 24 | Female | 0 | 0 | 0 | | |
| | 25 | Female | 0 | 0 | 0 | | |
| Negative Control (CSO) | 26 | Male | 0 | 0 | 0 | 0% | Weak |
| | 27 | Male | 0 | 0 | 0 | | |
| | 28 | Female | 0 | 0 | 0 | | |
| | 29 | Female | 0 | 0 | 0 | | |
| | 30 | Female | 0 | 0 | 0 | | |
| Positive Control (DNCB) | 31 | Male | 2 | 1 | 0 | 100% | Extreme |
| | 32 | Male | 2 | 2 | 1 | | |
| | 33 | Female | 3 | 2 | 1 | | |
| | 34 | Female | 3 | 2 | 1 | | |
| | 35 | Female | 3 | 3 | 2 | | |

TABLE XIV-continued

| Skin Examination Data | | |
|---|---|---|
| Sensitization Rate (%) | Grade | Class |
| 0-8 | I | Weak |
| 9-28 | II | Mild |
| 29-64 | III | Moderate |
| 65-80 | IV | Strong |
| 81-100 | V | Extreme |

The test results are interpreted based upon the percentage sensitization observed.

7. INCORPORATION BY REFERENCE

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

8. SEQUENCE LISTING

This application incorporates by reference in its entirety the Computer Readable Form (CRF) of a Sequence Listing in ASCII text format submitted bia EFS-Web. The Sequence Listing text file submitted via EFS-Web, entitled 7867-167-999_SEQ_LISTING, was created on Apr. 5, 2019, and is 1,959 bytes in size.

What is claimed is:

1. A method for treating a bacterial infection of the skin at the hair follicles of a subject in need thereof, comprising topically administering a composition comprising shortened fibers of poly-N-acetylglucosamine ("sNAG nanofibers"), wherein a) the sNAG nanofibers are from 1 µm to less than 10 µm in length; or b) more than 50% of the sNAG nanofibers are between about 1 to 15 µm in length, wherein the sNAG nanofibers comprise 70% or more than 70% of N-acetylglucosamine monosaccharides, and wherein the sNAG nanofibers do not have an effect on bacterial growth or survival of *Staphylococcus aureus* bacterial cultures in vitro.

2. A method for treating folliculitis of a subject in need thereof, comprising topically administering a composition comprising shortened fibers of poly-N-acetylglucosamine ("sNAG nanofibers"), wherein a) the sNAG nanofibers are from 1 µm to less than 10 µm in length; or b) more than 50% of the sNAG nanofibers are between about 1 to 15 µm in length, wherein the sNAG nanofibers comprise 70% or more than 70% of N-acetylglucosamine monosaccharides, and wherein the sNAG nanofibers do not have an effect on bacterial growth or survival of *Staphylococcus aureus* bacterial cultures in vitro.

3. The method of claim 1, wherein the infection is with a bacteria of one or more of the following species: *Pseudomonas aeruginosa* or *Staphylococcus aureus*.

4. The method of claim 2, wherein the folliculitis is associated with a bacterial infection by one or more of the following species: *Pseudomonas aeruginosa* or *Staphylococcus aureus*.

5. The method of claim 1, wherein the sNAG nanofibers are effective to (i) reduce the severity of the bacterial infection or one or more symptoms of the bacterial infection, (ii) reduce the duration of the bacterial infection or one or more symptoms of the bacterial infection, or (iii) eradicate one or more symptoms associated with the bacterial infection.

6. The method of claim 1, wherein the subject is a human.

7. The method of claim 2, wherein the subject is a human.

8. The method of claim 1, wherein the composition is formulated as a liquid, a suspension, a paste, a cream, a gel, an ointment, a membrane, a powder, or a spray.

9. The method of claim 2, wherein the composition is formulated as a liquid, a suspension, a cream, a paste, a gel, an ointment, a membrane, a powder, or a spray.

10. The method of claim 1, wherein the composition comprises one or more additional anti-bacterial agents.

11. The method of claim 2, wherein the composition comprises one or more additional anti-bacterial agents.

12. The method of claim 1, wherein the composition is not for administration with an immunomodulator.

13. The method of claim 2, wherein the composition is not for administration with an immunomodulator.

14. The method of claim 1, wherein the composition does not comprise an additional active ingredient.

15. The method of claim 2, wherein the composition does not comprise an additional active ingredient.

16. The method of claim 1, wherein more than 50% of the sNAG nanofibers are between about 1 to 10 μm in length.

17. The method of claim 1, wherein more than 50% of the sNAG nanofibers are between about 1 to 10 μm in length.

18. The method of claim 1, wherein the sNAG nanofibers fibers are between 4 μm and 7 μm in average length.

19. The method of claim 2, wherein the sNAG nanofibers fibers are between 4 μm and 7 μm in average length.

20. The method of claim 1, wherein the length of the fibers is determined by scanning electron microscopic (SEM) analysis.

21. The method of claim 2, wherein the length of the fibers is determined by scanning electron microscopic (SEM) analysis.

22. The method of claim 1, wherein the sNAG nanofibers were produced from microalgal poly-N-acetylglucosamine.

23. The method of claim 2, wherein the sNAG nanofibers were produced from microalgal poly-N-acetylglucosamine.

24. The method of claim 1, wherein the sNAG nanofibers comprise 80% or more than 80% of N-acetylglucosamine monosaccharides.

25. The method of claim 2, wherein the sNAG nanofibers comprise 80% or more than 80% of N-acetylglucosamine monosaccharides.

26. The method of claim 1, wherein the sNAG nanofibers have the chemical and physical structure of microalgal poly-N-acetylglucosamine fibers of dimensions averaging 20-50 nm×1-2 nm×100 μm as determined by infrared (IR) spectrum, elemental assay, and scanning electron microscopes (SEMs) analysis.

27. The method of claim 2, wherein the sNAG nanofibers have the chemical and physical structure of microalgal poly-N-acetylglucosamine fibers of dimensions averaging 20-50 nm×1-2 nm×100 μm as determined by infrared (IR) spectrum, elemental assay, and scanning electron microscopes (SEMs) analysis.

28. The method of claim 1, wherein the sNAG nanofibers have an average molecular weight between about 40,000 daltons and about 80,000 daltons.

29. The method of claim 2, wherein the sNAG nanofibers have an average molecular weight between about 40,000 daltons and about 80,000 daltons.

30. The method of claim 1, wherein the poly-N-acetylglucosamine has a $\beta\text{-}1\rightarrow 4$ configuration.

31. The method of claim 2, wherein the poly-N-acetylglucosamine has a $\beta\text{-}1\rightarrow 4$ configuration.

* * * * *

```
SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: primer Akt1 F

<400> SEQUENCE: 1
gaggccgtca gccacagtct g                                              21

<210> SEQ ID NO 2
<211> LENGTH: 21
<212> TYPE: DNA
<213> ORGANISM: Artificial Sequence
<220> FEATURE:
<223> OTHER INFORMATION: primer Akt1 R

<400> SEQUENCE: 2
atgagcgacg tggctattgt g                                              21

<210> SEQ ID NO 3
<211> LENGTH: 19
<212> TYPE: DNA
<213> ORGANISM: Artificial Sequence
<220> FEATURE:
<223> OTHER INFORMATION: primer beta-Defensin3 F

<400> SEQUENCE: 3
gtggggtgaa gcctagcag                                                 19

<210> SEQ ID NO 4
<211> LENGTH: 20
<212> TYPE: DNA
<213> ORGANISM: Artificial Sequence
<220> FEATURE:
<223> OTHER INFORMATION: primer beta-Defensin 3 R

<400> SEQUENCE: 4
tttctttctt cggcagcatt                                                20
```

```
<210> SEQ ID NO 5
<211> LENGTH: 20
<212> TYPE: DNA
<213> ORGANISM: Artificial Sequence
<220> FEATURE:
<223> OTHER INFORMATION: primer alfa-Defensin1 F

<400> SEQUENCE: 5
cactccaggc aagagctgat                                               20

<210> SEQ ID NO 6
<211> LENGTH: 20
<212> TYPE: DNA
<213> ORGANISM: Artificial Sequence
<220> FEATURE:
<223> OTHER INFORMATION: primer alfa-Defensin1 R

<400> SEQUENCE: 6
tccctggtag atgcaggttc                                               20

<210> SEQ ID NO 7
<211> LENGTH: 20
<212> TYPE: DNA
<213> ORGANISM: Artificial Sequence
<220> FEATURE:
<223> OTHER INFORMATION: primer S26 F

<400> SEQUENCE: 7
ctccggtccg tgcctccaag                                               20

<210> SEQ ID NO 8
<211> LENGTH: 21
<212> TYPE: DNA
<213> ORGANISM: Artificial Sequence
<220> FEATURE:
<223> OTHER INFORMATION: primer S26 R

<400> SEQUENCE: 8
cagagaatag cctgtcttca g                                             21
```